United States Patent
Cole et al.

(10) Patent No.: US 11,883,027 B2
(45) Date of Patent: Jan. 30, 2024

(54) SYSTEMS AND METHODS FOR MICROVASCULAR ANASTOMOTIC COUPLER RING DELIVERY DEVICE

(71) Applicant: Dignity Health, San Francisco, CA (US)

(72) Inventors: Tyler Cole, San Francisco, CA (US); Dakota Graham, San Francisco, CA (US)

(73) Assignee: Dignity Health, San Francisco, CA (US)

( * ) Notice: Subject to any disclaimer, the term of this patent is extended or adjusted under 35 U.S.C. 154(b) by 0 days.

(21) Appl. No.: 18/249,020

(22) PCT Filed: Oct. 15, 2021

(86) PCT No.: PCT/US2021/055218
§ 371 (c)(1),
(2) Date: Apr. 13, 2023

(87) PCT Pub. No.: WO2022/081999
PCT Pub. Date: Apr. 21, 2022

(65) Prior Publication Data
US 2023/0285025 A1    Sep. 14, 2023

Related U.S. Application Data

(60) Provisional application No. 63/226,333, filed on Jul. 28, 2021, provisional application No. 63/092,034, filed on Oct. 15, 2020.

(51) Int. Cl.
*A61B 17/11* (2006.01)

(52) U.S. Cl.
CPC ....... *A61B 17/11* (2013.01); *A61B 2017/1107* (2013.01); *A61B 2017/1125* (2013.01)

(58) Field of Classification Search
CPC .... A61B 2017/1107; A61B 2017/1103; A61B 2017/1125; A61B 17/11
See application file for complete search history.

(56) References Cited

U.S. PATENT DOCUMENTS 3,316,914 A  *  5/1967  Collito .................. A61B 17/11
                                                    227/19
6,352,543 B1    3/2002  Cole
(Continued)

OTHER PUBLICATIONS

Patent Cooperation Treaty, International Search Report and Written Opinion, International Application No. PCT/US2021/055218, dated Jan. 19, 2022, 4 pages.

*Primary Examiner* — Diane D Yabut
*Assistant Examiner* — Christina C Lauer
(74) *Attorney, Agent, or Firm* — Polsinelli PC

(57) ABSTRACT

Various embodiments of a device for deep surgical corridor microvascular anastomosis are described herein. A device, comprising: an elongated body; a rod disposed at least partially within the channel of the elongated body; an actuator in association with the elongated body and the rod, wherein the actuator is operable to actuate the rod in a first axial direction; and a pair of coupling arms in association with the distal portion of the rod, wherein the actuator is operable to actuate the rod in a first axial direction such that the pivotable end of each coupling arm of the pair of coupling arms is consequently actuated in the first axial direction such that the pair of coupling arms are parallel with one another in a closed configuration.

6 Claims, 59 Drawing Sheets

(56) References Cited

U.S. PATENT DOCUMENTS

| | | |
|---|---|---|
| 7,547,311 B2 | 6/2009 | Ortiz |
| 8,105,345 B2 | 1/2012 | Golden et al. |
| 10,149,674 B2 | 12/2018 | Angus et al. |
| 2014/0046347 A1 | 2/2014 | Cully et al. |
| 2020/0205834 A1* | 7/2020 | Drochner ............... A61B 17/11 |

* cited by examiner

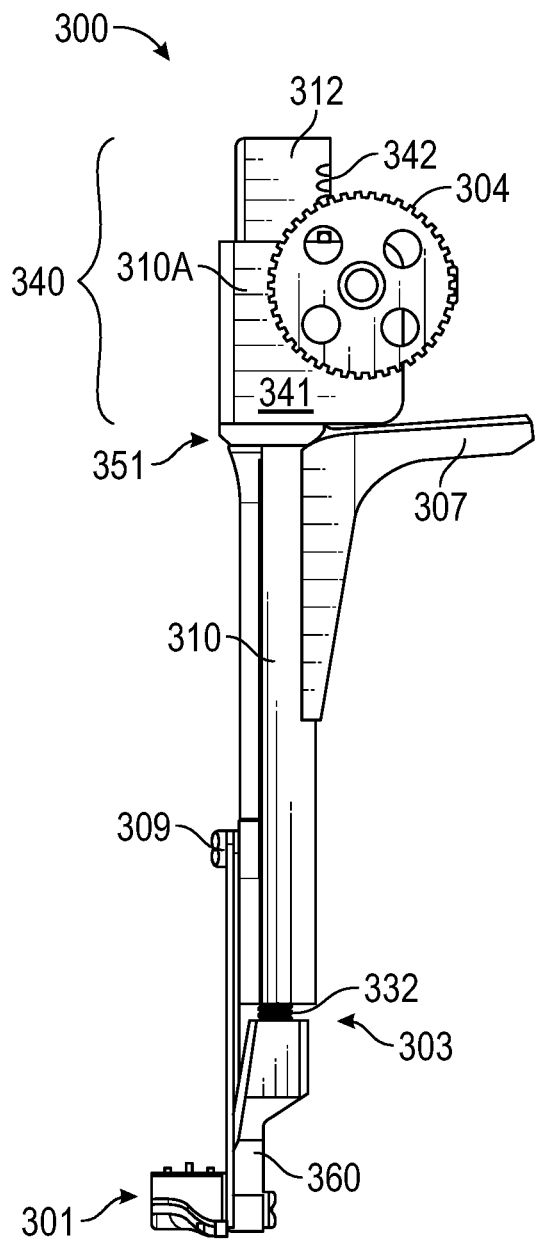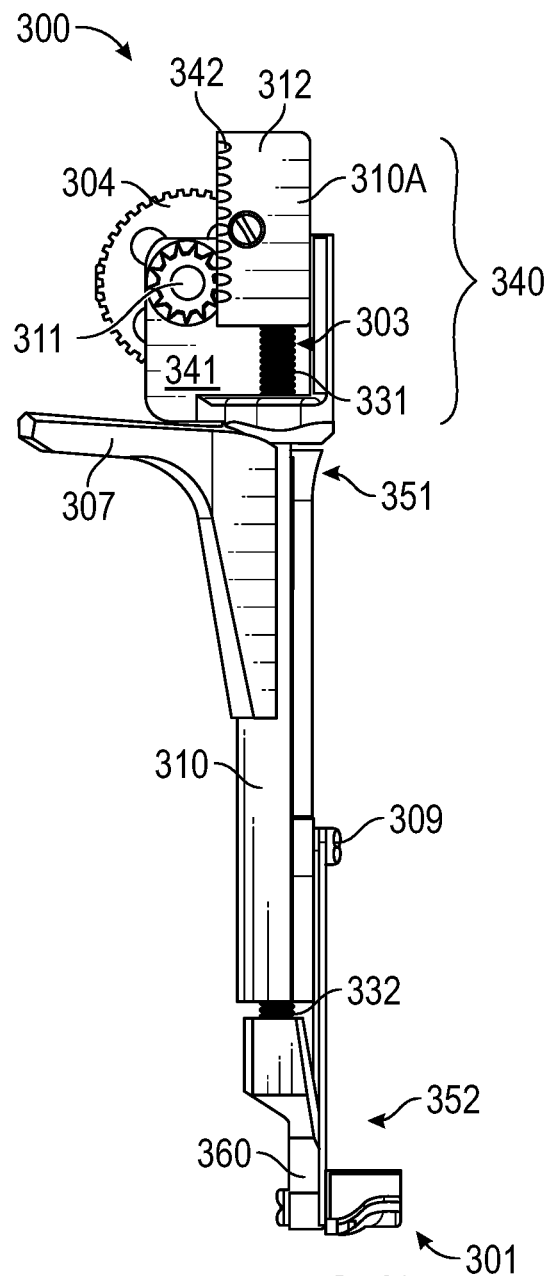
FIG. 12
FIG. 13

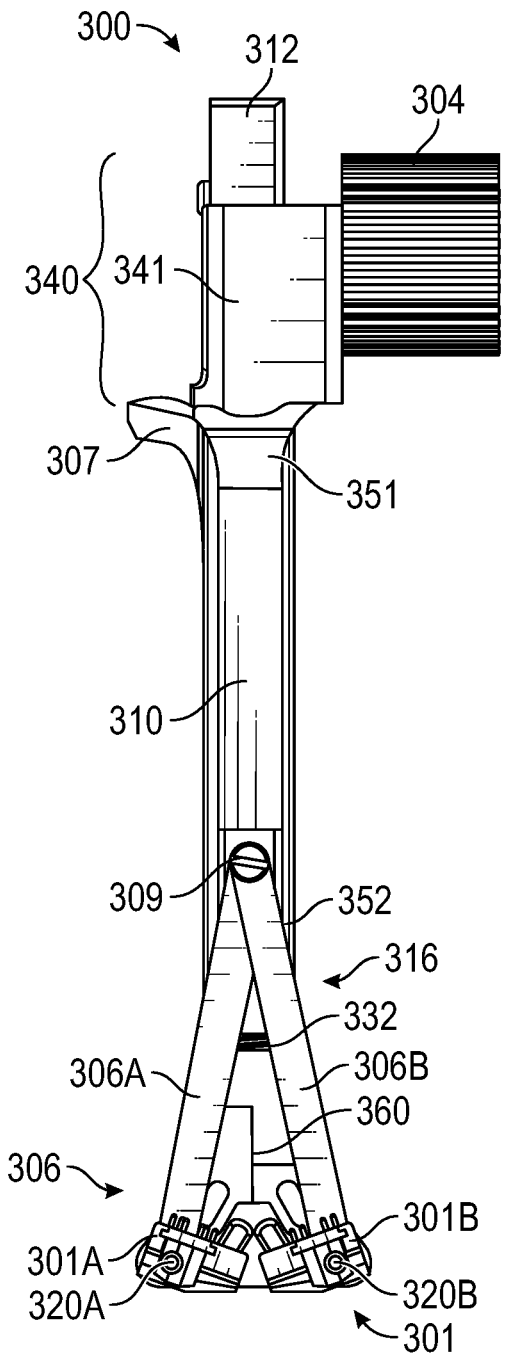
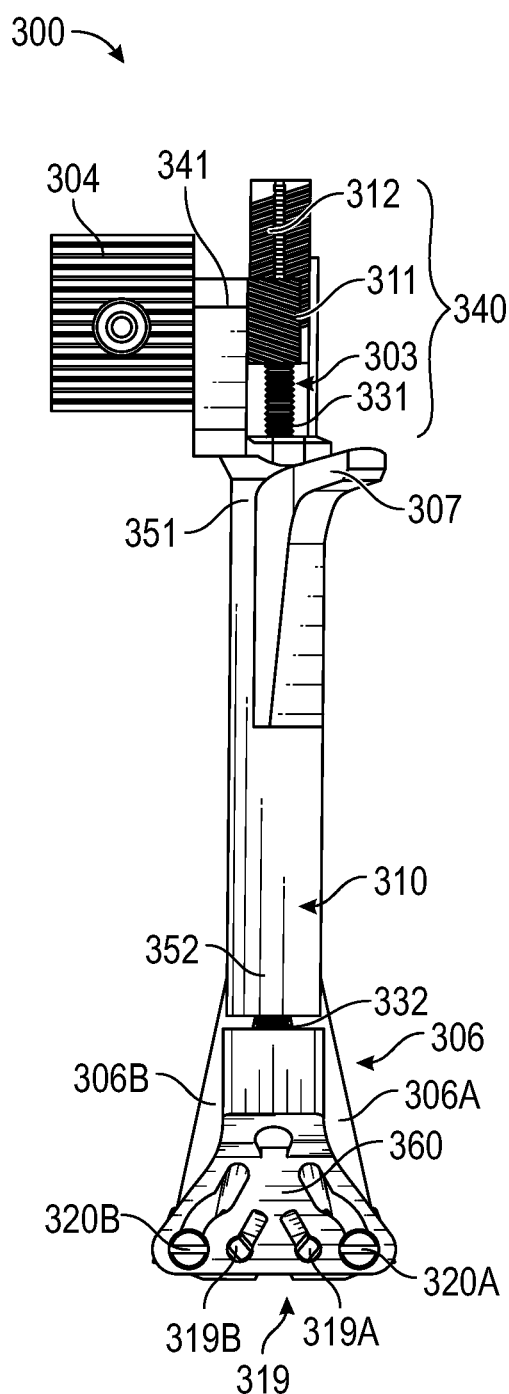
FIG. 14
FIG. 15

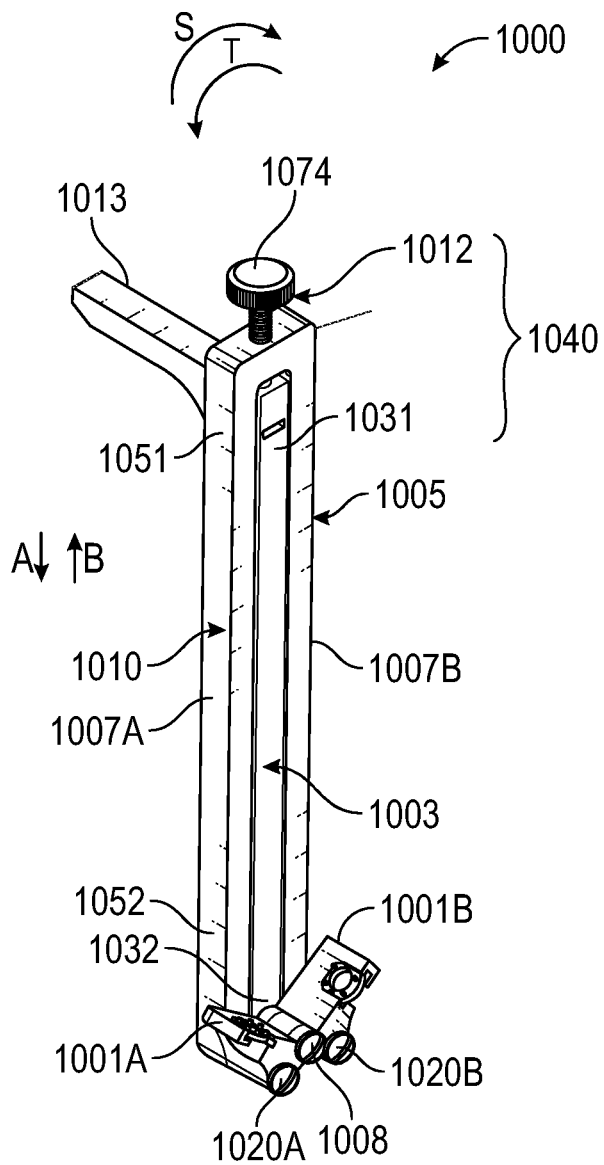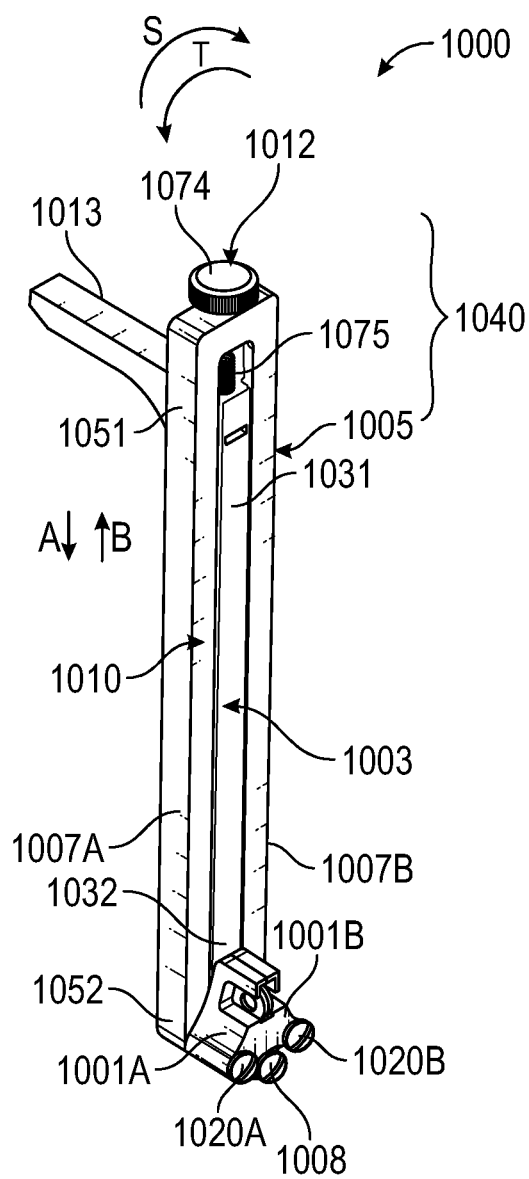
FIG. 65
FIG. 66

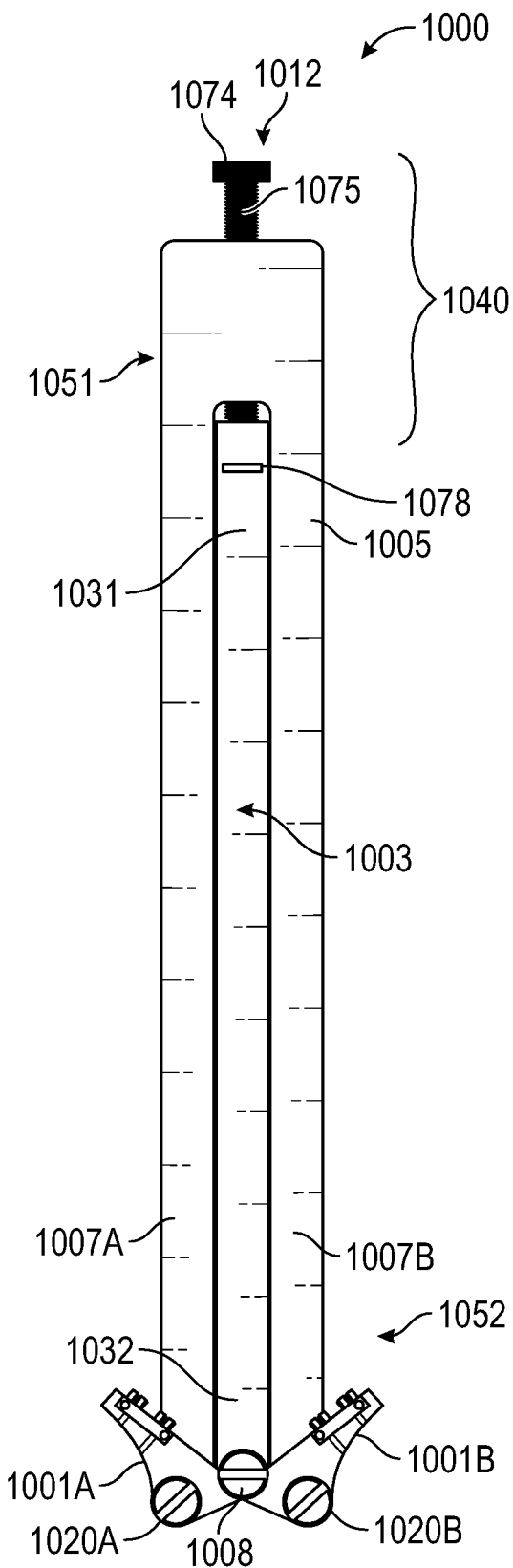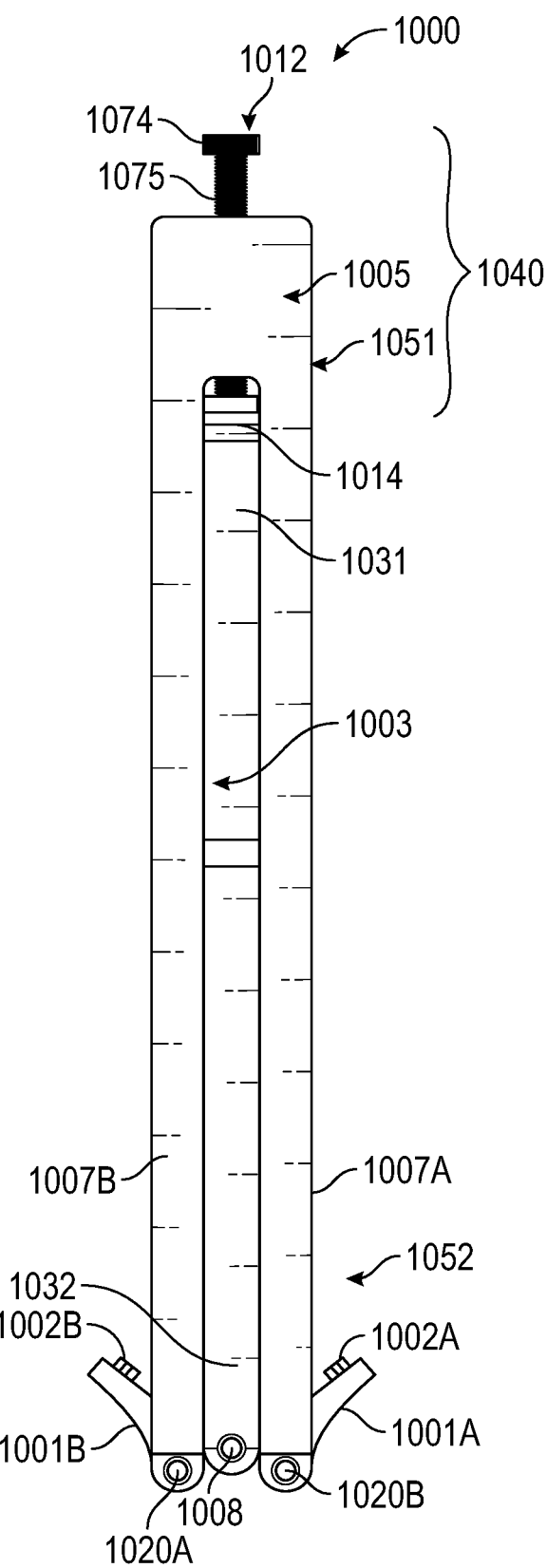
FIG. 68
FIG. 69

SYSTEMS AND METHODS FOR MICROVASCULAR ANASTOMOTIC COUPLER RING DELIVERY DEVICE

FIELD

Embodiments of the present systems, devices, and methods can be employed to deliver one or more microvascular anastomotic coupler rings to superficial surgical sites or deep surgical corridors.

BACKGROUND

Surgical fields that require microvascular anastomosis have seen a plethora of sutureless devices and techniques investigated for this purpose. Some of these devices and techniques include laser-assisted devices, staples, tissue adhesives, magnets, and ring couplers. Among microvascular surgeons in otolaryngology and reconstructive plastic surgery, the most studied microvascular anastomotic device is a ring-and-pin coupling device. This device has the advantages of ease of use, quick anastomosis times, no intraluminal foreign material, and direct intima-to-intima contact. The microvascular coupler has been described as the preferred microvascular anastomotic technique for free tissue transfer at some institutions and was initially applied to venous anastomoses but later found success in arterial anastomoses.

Although the coupler has been straightforwardly deployed in superficial end-to-end atrial bypasses, further technique development in deep tissue end-to-end coupled anastomosis is necessary for cerebrovascular use. Attempts to couple arteries in unreceptive fields like the Sylvian fissure cause cerebral cortical and vascular injury. It is these indications where the technical challenges of conventional sutured anastomosis increase and the potential utility of a sutureless coupler might also increase.

It is with these observations in mind, among others, that various aspects of the present disclosure were conceived and developed.

BRIEF DESCRIPTION OF THE DRAWINGS

Corresponding reference characters indicate corresponding elements among the view of the drawings. The headings used in the figures should not be interpreted to limit the scope of the claims.

FIG. 12 is a left side view of the device of FIG. 10;
FIG. 13 is a right side view of the device of FIG. 10;
FIG. 14 is a front view of the device of FIG. 10;
FIG. 15 is a rear view of the device of FIG. 10;
FIG. 37 is a bottom view of the device of FIG. 30;

FIG. 65 is a perspective view of a tenth embodiment of a device for a microvascular anastomosis related to FIG. 1 in an open configuration;

FIG. 66 is a perspective view of the device of FIG. 65 in a closed configuration;

FIG. 68 is a front view of the device of FIG. 65 in the open configuration;

FIG. 69 is a rear view of the device of FIG. 65 in the open configuration;

Corresponding reference characters indicate corresponding elements among the view of the drawings. The headings used in the figures do not limit the scope of the claims.

DETAILED DESCRIPTION

Microvascular anastomosis can be a versatile medical procedure for use in connecting vessels and has been applied in both venous and arterial contexts. The need to perform these procedures primarily stems from the need to revascularize areas of the brain after complex cerebral aneurysms or resection of brain tumors. A substantial portion of the microvascular anastomosis procedures performed involve either end-to-end anastomosis or end-to-side anastomosis.

End-to-end anastomosis involves connecting the ends of a vessel. The vessel is cut by the surgeon, exposing the ends of the vessel. There can either be one vessel or two vessels being connected, it depends on the specific problem that the surgeon is trying to address, and is patient specific. The procedure traditionally uses sutures with the aid of a microscope. A newer method utilizes two ring-and-pin couplers to simplify the procedure and eliminate the need for suturing together the two ends. First, both ends of the vessel are inserted into their respective ring-and-pin coupler. Next, the ends of the vessel are everted onto the pins of the coupler, such that the pins on the couplers are facing one another. This also exposes the intima of each end to one another. Last, the couplers are pushed together, thus coupling the ends of the vessel together, with intima to intima contact. The couplers are held together by the pins inserted into respective pin holes on the ring-and-pin couplers, no sutures are needed.

End-to-side anastomosis involves connecting the end of a donor vessel to a recipient vessel. This method also traditionally uses sutures to suture the end of the donor vessel to a hole found on the recipient vessel. The combination can be thought of as a "T" shape, with the top of the "T" being the recipient vessel, and the vertical line being the donor vessel. The hole is placed on the recipient vessel by the surgeon, and the end is cut into a specific shape to fit onto the hole. The vessels being connected are dependent on the procedure and the specific problem of the patient. Ring-and-pin coupler devices have not been designed for end-to-side anastomosis, but these devices have been tested in end-to-side anastomosis. First, the end of the donor vessel is inserted and everted over the pins, similar to end-to-end anastomosis, with the intima exposed. Next, a hole on the recipient vessel which has excess wall of the vessel exposed such that the wall is inserted into the ring-and-pin coupler and everted over the pins, also exposing the intima of the recipient vessel. Last, the ring-and-pin couplers are pushed together, thus coupling the donor vessel to the recipient vessel, with intima to intima contact, and without the need for sutures.

Figure 1:
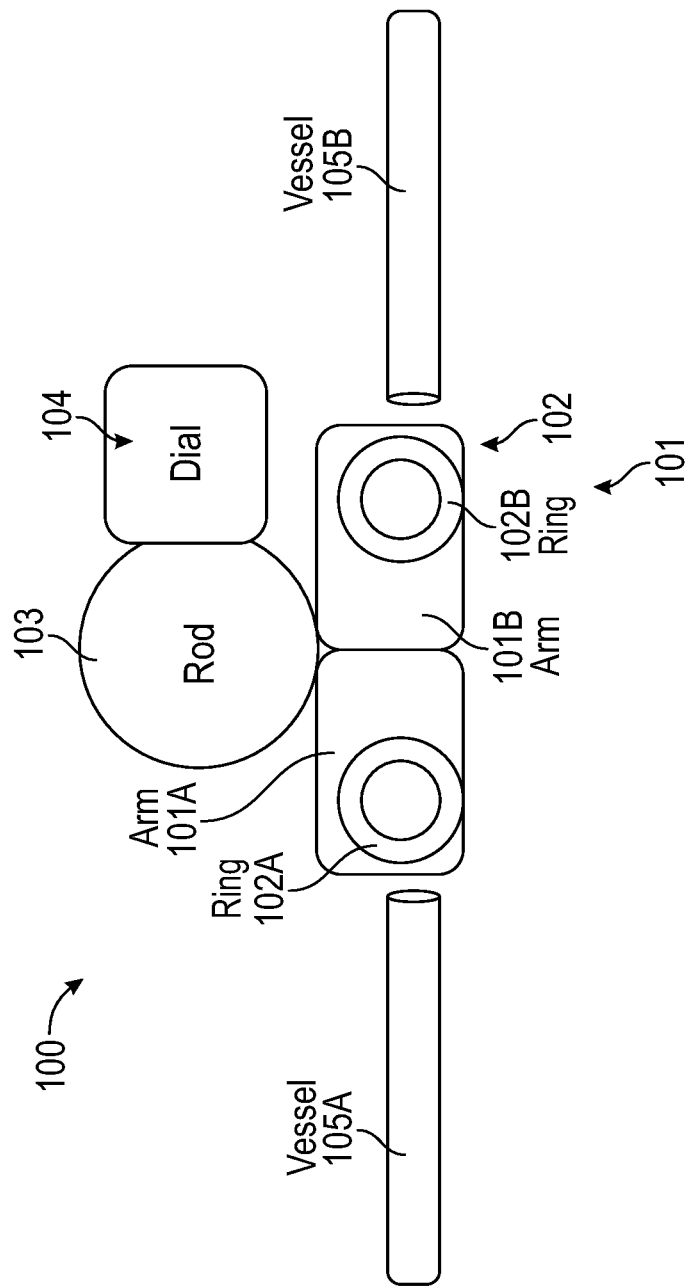
FIG. 1 is a simplified block diagram of a first embodiment of a device for microvascular anastomosis.
Figure 2:
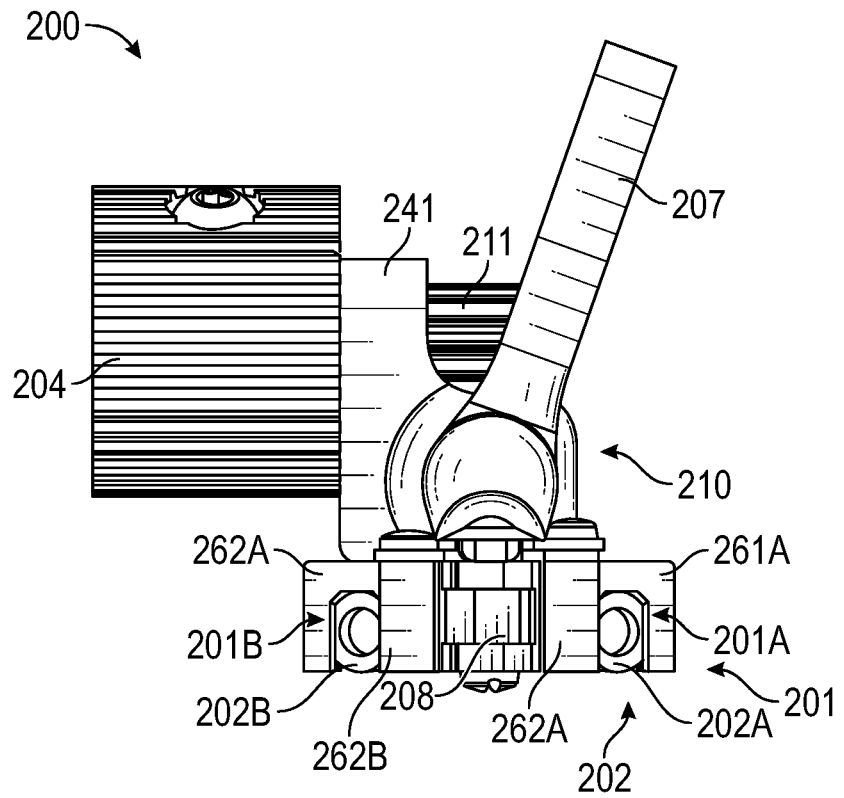
FIG. 2 is a bottom view of a second embodiment of a device for microvascular anastomosis related to FIG. 1 in an open configuration.
Figure 3:
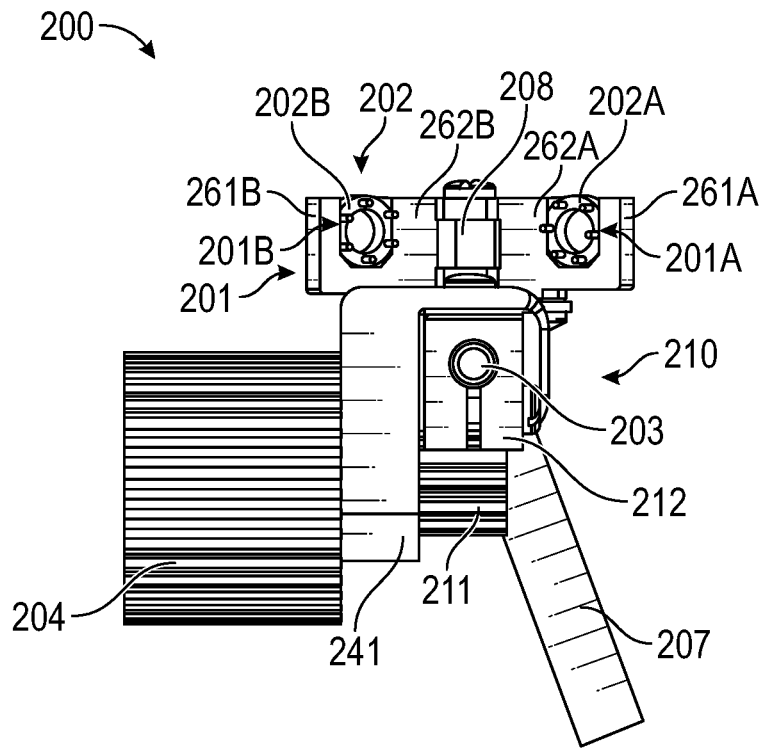
FIG. 3 is a top view of the device of FIG. 2.
Figure 4:
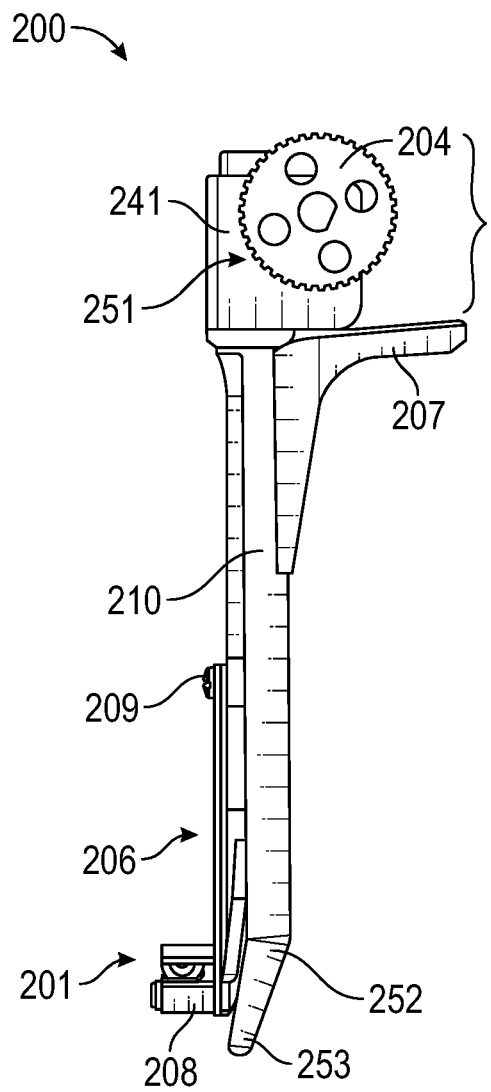
FIG. 4 is a left side view of the device of FIG. 2.
Figure 5:
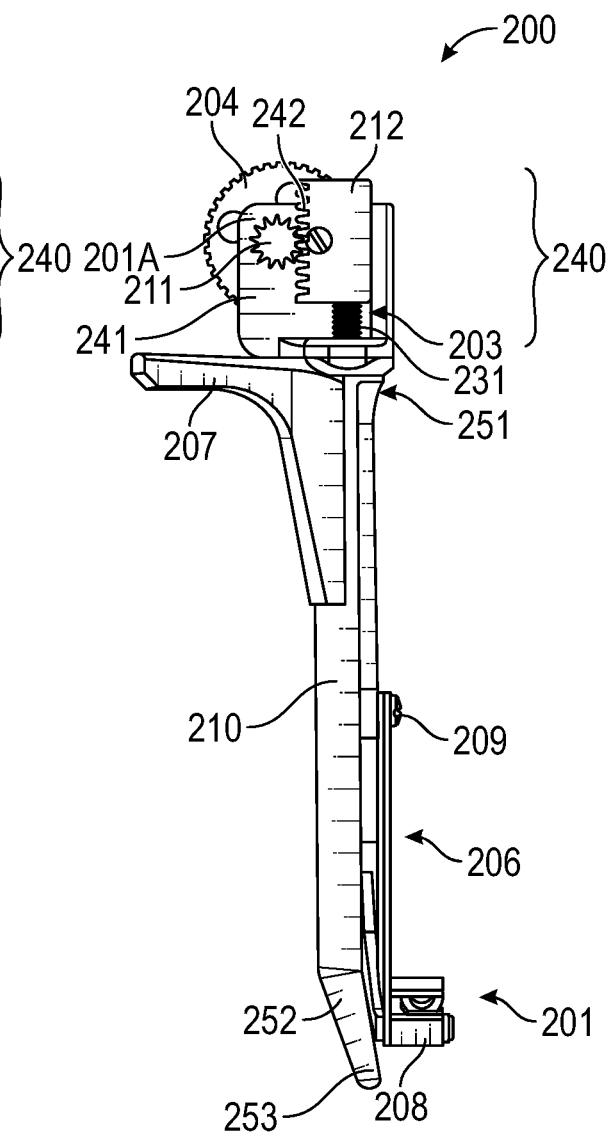
FIG. 5 is a right side view of the device of FIG. 2.
Figure 6:
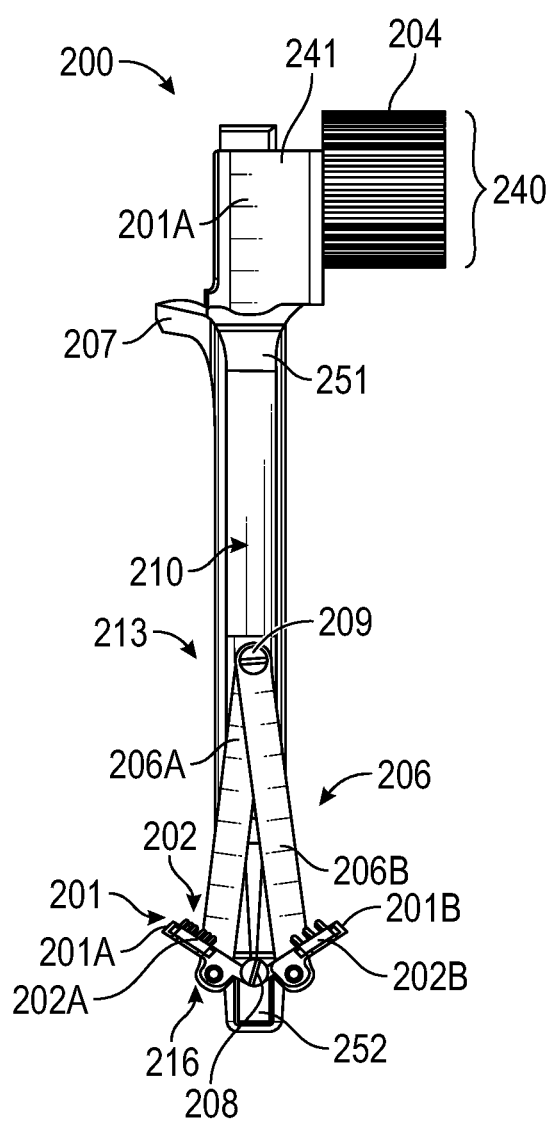
FIG. 6 is a front view of the device of FIG. 2.
Figure 7:
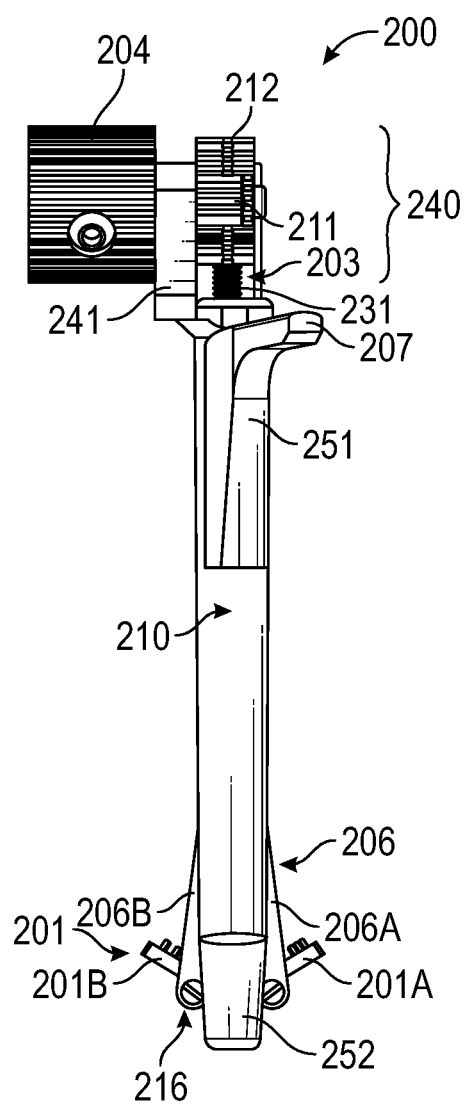
FIG. 7 is a rear view of the device of FIG. 2.
Figures 8A, 8B:
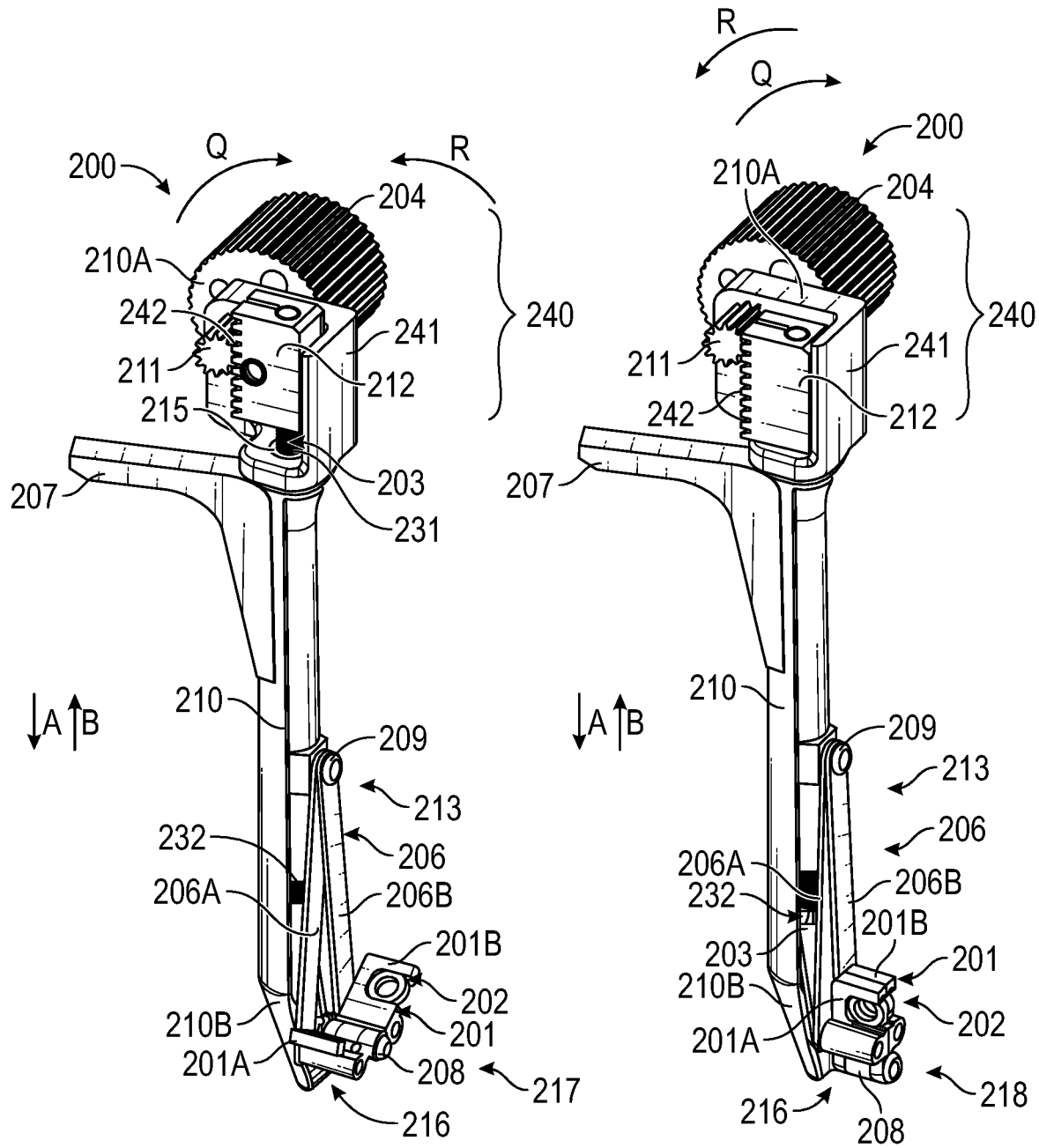
FIG. 8A is a perspective view of the device of FIG. 2 in the open configuration.
FIG. 8B is a perspective view of the device of FIG. 2 in the closed configuration.
Figure 77:
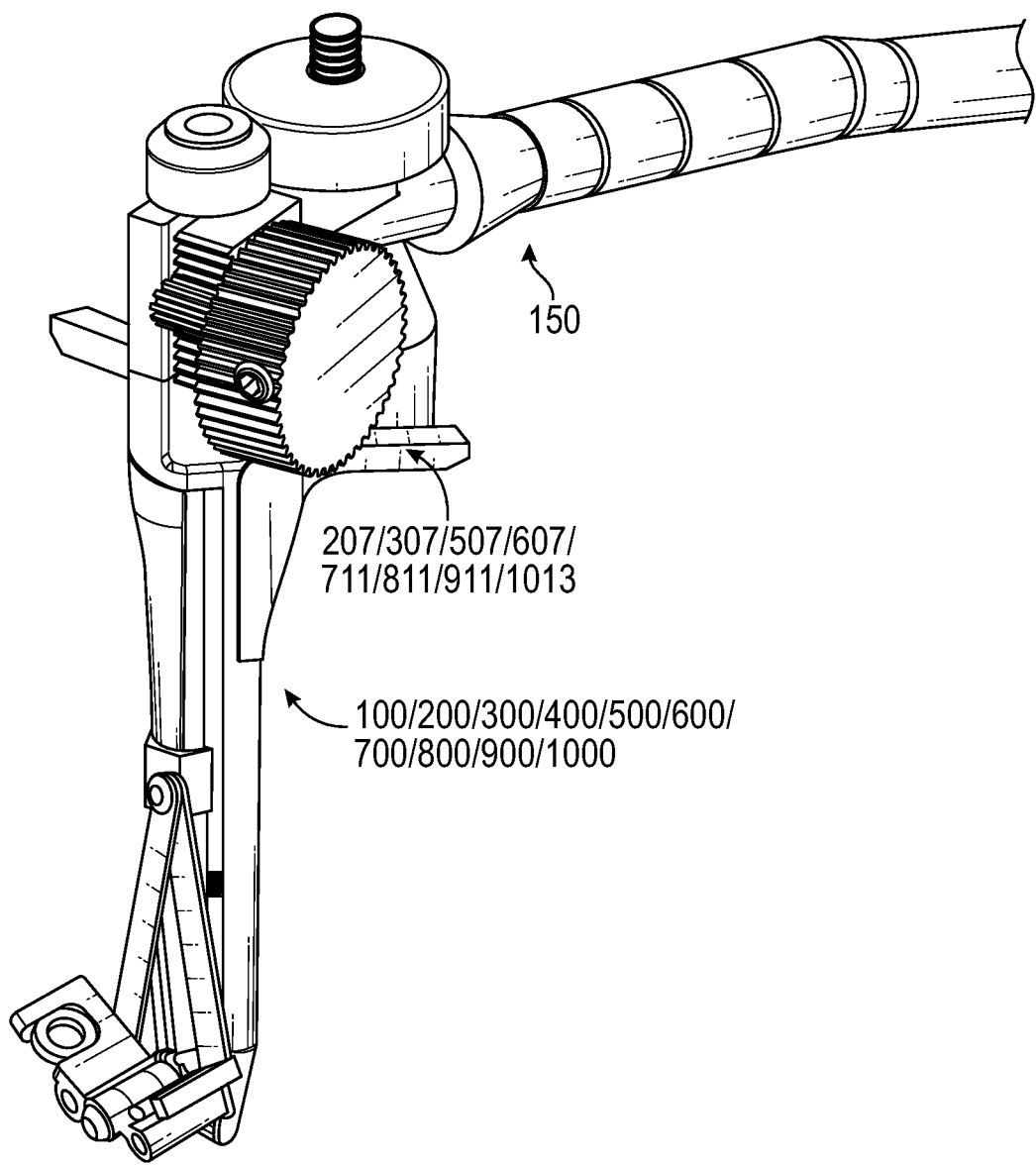
FIG. 77 is an illustration showing engagement of the device of FIG. 1, 2, 10, 22A. 25A, 27A, 30, 42, 54 or 65 with a surgical arm.

Referring to the drawings, embodiments of devices for microvascular anastomosis are illustrated and generally indicated as 100, 200, 300, 400, 500, 600, 700, 800, 900, and 1000 in FIGS. 1-77. In some embodiments, the device 100-1000 can be configured to access a vessel of a patient in a surgical corridor of approximately four centimeters below a tissue surface of the patient. In other embodiments, a device may be capable of gaining entry into a surgical corridor of more or less than four centimeters below the tissue surface. The device 100-1000 can be employed by any surgeon familiar with microvascular anastomosis.

FIG. 1 is a simplified conceptual diagram showing a coupler device 100 including a first coupler arm 101A and a second coupler arm 101B in association with a rod 103. The first coupler arm 101A and the second coupler arm 101B are each configured to receive a respective portion 102A and 102B of a coupler ring 102. Blood vessels 105 coupled to each respective portion 102A and 102B of the coupler ring 102 can be connected by coupling each portion 102A and 102B of the coupler ring 102 together while the blood vessels 105 are attached. The first and second coupler arms 101A and 101B are configured to couple the first portion 102A and the second portion 102B of the coupler ring 102 together as the first and second coupler arms 101A and 101B are drawn together, as will be further discussed herein. The rod 103 is operable for actuation in a first axial direction (not shown) such that the first and second coupler arms 101A and 101B are drawn together. In some embodiments, the coupler device 100 includes an actuator 104 in association with the rod 103 that enables actuation of the rod 103 in the first axial direction. In some embodiments the actuator 104 includes a rack-and-pinion arrangement, or a tensioned arrangement, by way of example. In some embodiments, the body may include a surgical mount. By way of example only, the surgical mount may be configured and arranged to engage with a surgical arm. The surgical arm may be mounted to a bed found in a neurosurgical operating room.

In some embodiments, the device 100 may be capable of gaining entry into a surgical corridor of approximately four centimeters below a tissue surface of a patient. In other embodiments, the device 100 may be capable of gaining entry into a surgical corridor of more or less than four centimeters below the tissue surface. Furthermore, in some embodiments, the first and second coupler arms 101A and 101B can be configured and arranged to provide a view angle of the first and second coupler arms 101A and 101B within the surgical corridor. Moreover, the first and second coupler arms 101A and 101B may be configured and arranged to be substantially positioned at an angle relative to the body, wherein the angle relative to the body is substantially a right angle. Additionally, in some embodiments, the plurality of arms may be configured and arranged to access a vessel disposed at least partially within the surgical corridor. In some embodiments, the first and second coupler arms 101A and 101B may be configured and arranged to maintain the vessel in a directional plane.

When the first and second coupler arms 101A and 101B are reconfigured into the closed configuration, this may connect the ends of the vessel through the connection of the plurality of ring-and-pin couplers. The plurality of ring-and-pin couplers may connect through the pins and pin receptacles found on each ring-and-pin coupler. The plurality of ring-and-pin couplers can now be decoupled from their respective arm 101A and 101B.

FIGS. 2-9 illustrate a first embodiment of a coupler device, designated 200, having a first coupler arm 201A and a second coupler arm 201B in association with a rod 203. The first coupler arm 201A and the second coupler arm 201B are each configured to receive a respective portion 202A and 202B of a coupler ring 202. The rod 203 defines a proximal portion 231 and a distal portion 232 associated with the first and second coupler arms 201A and 201B. The rod 203 is operable for actuation in a first axial direction A by an actuator 240 in association with the proximal portion 231 of the rod 203. As the rod 203 is actuated in the first axial direction A, the first and second coupler arms 201A and 201B and consequently the first and second portions 202A and 202B of the coupler ring 202 are drawn together. This arrangement enables the first and second coupler arms 201A and 201B to assume an open configuration or a closed configuration. The coupler device 200 further defines an elongated body 210 including a proximal portion 251, a distal portion 252, and a channel 215 defined axially through the elongated body 210 for receipt of the rod 203. The proximal portion 251 of the elongated body 210 is configured to house or otherwise provide support for the actuator 240 and the proximal portion 231 of the rod 203.

Figure 9A:
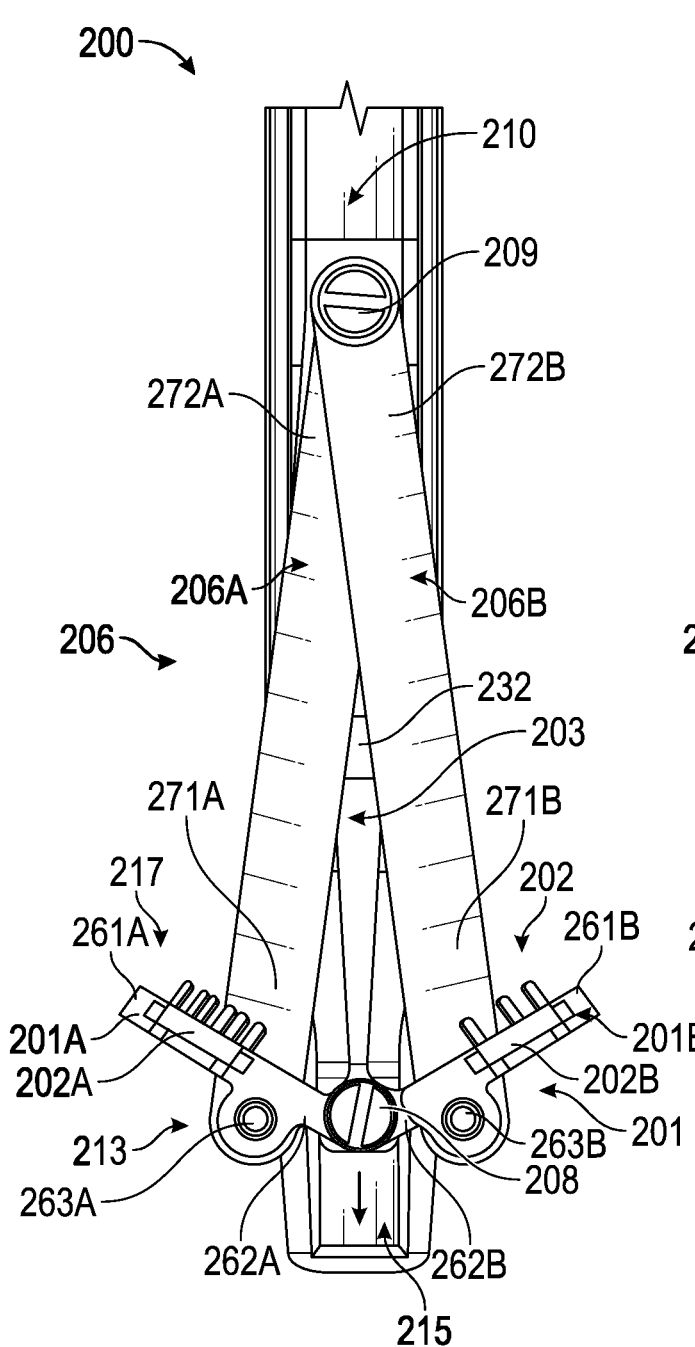
FIG. 9A is an enlarged front view of the device of FIG. 2 in the open configuration.
Figure 9B:
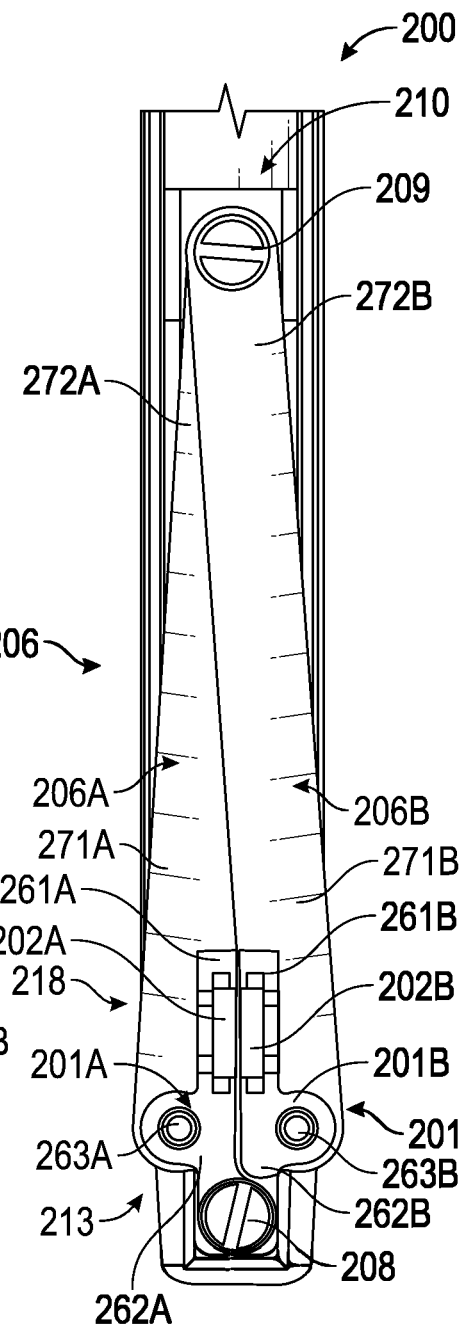
FIG. 9B is an enlarged front view of the device of FIG. 2 in the closed configuration.
Figure 10:
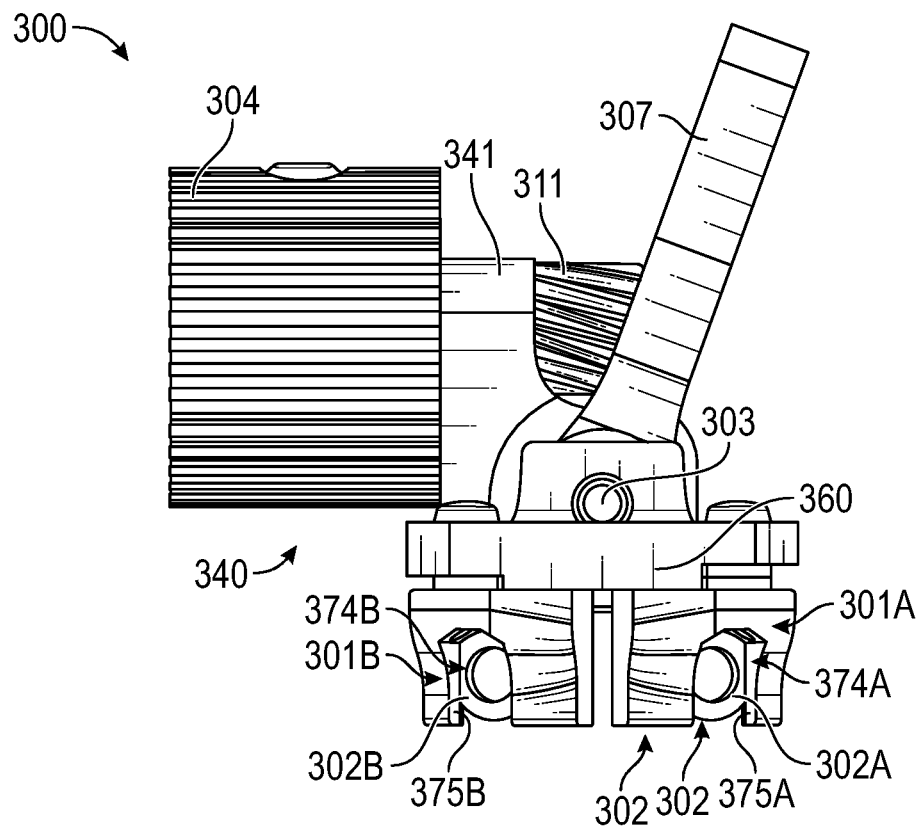
FIG. 10 is a bottom view of a third embodiment of a device for microvascular anastomosis related to FIG. 1.
Figure 11:
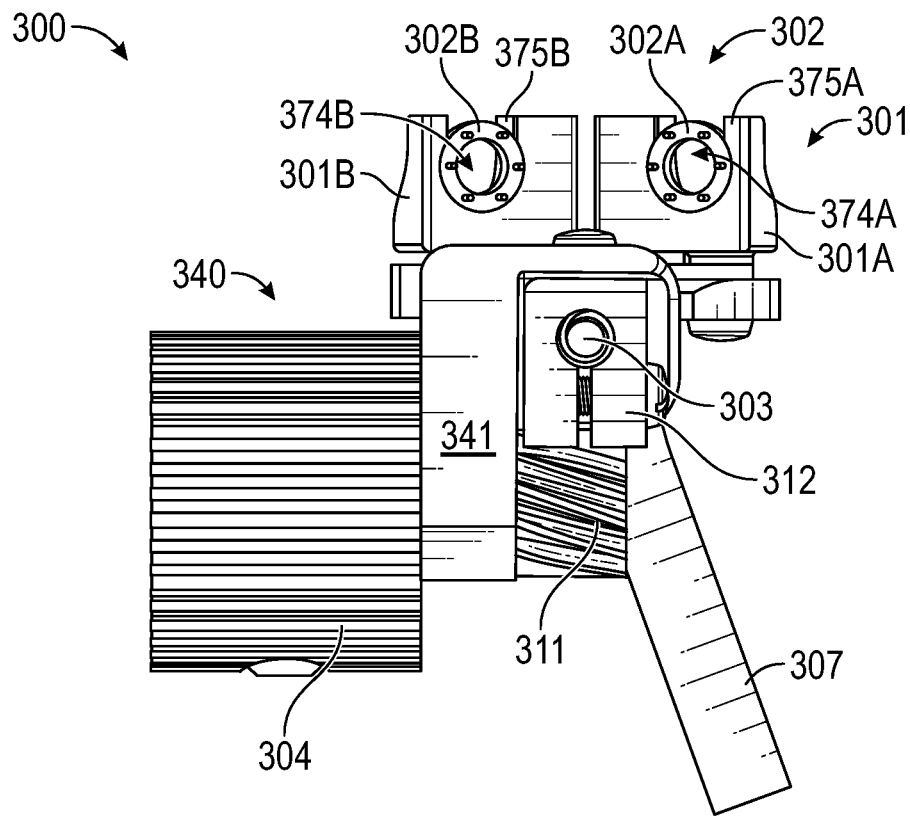
FIG. 11 is a top view of the device of FIG. 10.
Figure 16A:
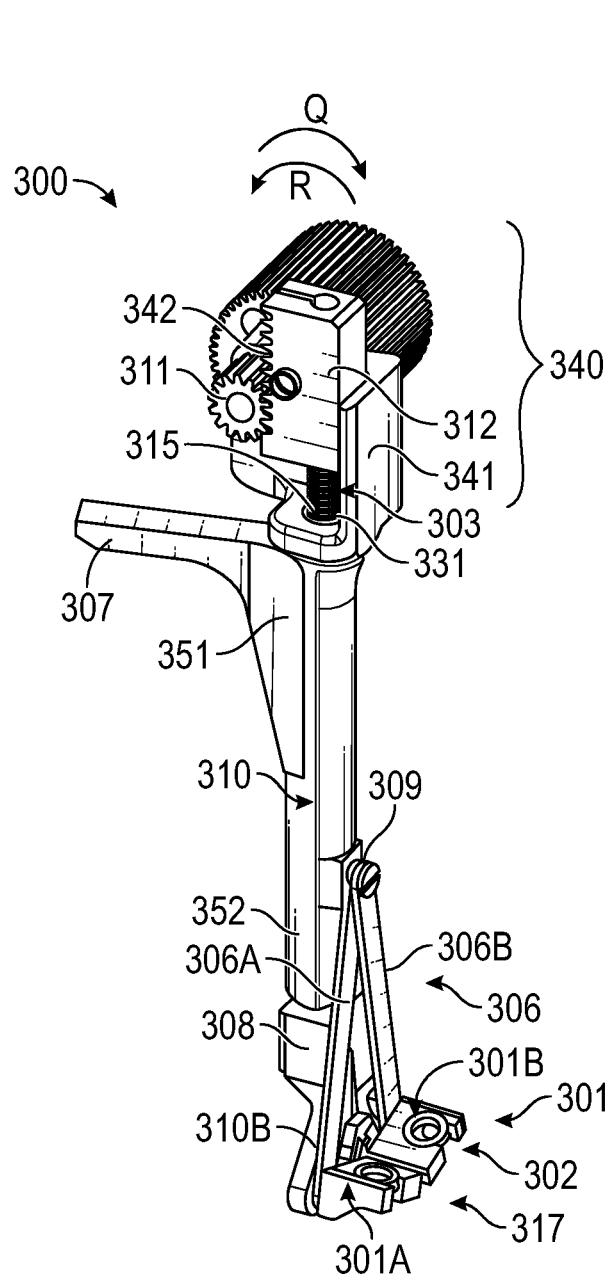
FIG. 16A is a perspective view of the device of FIG. 10 in an open configuration.
Figure 16B:
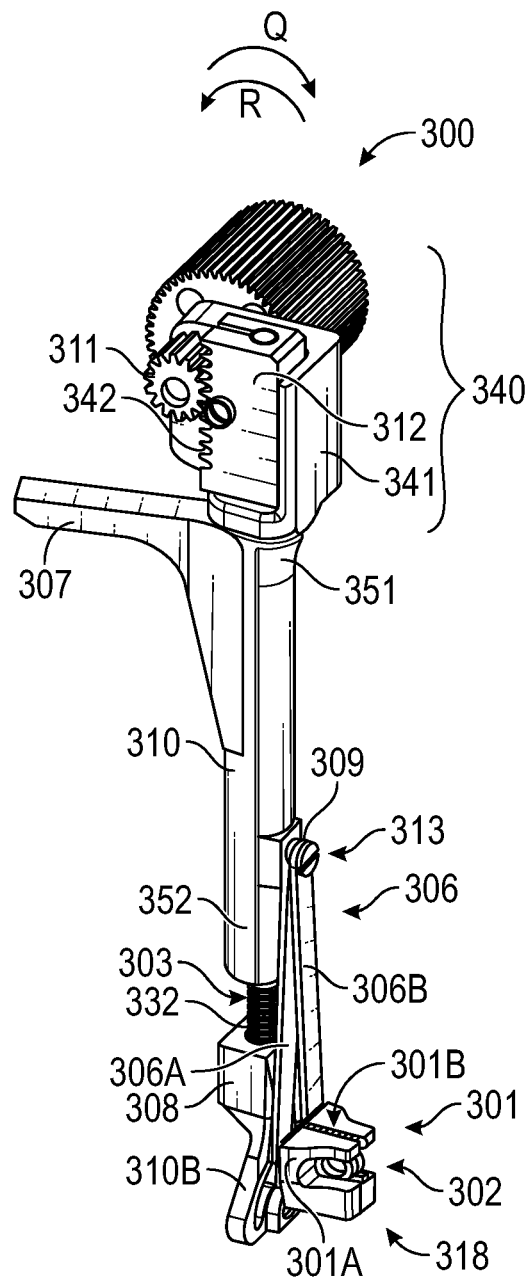
FIG. 16B is a perspective view of the device of FIG. 10 in a closed configuration.

Referring directly to FIGS. 9A and 9B, the first coupler arm 201A and the second coupler arm 201B of the pair of coupler arms 201 are joined at the distal portion 232 of the rod 203 by a lower post 208. In particular, the first coupler arm 201A and the second coupler arm 201B each include a respective free end 261A and 261B and a pivotable end 262A and 262B. The pivotable ends 261A and 261B of each coupler arm 201A and 201B are joined by and rotatable about the lower post 208. The coupler arms 201A and 201B are operable to assume an open configuration as shown specifically in FIG. 9A, and a closed configuration as shown specifically in FIG. 9B. The first coupler arm 201A includes a first intermediate post 263A in association with a distal portion 271A of a first support arm 206A of a pair of support arms 206. Similarly, the second coupler arm 201B includes a second intermediate post 263B in association with a distal portion 271B of a second support arm 206B of a pair of support arms 206. The first and second support arms 206A and 206B each include a proximal portion 272A and 272B that are pivotably coupled to the elongated body by an upper post 209, as shown. The elongated body 210 defines a tapered portion 253 at a lower portion 254 of the channel 215. During actuation of the rod 203 in the first axial direction A, the lower post 208 is guided downward through the lower portion 254 of the channel 215 as the rod 203 is forced downward in the first axial direction A. This motion forces the pivotable ends 261A and 261B of each coupler arm 206A and 206B downward. As the pivotable ends 261A and 261B of each coupler arm 206A and 206B are connected by the lower post 208, the free ends 261A and 261B of each coupler arm 206A and 206B are drawn together into the closed configuration as the pivotable ends 261A and 261B are forced downward in the first axial direction A. This motion is guided by the first and second support arms 206A and 206B which guide the first and second intermediate posts 263A and 263B associated with each coupler arm 206A and 206B together as shown between FIGS. 9A and 9B.

Each respective coupler arm 206A and 206B includes a receptacle 264A and 264B including an open portion 265A and 265B configured to receive a portion 202A or 202B of a ring-and-pin coupler 202. Each respective portion 202A or 202B of the ring-and-pin coupler 202 can be removed from the respective coupler arm 206A and 206B through the open portion 265A and 265B of the coupler arm 206A and 206B.

Referring to FIGS. 4, 5, 8A and 8B, in some embodiments the actuator 240 includes a rack-and-pinion arrangement to actuate the rod 203 in the first axial direction A. In particular, the proximal portion 231 of the rod 203 includes a rack 212 defining a plurality of teeth 242 for engagement with a pinion 211 associated with the proximal portion 231 of the elongated body 210. In a primary embodiment, the pinion 211 is rotatable by the dial 204, however in some embodiments, the pinion 211 is rotatable by another means such as a crank mechanism. The proximal portion 251 of the elongated body 210 can further define an actuator housing 241 that receives the pinion 211 and dial 204 as shown. In some embodiments, the elongated body 210 further includes a grip element 207 in association with the actuator housing 241 that enables a practitioner to wield and stabilize the device 200 when coupling vessels together using the device 200.

To close the coupler arms 206, the pinion 211 is rotated in a first rotational direction Q, the associated rack 212 is driven in the first axial direction A along with the remainder of the rod 203 associated with the rack 212. During actuation of the rod 203 in the first axial direction A by the pinion 211, the lower post 208 is guided downward through the lower portion 254 of the channel 215 as the rod 203 is forced downward in the first axial direction A. This motion forces each coupler arm 206A and 206B together in the closed configuration. Similarly, to open the coupler arms 206, the pinion 211 is rotated in an opposite second rotational direction R, the associated rack 212 is driven in a second axial direction B along with the remainder of the rod 203 associated with the rack 212. During actuation of the rod 203 in the second axial direction B by the pinion 211, the lower post 208 is guided upward through the lower portion 254 of the channel 215 as the rod 203 is forced upward in the second axial direction B. This motion forces each coupler arm 206A and 206B apart to the open configuration.

Figure 18:
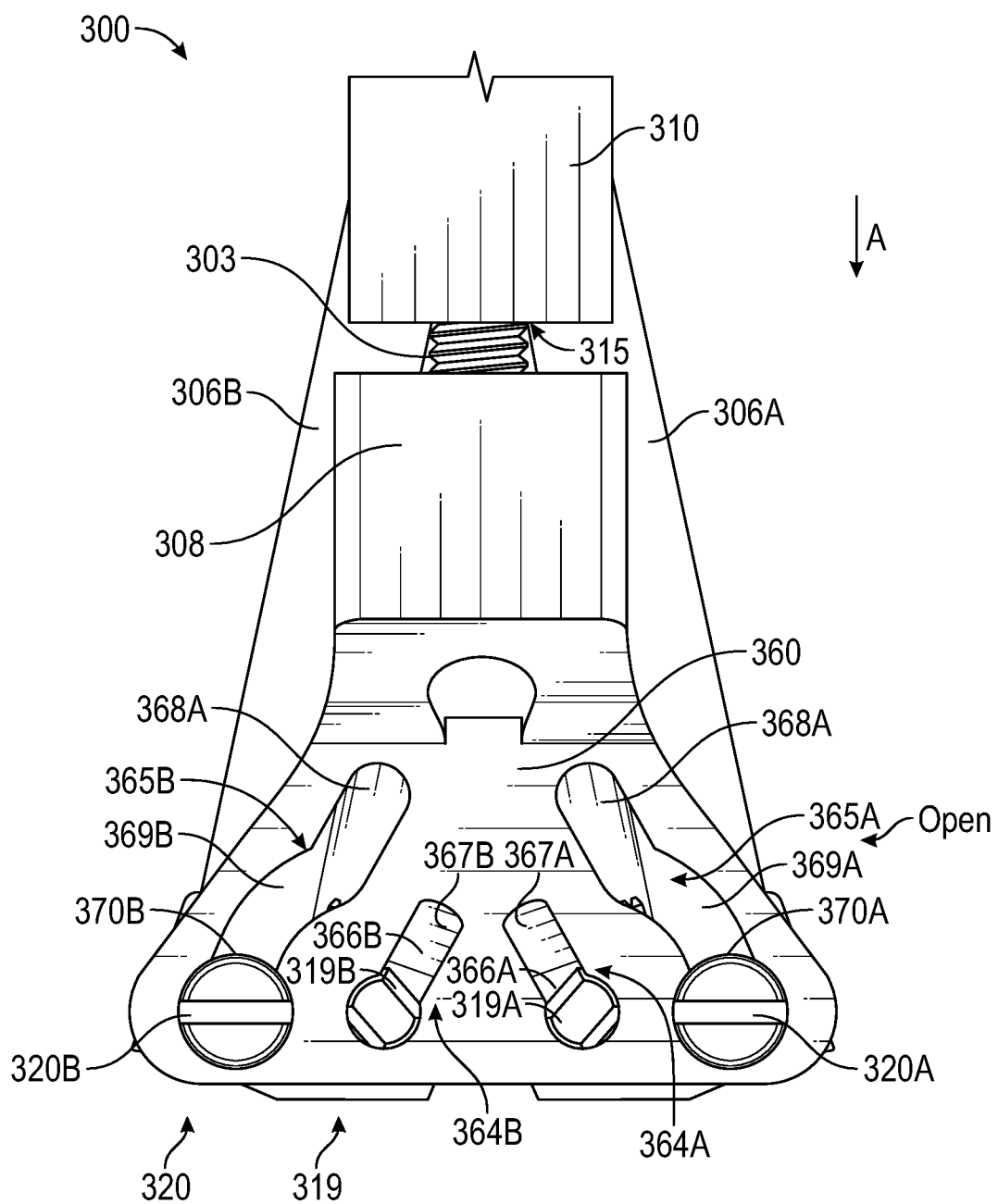
FIG. 18 is an enlarged rear view of the device of FIG. 10 in an open configuration.
Figure 19:
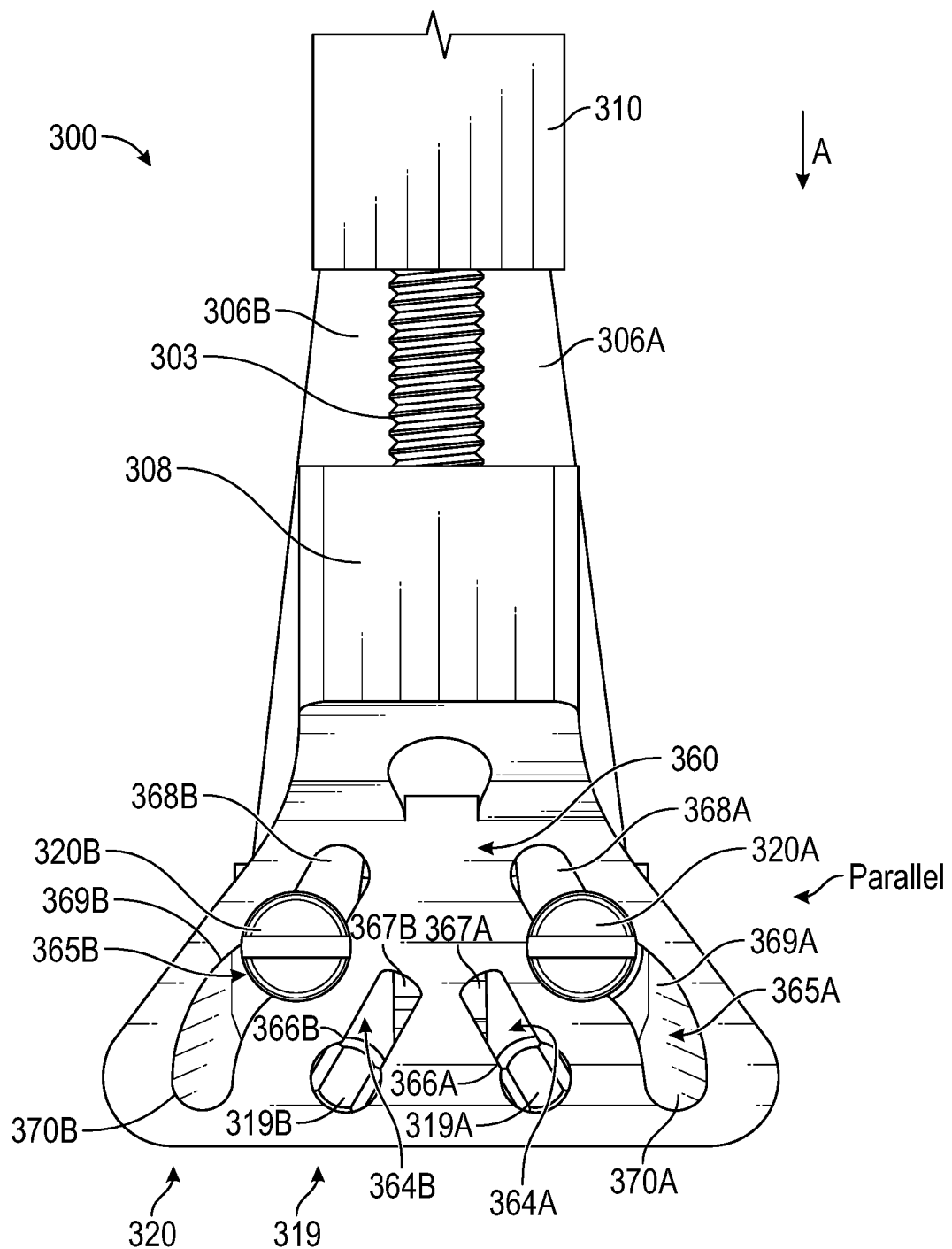
FIG. 19 is an enlarged rear view of the device of FIG. 10 in a parallel configuration.
Figure 20:
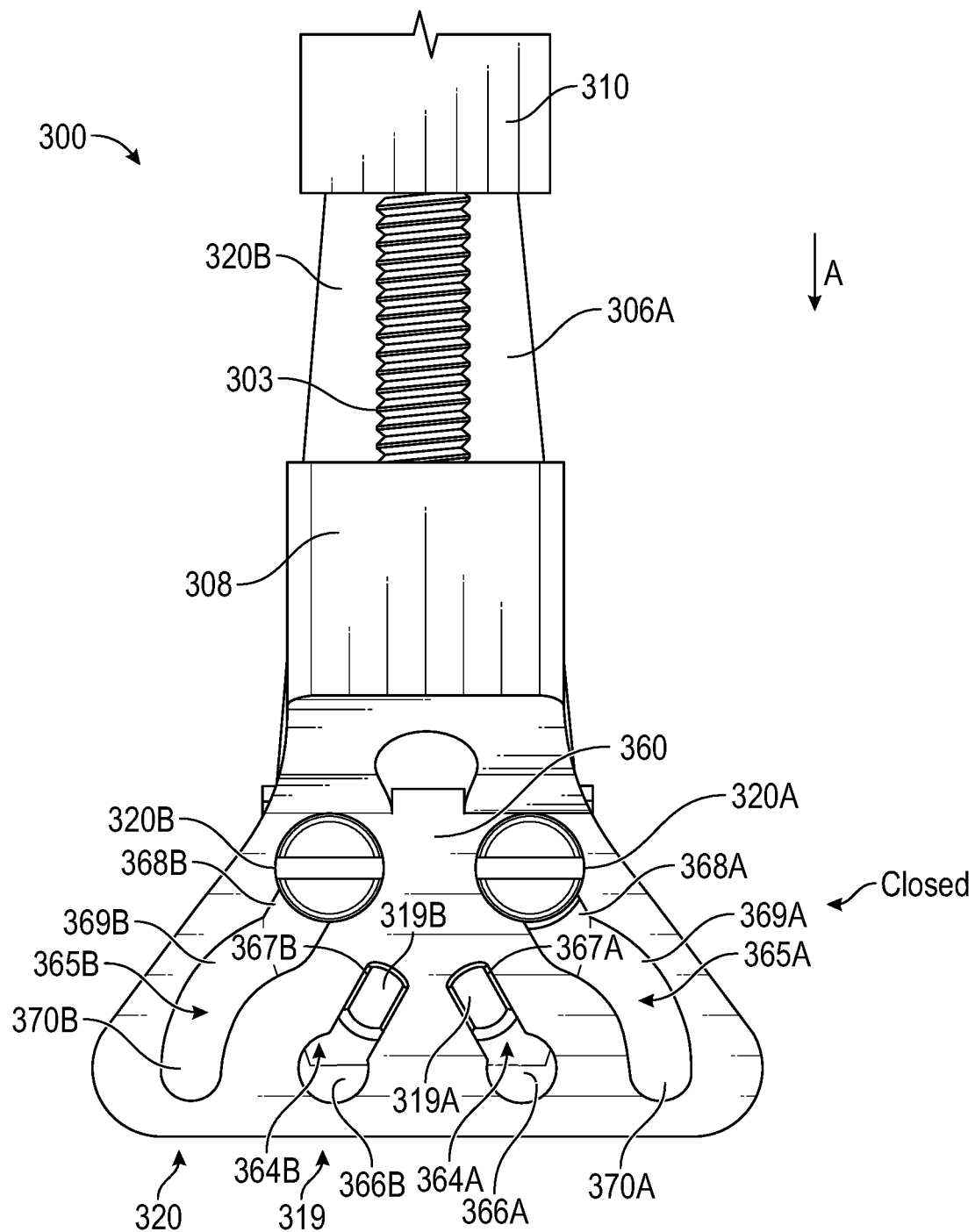
FIG. 20 is an enlarged rear view of the device of FIG. 10 in a closed configuration.
Figure 21A:
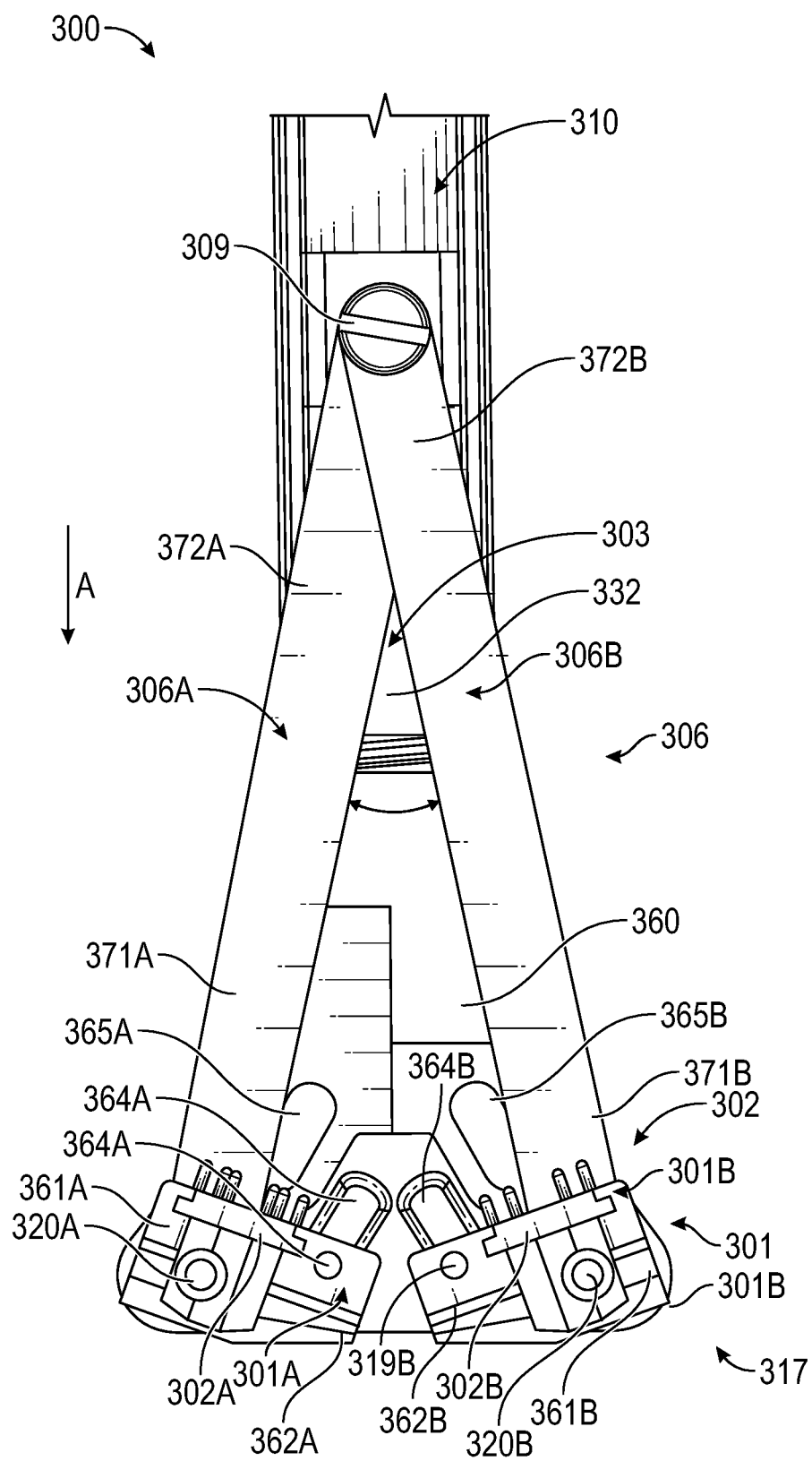
FIG. 21A is an enlarged front view of the device of FIG. 10 in an open configuration.
Figure 21B:
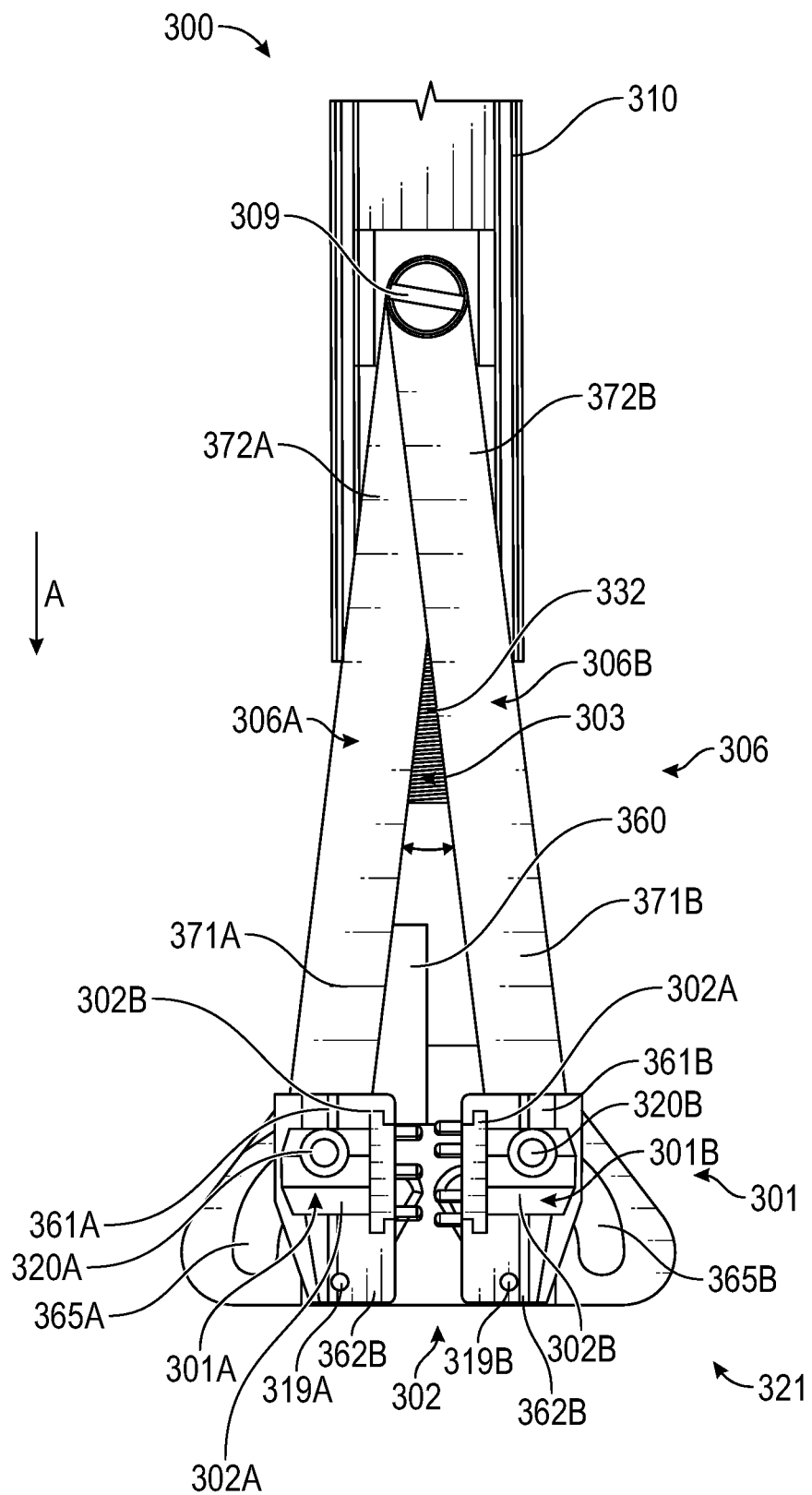
FIG. 21B is an enlarged front view of the device of FIG. 10 in a parallel configuration.
Figure 21C:
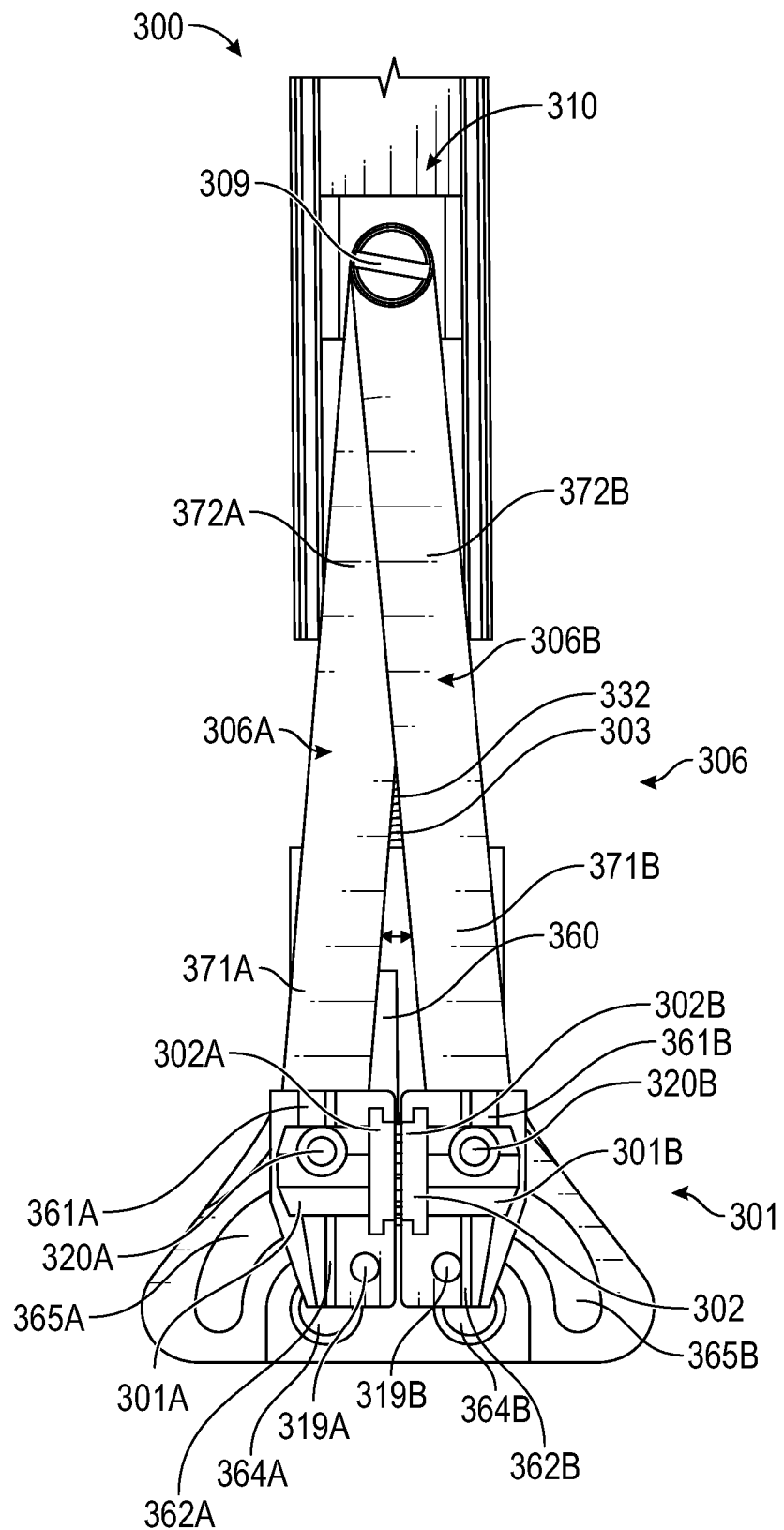
FIG. 21C is an enlarged front view of the device of FIG. 10 in a closed configuration.

FIGS. 10-21C illustrate a second embodiment of a coupler device, designated 300, having a first coupler arm 301A and a second coupler arm 301B in association with a rod 303. The first coupler arm 301A and the second coupler arm 301B are each configured to receive a respective portion 302A and 302B of a coupler ring 302. The rod 303 defines a proximal portion 331 and a distal portion 332 associated with the first and second coupler arms 301A and 301B. The rod 303 is operable for actuation in a first axial direction A by an actuator 340 in association with the proximal portion 331 of the rod 303. As the rod 303 is actuated in the first axial direction A, the first and second coupler arms 301A and 301B and consequently the first and second portions 302A and 302B of the coupler ring 302 are drawn together. The coupler device 300 further defines an elongated body 310 including a proximal portion 351, a distal portion 352, and a channel 315 defined axially through the elongated body 310 for receipt of the rod 303. The proximal portion 351 of the elongated body 310 is configured to house or otherwise provide support for the actuator 340 and the proximal portion 331 of the rod 303. In some embodiments, the coupler device 300 includes a backplate 360 that enables the first and second coupler arms 301A and 301B to assume one of an open configuration as shown in FIGS. 18 and 21A, a parallel configuration as shown in FIGS. 19 and 21B, and a closed configuration as shown in FIGS. 20 and 21C.

Referring directly to FIGS. 14-21C, the first coupler arm 301A and the second coupler arm 301B of the pair of coupler arms 301 are each mounted at the backplate 360 of the distal portion 352 of the elongated body 310 of the rod 303 by a respective first and second lower post 319A and 319B. The backplate 360 includes a plurality of cams defining a first inner cam 364A and a first outer cam 365A associated with the first coupler arm 301A and a first support arm 306A. Similarly, the backplate 360 includes a second inner cam 364B and a second outer cam 365B associated with the second coupler arm 301B and a second support arm 306B.

The first coupler arm 301A and the second coupler arm 301B each include a free end 361A and 361B and a pivotable end 362A and 362B. The pivotable ends 362A and 362B of each coupler arm 301A and 301B are joined by and rotatable about a respective first and second lower post 319A and 319B. The first lower post 319A is positionable at a first extreme position or a second extreme position within the first inner cam 364A of the backplate 360. Likewise, the second lower post 319A is positionable at a first extreme position or a second extreme position within the second inner cam 364B of the backplate 360.

The first coupler arm 301A includes a first intermediate post 320A positionable at a first extreme position, a parallel position, or a second extreme position within the first outer cam 320A. The first intermediate post 320A couples the first coupler arm 301A with the backplate 360 of the elongated body 310. Similarly, the second coupler arm 301B includes a second intermediate post 320B positionable at a first extreme position, a parallel position, or a second extreme position within the second outer cam 320B. The second intermediate post 320B couples the second coupler arm 301B with the backplate 360 of the elongated body 310.

In the open configuration shown in FIGS. 18 and 21A, the first and second coupler arms 301A and 301B are in a non-parallel arrangement relative to one another. In the open configuration, the first and second lower posts 319A and 319B occupy a lower portion 366A and 366B of each respective inner cam 364A and 364B. Further, in the open configuration, the first and second intermediate posts 320A and 320B occupy a lower portion 370A and 370B of each respective outer cam 365A and 365B. In the parallel configuration shown in FIGS. 19 and 21B, the first and second coupler arms 301A and 301B are in a parallel arrangement relative to one another, but are not drawn together in the closed position. In the parallel configuration, the first and second lower posts 319A and 319B occupy the lower portion 366A and 366B of each respective inner cam 364A and 364B. Further, in the parallel configuration, the first and second intermediate posts 320A and 320B occupy an intermediate portion 369A and 369B of each respective outer cam 365A and 365B. The intermediate portions 369A and 369B of the first and second outer cams 365A and 365B each define a curve that forces the first and second coupler arms 301A and 301B to align with one another in a parallel arrangement. In the closed configuration shown in FIGS. 20 and 21C, the first and second coupler arms 301A and 301B are in a parallel arrangement relative to one another and are also drawn together such that the first and second portions 302A and 302B of the coupler ring 302 are coupled together. In the closed configuration, the first and second lower posts 319A and 319B occupy a respective upper portion 367A and 367B of each respective inner cam 364A and 364B. Further, in the open configuration, the first and second intermediate posts 320A and 320B occupy a respective upper portion 368A and 368B of each respective outer cam 365A and 365B.

The first and second support arms 306A and 306B each include a proximal portion 372A and 372B that are pivotably coupled to the elongated body 310 by an upper post 309, as shown. Further, the first and second support arms 306A and 306B each include a respective distal portion 371A and 371B configured to couple with respective first and second coupler arms 301A and 301B. During actuation of the rod 303 in the first axial direction A, the first lower post 319B and the second lower post 319B are guided downward to occupy the lower portion 366A and 366B of each respective inner cam 364A and 364B as the rod 303 is forced downward in the first axial direction A. This motion forces the pivotable ends 362A and 362B of each coupler arm 301A and 301B downward. As the pivotable ends 362A and 362B of each coupler arm 301A and 301B are connected by the lower post 208, the free ends 361A and 361B of each coupler arm 301A and 301B are drawn together firstly into the parallel configuration, and then the closed position as the pivotable ends 362A and 362B are forced downward in the first axial direction A. This motion is guided by the first and second support arms 306A and 306B which guide the first and second intermediate posts 320A and 320B associated with each coupler arm 301A and 301B together as shown in FIGS. 21A-21C.

Figure 17:
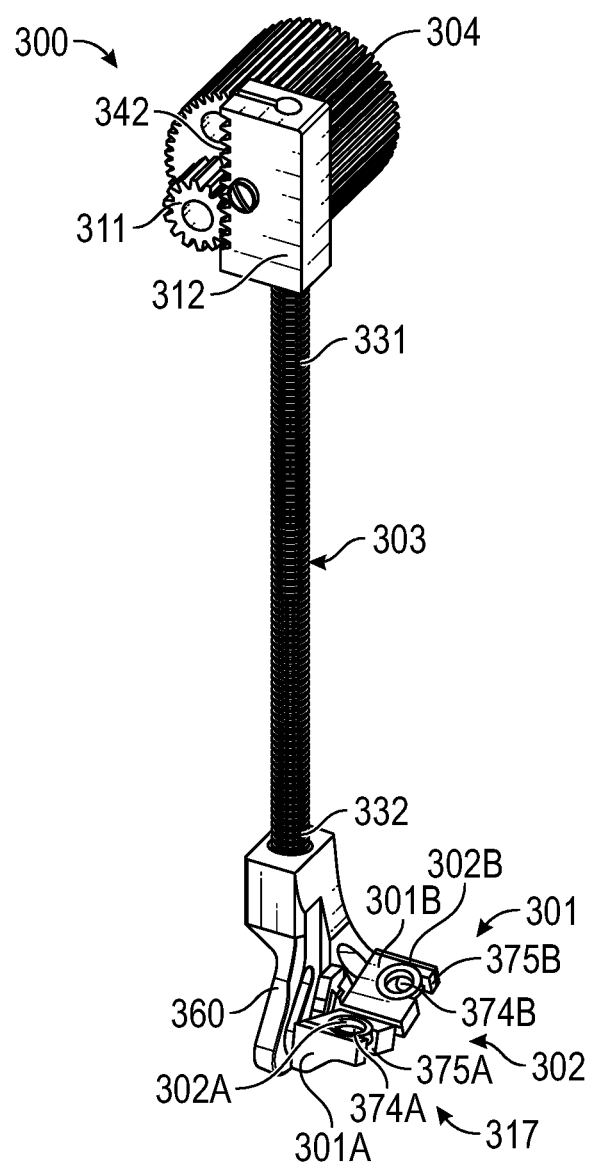
FIG. 17 is a perspective view of the device of FIG. 10 to highlight the rod.

Referring specifically to FIG. 17, each respective coupler arm 301A and 301B includes a receptacle 374A and 374B including an open portion 375A and 375B configured to receive a portion 302A or 302B of a ring-and-pin coupler 302. Each respective portion 302A or 302B of the ring-and-pin coupler 302 can be removed from the respective coupler arm 301A and 301B through the open portion 375A and 375B of the coupler arm 301A and 301B.

Referring to FIGS. 10-17, in some embodiments the actuator 340 includes a rack-and-pinion arrangement to actuate the rod 303 in the first axial direction A. In particular, the proximal portion 331 of the rod 303 includes a rack 312 defining a plurality of teeth 342 for engagement with a pinion 311 associated with the proximal portion 351 of the elongated body 310. In a primary embodiment, the pinion 311 is rotatable by the dial 304, however in some embodiments, the pinion 311 is rotatable by another means such as a crank mechanism. The proximal portion 351 of the elongated body 310 can further define an actuator housing 341 that receives the pinion 311 and dial 304 as shown. In some embodiments, the elongated body 310 further includes one or more grip elements 307 in association with the actuator housing 341 that enables a practitioner to comfortably wield and stabilize the device 300 when coupling vessels together using the device 300.

To close the coupler arms 301, the pinion 311 is rotated in a first rotational direction Q, the associated rack 312 is driven in the first axial direction A along with the remainder of the rod 303 associated with the rack 312. During actuation of the rod 303 in the first axial direction A by the pinion 311, the first and second lower posts 319A and 319B are guided downwards to occupy the lower portion 366A and 366B of each respective inner cam 364A and 364B as the rod 303 is forced downward in the first axial direction A. This motion forces the pivotable ends 362A and 362B of each coupler arm 301A and 301B downward to the parallel configuration, then to the closed configuration. Similarly, to open the coupler arms 301, the pinion 311 is rotated in an opposite second rotational direction R, the associated rack 312 is driven in a second axial direction B along with the remainder of the rod 303 associated with the rack 312. During actuation of the rod 303 in the second axial direction B by the pinion 311, the lower posts 319A and 319B are guided to occupy the lower portion 366A and 366B of each respective inner cam 364A and 364B as the rod 303 is forced upward in the second axial direction B. This motion forces each coupler arm 301A and 301B apart to the parallel configuration, and then to the open configuration.

FIGS. 22A-24 illustrate a third embodiment of a coupler device, designated 400, having a first coupler arm 401A and a second coupler arm 401B in association with a rod 403 by a lead nut 420 that is rotatable about the rod 403. The first coupler arm 401A and the second coupler arm 401B are each configured to receive a respective portion of a coupler ring (not shown, but analogous to previously described coupler rings 102, 202 and 302). The rod 403 defines a proximal portion 431 and a distal portion 432 associated with the first and second coupler arms 401A and 401B. The lead nut 420 is operable for actuation in a first axial direction A by rotation of the rod 403 by an actuator 440 in association with the proximal portion 431 of the rod 403. As shown, the rod 403 defines a threaded exterior surface 433 configured for engagement with a threaded interior surface (not shown) of the lead nut 420. As the lead nut 420 is actuated in the first axial direction A, the first and second coupler arms 401A and 401B and consequently the first and second portions 402A and 402B of the coupler ring 402 are drawn together. This arrangement enables the first and second coupler arms 401A and 401B to assume an open configuration or a closed configuration. The coupler device 400 further defines an elongated body 410 including a proximal portion 451, a distal portion 452, and a channel 415 defined axially through the elongated body 410 for receipt of the rod 403. The proximal portion 451 of the elongated body 410 is configured to house or otherwise provide support for the actuator 440 and the distal portion 432 of the rod 403.

Figures 22A, 22B:
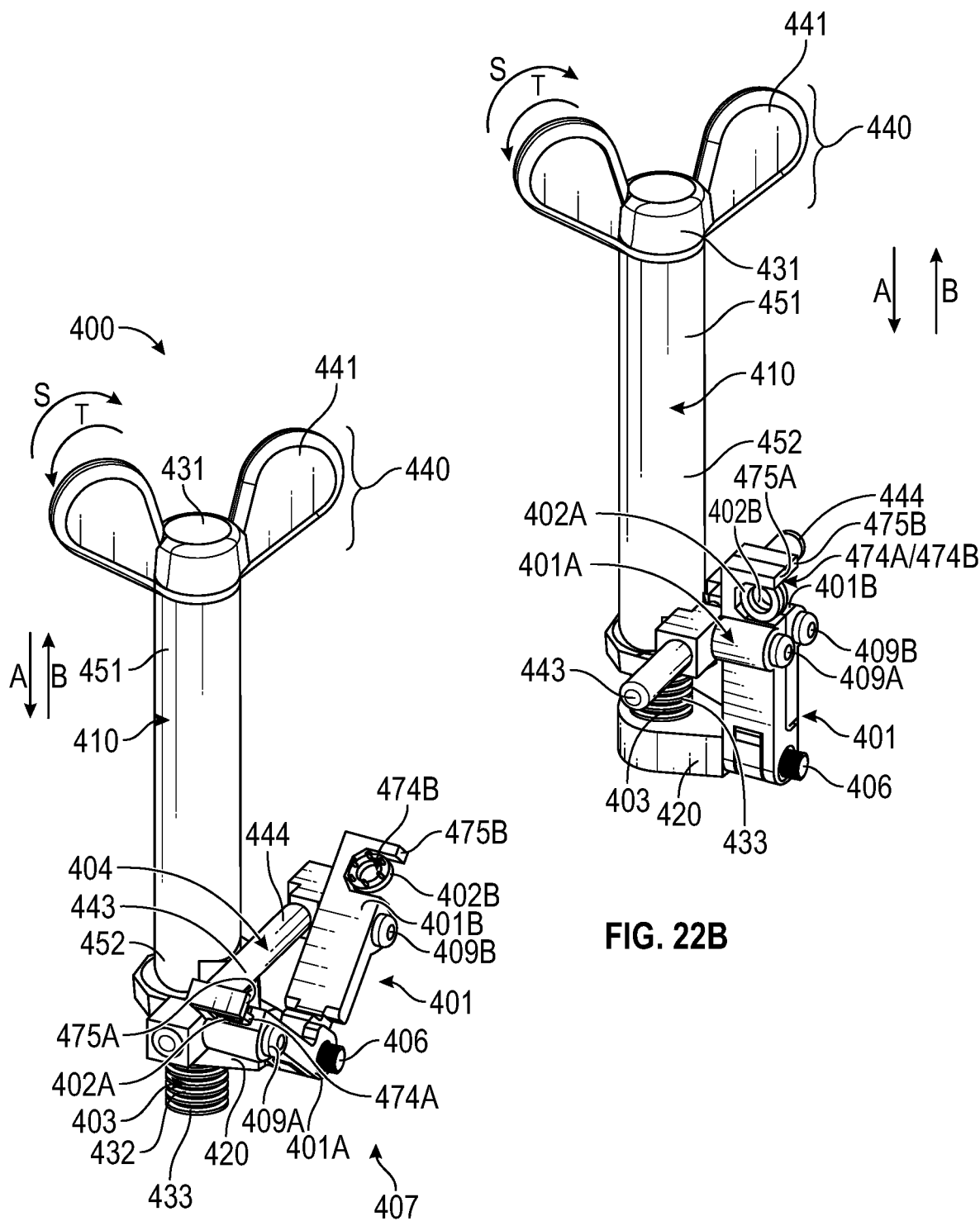
FIG. 22A is a perspective view of a fourth embodiment of a device for microvascular anastomosis related to FIG. 1 in an open configuration.
FIG. 22B is a perspective view of the device of FIG. 22A in a closed configuration.

Referring to FIGS. 22A and 22B, the rod 403 acts as a lead screw to actuate the lead nut 420 associated with the lower post 406 in the first axial direction A. In particular, the proximal portion 431 of the rod 403 includes a handle 441 that enables a point of manual or machine-driven rotation of the rod 403 about its axis of elongation. The proximal portion 451 of the elongated body 410 can sheathe the rod 403 as shown. As the rod 403 is rotated in a first rotational direction Q, the lead nut 420 associated with the first coupler arm 401A and second coupler arm 401B are forced downwards in the first axial direction A. The distal portion 452 of the elongated body 410 includes a support arm 404 fixed thereof and spanning across the elongated body 410. As shown, the support arm 404 is oriented perpendicular to a direction of elongation of the elongated body 410 and defines a first portion 443 and a second portion 444.

Figure 23:
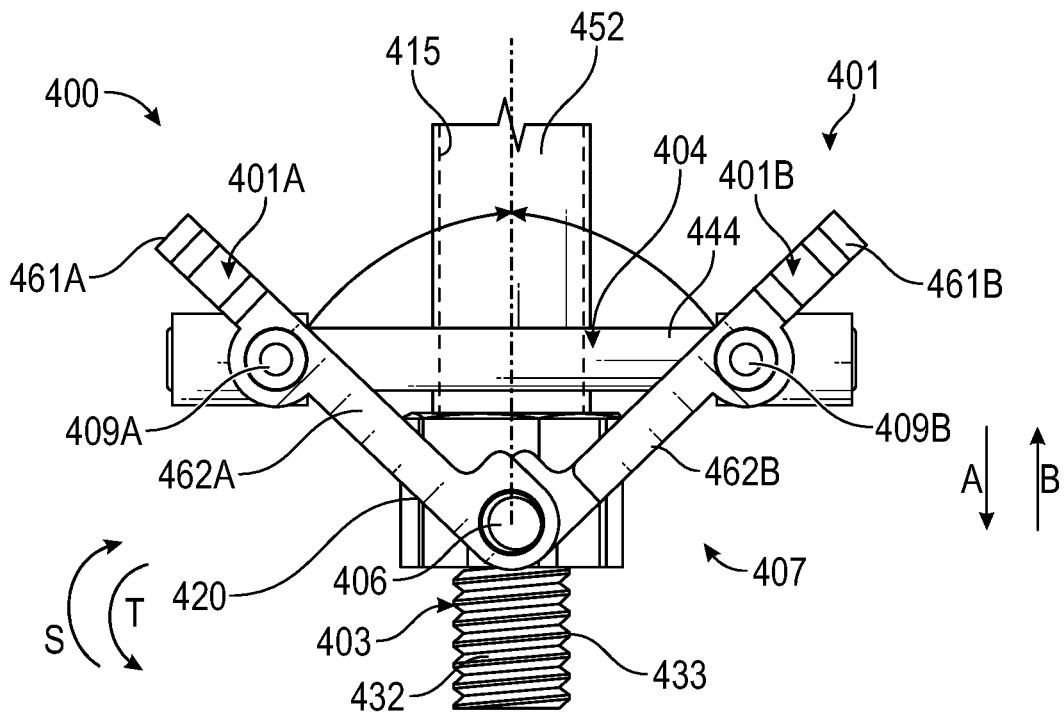
FIG. 23 is an enlarged front view of the device of FIG. 22A.
Figure 24:
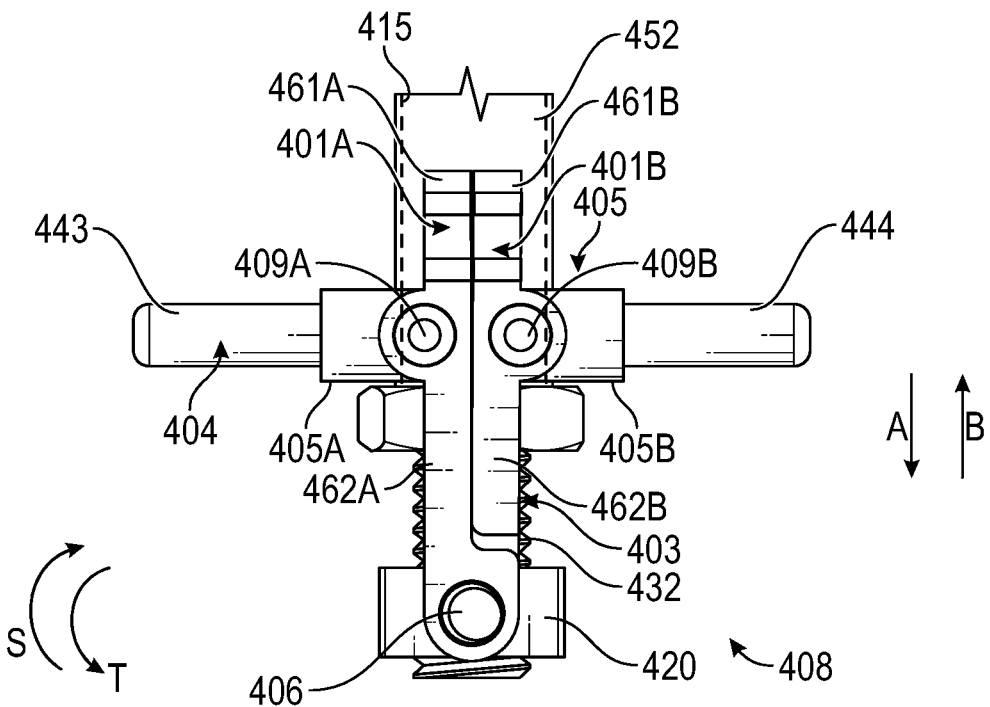
FIG. 24 is an enlarged front view of the device of FIG. 22A in a closed configuration.
Figure 25A:
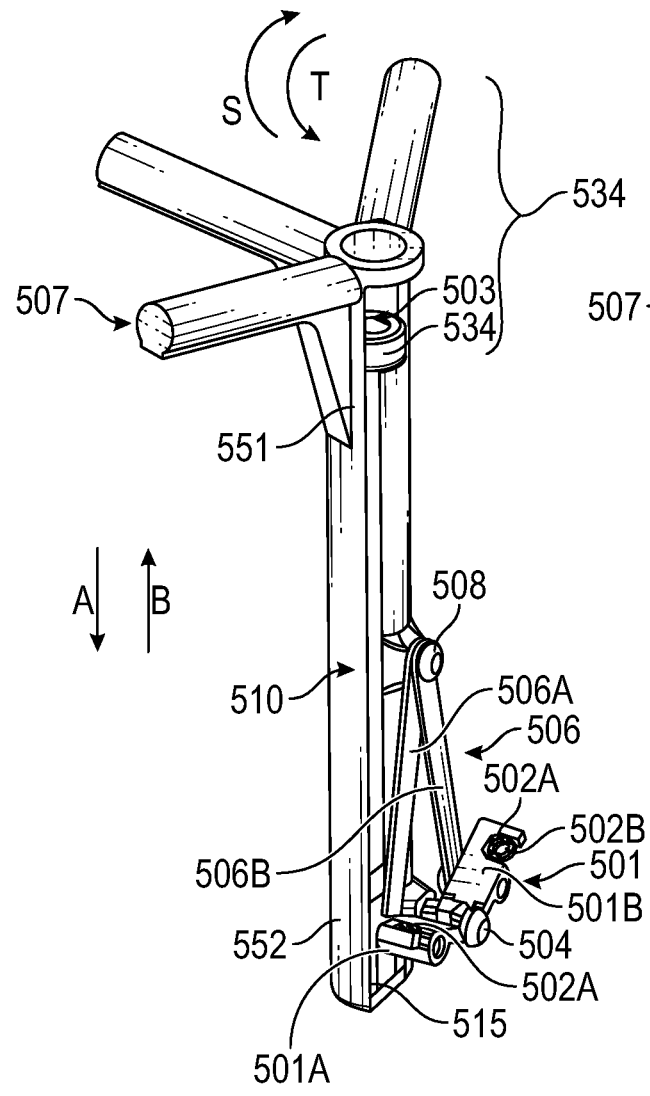
FIG. 25A is a perspective view of a fifth embodiment of a device for microvascular anastomosis related to FIG. 1 in an open configuration.
Figure 25B:
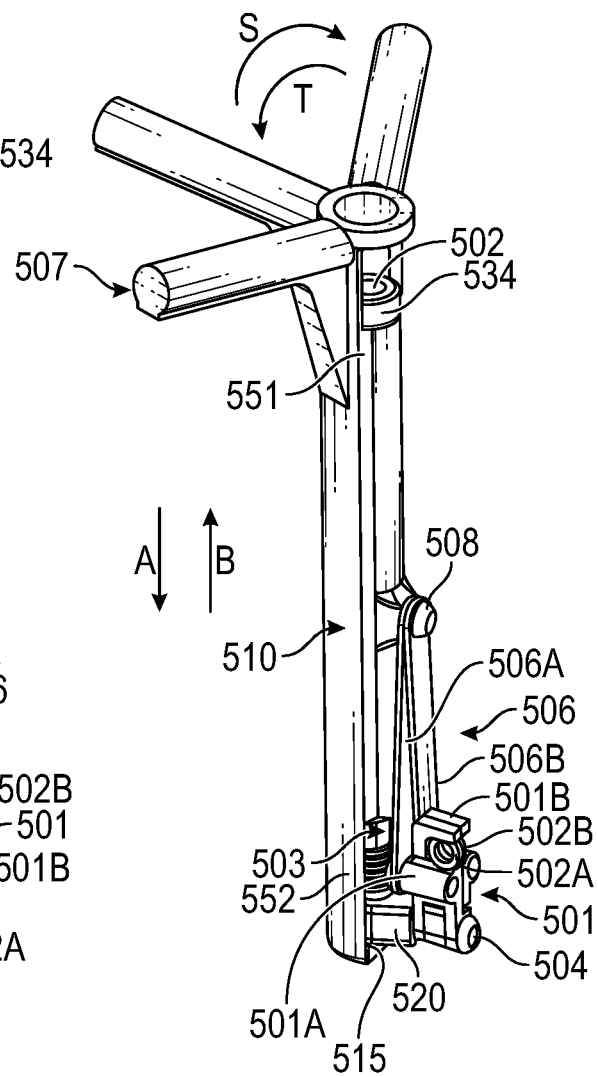
FIG. 25B is a perspective view of the device of FIG. 25A in a closed configuration.

Referring directly to FIGS. 23 and 24, the first coupler arm 401A and the second coupler arm 401B of a pair of coupler arms 401 are joined at the lead nut 420 by a lower post 406. In particular, the first coupler arm 401A and the second coupler arm 401B each include a free end 461A and 461B and a pivotable end 462A and 462B. The pivotable ends 462A and 462B of each coupler arm 401A and 401B are joined by and rotatable about the lower post 406. The coupler arms 401A and 401B are operable to assume an open configuration as shown specifically in FIG. 23, and a closed configuration as shown specifically in FIG. 24. The first coupler arm 401A includes a first intermediate post 409A in slidable association with the first portion 443 of the support arm 404. Similarly, the second coupler arm 401B includes a second intermediate post 409B in slidable association with the second portion 444 of the support arm 404. During actuation of the lead nut 420 in the first axial direction A, the lower post 406 is guided downward as the lead nut 420 is forced downward in the first axial direction A. This motion forces the pivotable ends 462A and 462B of each coupler arm 401A and 401B downward. As the pivotable ends 462A and 462B of each coupler arm 401A and 401B are connected by the lower post 406, the free ends 461A and 461B of each coupler arm 401A and 401B are drawn together into the closed configuration as the pivotable ends 462A and 462B are forced downward in the first axial direction A. This motion is guided by the support arm 404 which guides the first and second intermediate posts 409A and 409B associated with each coupler arm 401A and 401B together as shown between FIGS. 23 and 24. The first and second intermediate posts 409A and 409B are slidably mounted on the support arm 404. In the open configuration, the first and second intermediate posts 409A and 409B are in a lateral position on the support arm 404 as shown in FIG. 23. In the closed configuration, the first and second intermediate posts 409A and 409B are in a medial position on the support arm 404 as shown in FIG. 24. Each respective coupler arm 401A and 401B includes a receptacle 474A and 474B including an open portion 475A and 475B configured to receive a portion of a ring-and-pin coupler (not shown). Each respective portion of the ring-and-pin coupler can be removed from the respective coupler arm 401A and 401B through the open portion 475A and 475B of the coupler arm 401A and 401B.

FIGS. 25A-26B illustrate an embodiment of a coupler device, designated 500, including a first coupler arm 501A and a second coupler arm 501B in association with a rod 503. The first coupler arm 501A and the second coupler arm 501B are each configured to receive a respective portion 502A and 502B of a coupler ring 502. The rod 503 defines a proximal portion 531 and a distal portion 532 associated with the first and second coupler arms 501A and 501B by a lower post 504 that couples the first and second coupler arms 501A and 501B. The lower post 504 is fixed to a lead nut 520 that is configured for actuation in a first axial direction A by an actuator 540 in association with the proximal portion 531 of the rod 503. As shown, the actuator 540 can include a lead screw arrangement similar to that of the device 400. As the rod 503 is rotated and the lead nut 520 is consequently actuated in the first axial direction A, the first and second coupler arms 501A and 501B and the first and second portions 502A and 502B of the coupler ring 502 are drawn together. This arrangement enables the first and second coupler arms 501A and 501B to assume an open configuration or a closed configuration. The coupler device 500 further defines an elongated body 510 including a proximal portion 551, a distal portion 552, and a channel 515 defined axially through the elongated body 510 for receipt of the rod 503. The proximal portion 551 of the elongated body 510 is configured to house or otherwise provide support for the actuator 540 and the proximal portion 551 of the rod 503. In some embodiments, the elongated body 510 further includes one or more grip elements 507 in association with the actuator housing 541 that enables a practitioner to comfortably wield and stabilize the device 500 when coupling vessels together using the device 500.

As shown, the rod 503 can act as a lead screw to actuate the lower post 504 in the first axial direction A by rotation of the rod 503 about its direction of elongation in a first rotational direction S. The lower post 504 is coupled directly to the lead nut 520, which is in turn engaged with a threaded external surface 533 of the rod 503. In particular, the proximal portion 531 of the rod 503 includes an engagement point 534 that enables a point of manual or machine-driven rotation of the rod 503 about its axis of elongation. As the rod 503 is rotated in the first rotational direction S acting as a lead screw, the lead nut 520 associated with the first coupler arm 501A and second coupler arm 501B is forced downwards in the first axial direction A based on the direction of the threading along the threaded external surface 533.

Figure 26A:
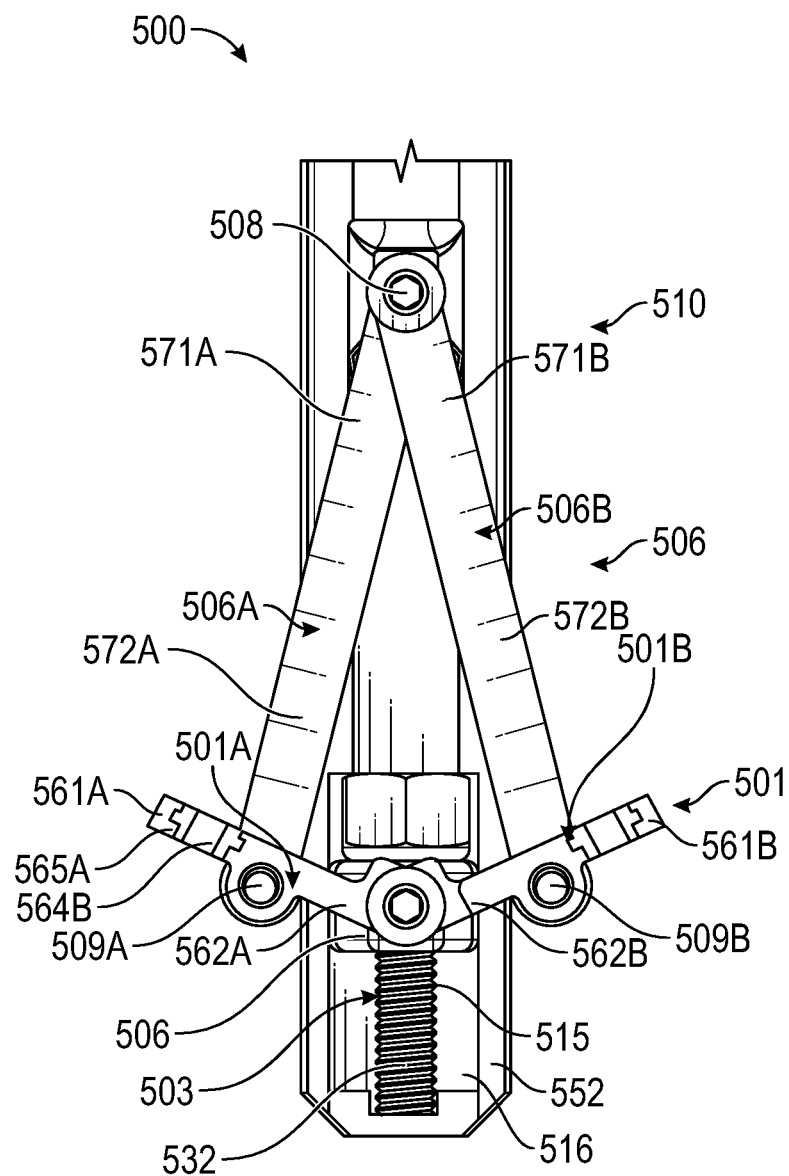
FIG. 26A is an enlarged front view of the device of FIG. 25A in an open configuration.
Figure 26B:
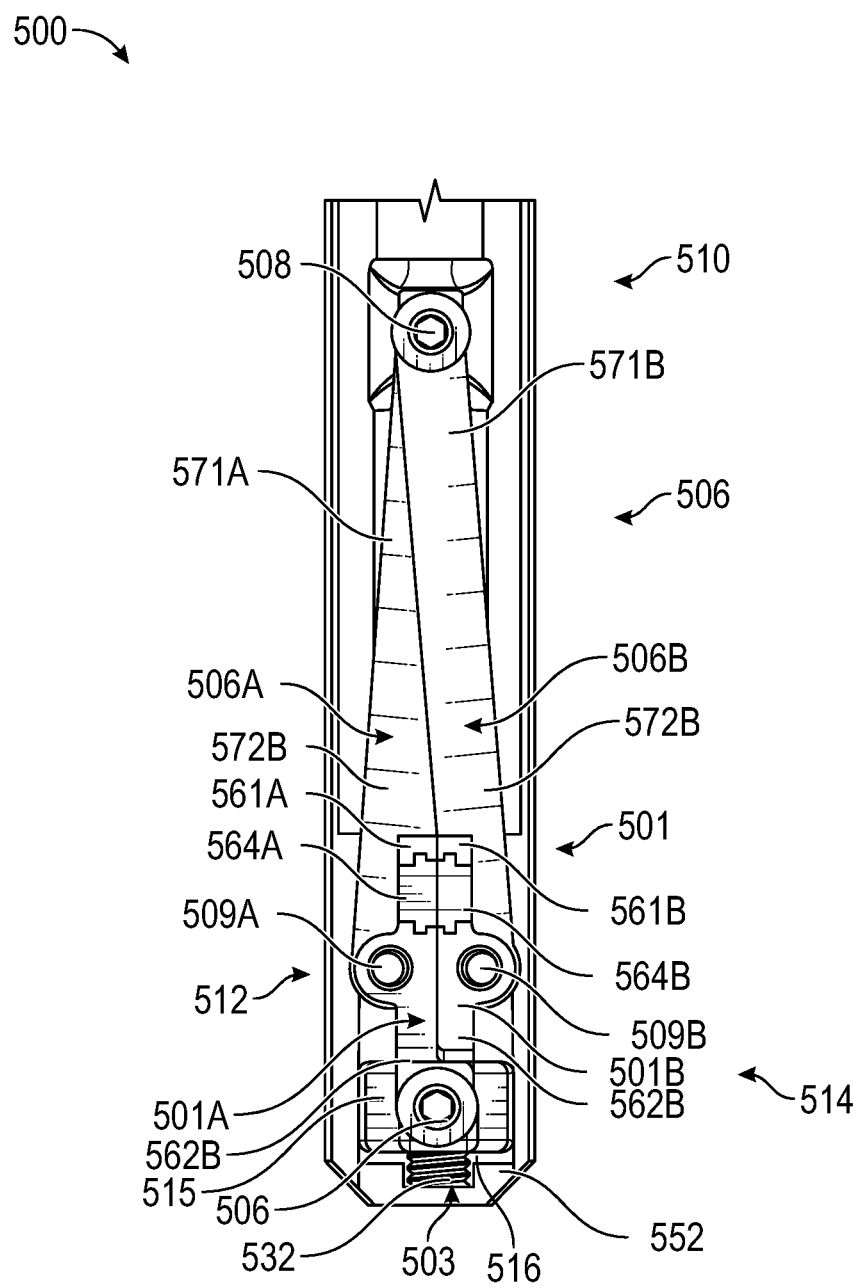
FIG. 26B is an enlarged front view of the device of FIG. 25A in a closed configuration.

Referring directly to FIGS. 26A and 26B, the first coupler arm 501A and the second coupler arm 501B of the pair of coupler arms 501 are joined at the distal portion 532 of the rod 503 by a lower post 504 coupled directly to the lead nut 520. In particular, the first coupler arm 501A and the second coupler arm 501B each define a free end 561A and 561B and a pivotable end 562A and 562B. The pivotable ends 562A and 562B of each coupler arm 501A and 501B are joined by and rotatable about the lower post 504. The coupler arms 501A and 501B are operable to assume an open configuration as shown specifically in FIG. 26A, and a closed configuration as shown specifically in FIG. 26B. The first coupler arm 501A includes a first intermediate post 509A in association with a distal portion 572A of a first support arm 506A of a pair of support arms 506. Similarly, the second coupler arm 501B includes a second intermediate post 509B in association with a distal portion 572B of a second support arm 506B of the pair of support arms 506. The first and second support arms 506A and 506B each include a proximal portion 571A and 571B that are pivotably coupled to the elongated body by an upper post 508, as shown. The elongated body 510 defines a lower portion 516 of the channel 515. During actuation of the lead nut 520 in the first axial direction A by the rod 502, the lower post 504 is guided downward through the lower portion 516 of the channel 515 as the lead nut 520 is forced downward in the first axial direction A. This motion forces the pivotable ends 562A and 562B of each coupler arm 506A and 506B downward. As the pivotable ends 562A and 562B of each coupler arm 506A and 506B are connected by the lower post 504, the free ends 561A and 561B of each coupler arm 506A and 506B are drawn together into the closed configuration as the pivotable ends 562A and 562B are forced downward in the first axial direction A. This motion is guided by the first and second support arms 506A and 506B which guide the first and second intermediate posts 509A and 509B associated with each coupler arm 506A and 506B together as shown between FIGS. 26A and 26B.

Each respective coupler arm 506A and 506B includes a receptacle 564A and 564B defining an open portion 565A and 565B configured to receive a portion 502A or 502B of a ring-and-pin coupler 502. Each respective portion 502A or 502B of the ring-and-pin coupler 502 can be removed from the respective coupler arm 506A and 506B through the open portion 565A and 565B of the coupler arm 506A and 506B.

To close the coupler arms 501, the rod 503 is rotated in a first rotational direction S and the associated lead nut 520 is then driven in the first axial direction A along with the lower post 504. During actuation of the lead nut 520 in the first axial direction A by the rod 503, the lower post 504 is guided downward through the lower portion 516 of the channel 515 as the lead nut 520 is forced downward in the first axial direction A. This motion forces each coupler arm 506A and 506B together in the closed configuration. Similarly, to open the coupler arms 501, the rod 503 is rotated in a second rotational direction T and the associated lead nut 520 is driven in the second axial direction B along with the lower post 504. During actuation of the lead nut 520 in the second axial direction B by the rod 503, the lower post 504 is guided upward through the lower portion 516 of the channel 515 as the lead nut 520 is forced upward in the first axial direction A. This motion forces each coupler arm 506A and 506B apart in the open configuration.

FIGS. 27A-29 illustrate an embodiment of a coupler device, designated 600, having a first coupler arm 601A and a second coupler arm 601B in association with a rod 603. The first coupler arm 601A and the second coupler arm 601B are each configured to receive a respective portion 602A and 602B of a coupler ring 602. The rod 603 defines a proximal portion 631 and a distal portion 632 associated with the first and second coupler arms 601A and 601B. The rod 603 is operable for actuation in a first axial direction A by an actuator 640 in association with the proximal portion 631 of the rod 603. As the rod 603 is actuated in the first axial direction A, the first and second coupler arms 601A and 601B and consequently the first and second portions 602A and 602B of the coupler ring 602 are drawn together. This arrangement enables the first and second coupler arms 601A and 601B to assume an open configuration or a closed configuration. The coupler device 600 further defines an elongated body 610 including a proximal portion 651, a distal portion 652, and a channel 615 defined axially through the elongated body 610 for receipt of the rod 603. The proximal portion 651 of the elongated body 610 is configured to house or otherwise provide support for the actuator 640 and the proximal portion 631 of the rod 603. The actuator 640 of the coupler device 600 of FIGS. 27A-29 includes a tensioned arrangement to actuate the rod 603 in the first axial direction A.

In some embodiments, the actuator 640 includes a tensioning element 609 and an associated catch release 617 that enable closure of the first and second coupler arms 601A and 601B through release of the tensioning element 609 forcing the rod 603 downward in a first axial direction A. In particular, the tensioning element 609 is fixed to the proximal portion 631 of the rod 603 and the catch release 617 is fixed to the proximal portion 651 of the elongated body 610. The catch release 617 maintains the tensioning element 609 in a tensioned configuration with the rod 603 raised and the first and second coupler arms 601A and 601B in the open configuration. When the catch release 617 releases the tensioning element 609, the rod 603 is consequently actuated in the first axial direction A. In some embodiments, the elongated body 610 further includes a grip element 607 in association with the actuator housing 641 that enables a practitioner to wield and stabilize the device 600 when coupling vessels together using the device 600.

Figures 27A, 27B:
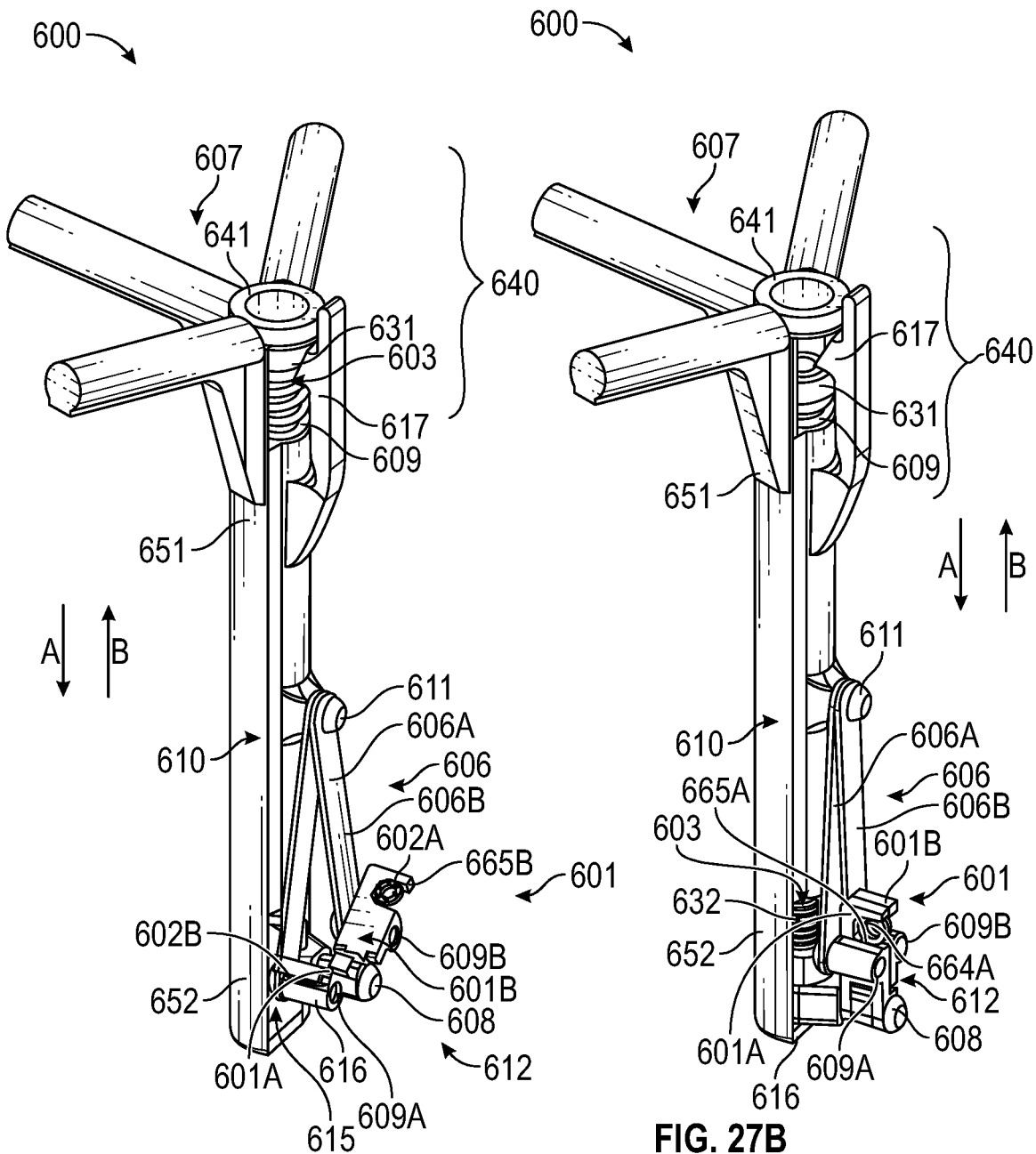
FIG. 27A is a perspective view of a sixth embodiment of a device for a microvascular anastomosis related to FIG. 1 in an open configuration.
FIG. 27B is a perspective view of the device of FIG. 27A in a closed configuration.
Figure 28A:
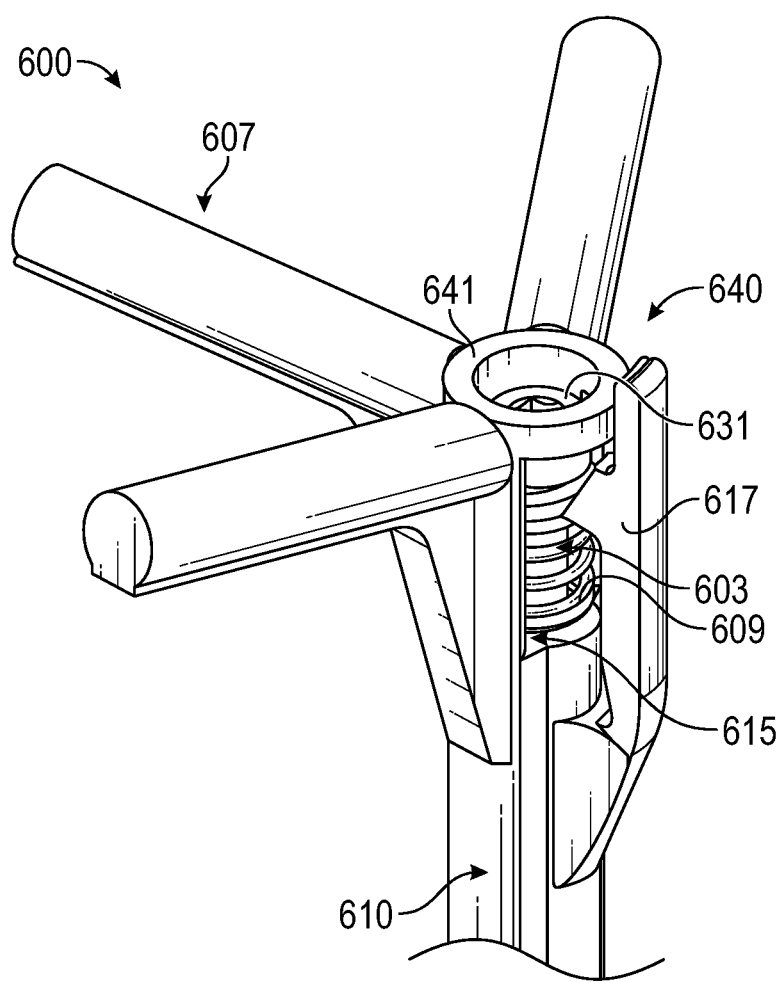
FIG. 28A is an enlarged perspective view of an actuator of the device of FIG. 27A in an open configuration.
Figure 28B:
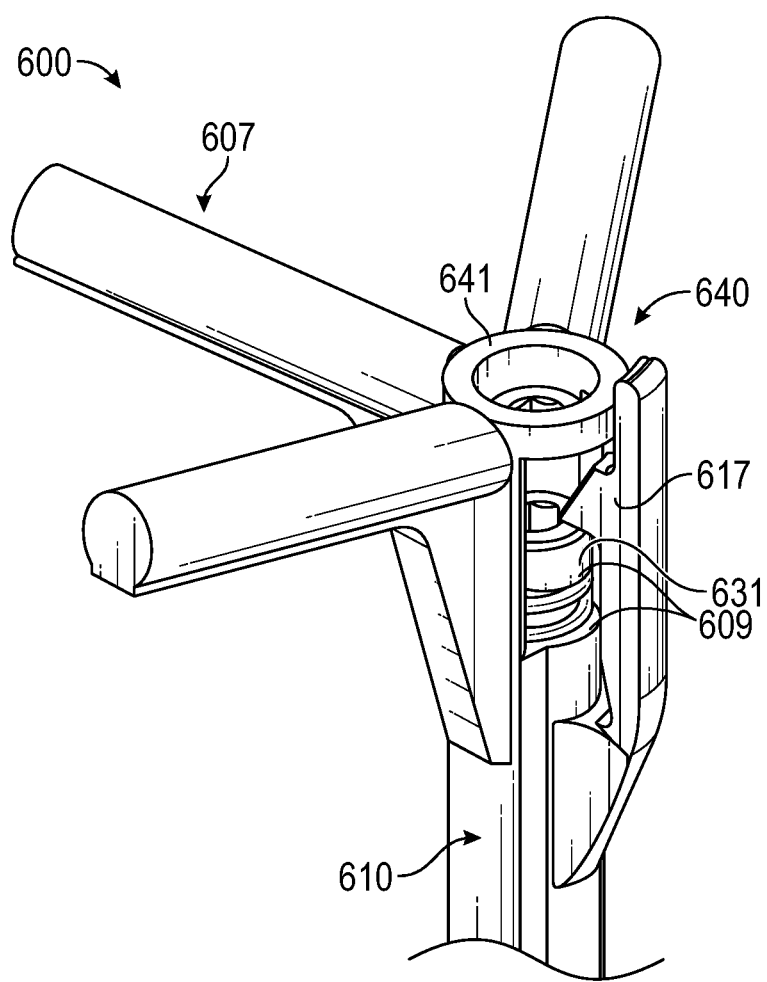
FIG. 28B is an enlarged perspective view of an actuator of the device of FIG. 27A in a closed configuration.
Figure 29:
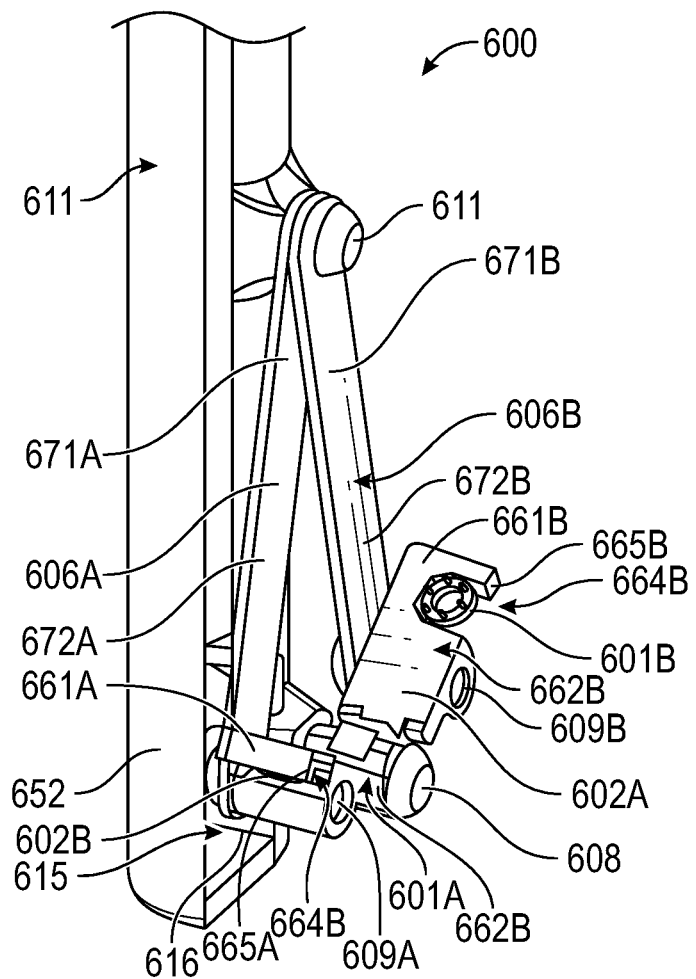
FIG. 29 is an enlarged perspective view of a pair of coupler arms of the device of FIG. 27A in the open configuration.

Referring directly to FIGS. 27A, 27B and 29, the first coupler arm 601A and the second coupler arm 601B of the pair of coupler arms 601 are joined at the distal portion 632 of the rod 603 by a lower post 608. In particular, the first coupler arm 601A and the second coupler arm 601B each include a free end 661A and 661B and a pivotable end 662A and 662B. The pivotable ends 662A and 662B of each coupler arm 601A and 601B are joined by and rotatable about the lower post 608. The coupler arms 601A and 601B are operable to assume an open configuration as shown specifically in FIG. 27A, and a closed configuration as shown specifically in FIG. 27B. The first coupler arm 601A includes a first intermediate post 609A in association with a distal portion 672A of a first support arm 606A of a pair of support arms 606. Similarly, the second coupler arm 601B includes a second intermediate post 609B in association with a distal portion 672B of a second support arm 606B of a pair of support arms 606. The first and second support arms 606A and 606B each include a proximal portion 671A and 671B that are pivotably coupled to the elongated body by an upper post 611, as shown. The elongated body 610 defines a lower portion 616 of the channel 615. During actuation of the rod 603 in the first axial direction A, the lower post 608 is guided downward through the lower portion 616 of the channel 615 as the rod 603 is forced downward in the first axial direction A. This motion forces the pivotable ends 662A and 662B of each coupler arm 606A and 606B downward. As the pivotable ends 662A and 662B of each coupler arm 606A and 606B are connected by the lower post 608, the free ends 661A and 661B of each coupler arm 606A and 606B are drawn together into the closed configuration as the pivotable ends 662A and 662B are forced downward in the first axial direction A. This motion is guided by the first and second support arms 606A and 606B which guide the first and second intermediate posts 609A and 609B associated with each coupler arm 606A and 606B together as shown between FIGS. 27A and 27B.

Each respective coupler arm 606A and 606B includes a receptacle 664A and 664B including an open portion 665A and 665B configured to receive a portion 602A or 602B of a ring-and-pin coupler 602. Each respective portion 602A or 602B of the ring-and-pin coupler 602 can be removed from the respective coupler arm 606A and 606B through the open portion 665A and 665B of the coupler arm 606A and 606B.

To close the coupler arms 606, the catch release 617 releases the tensioning element 609 to drive the associated rod 603 in the first axial direction A. During actuation of the rod 603 in the first axial direction A by the tensioning element 609, the lower post 608 is guided downward through the lower portion 616 of the channel 615 as the rod 603 is forced downward in the first axial direction A. This motion forces each coupler arm 606A and 606B together in the closed configuration. Similarly, to open the coupler arms 606 following operation, the tensioning element 609 is re-tensioned to drive the rod 603 in a second axial direction B. The catch release 617 can then be re-set to hold the tensioning element 609 in a tensioned state. During actuation of the rod 603 in the second axial direction B, the lower post 608 is guided upward through the lower portion 616 of the channel 615 as the rod 603 is forced upward in the second axial direction B. This motion forces each coupler arm 606A and 606B apart to the open configuration.

Figure 30:
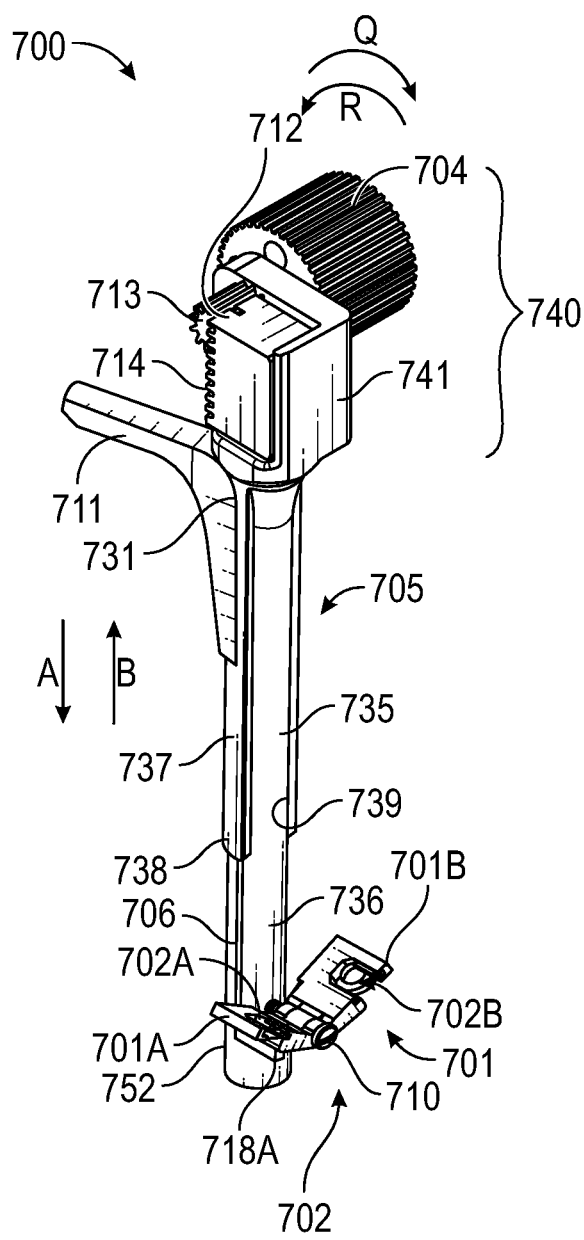
FIG. 30 is a perspective view of a seventh embodiment of a device for a microvascular anastomosis related to FIG. 1 in an open configuration.
Figure 31:
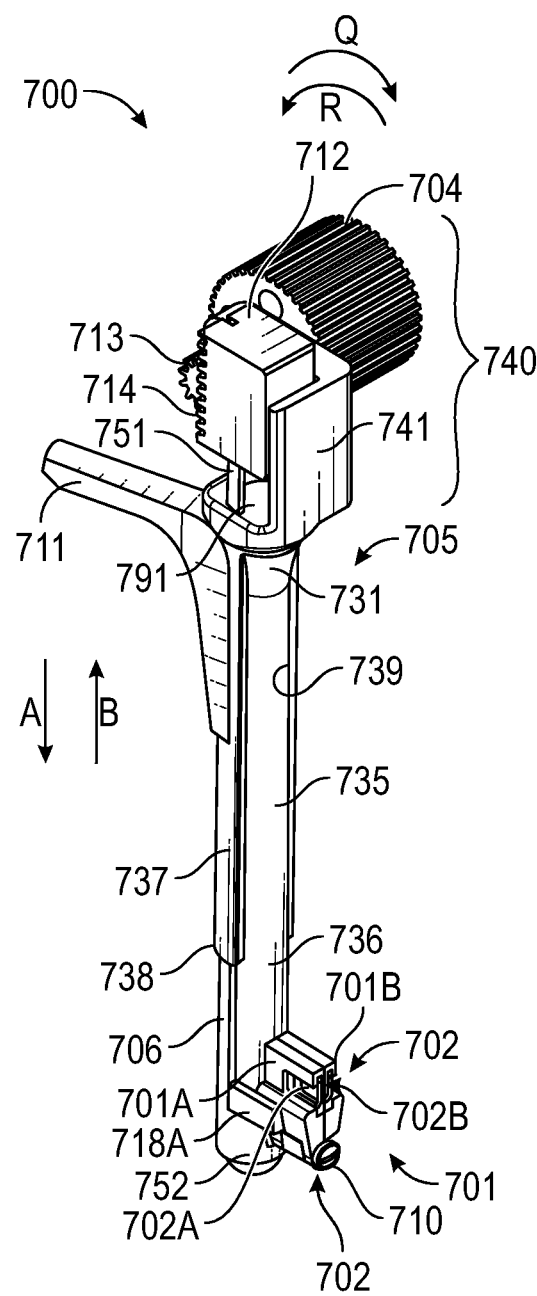
FIG. 31 is a perspective view of the device of FIG. 30 in a closed configuration.
Figure 32:
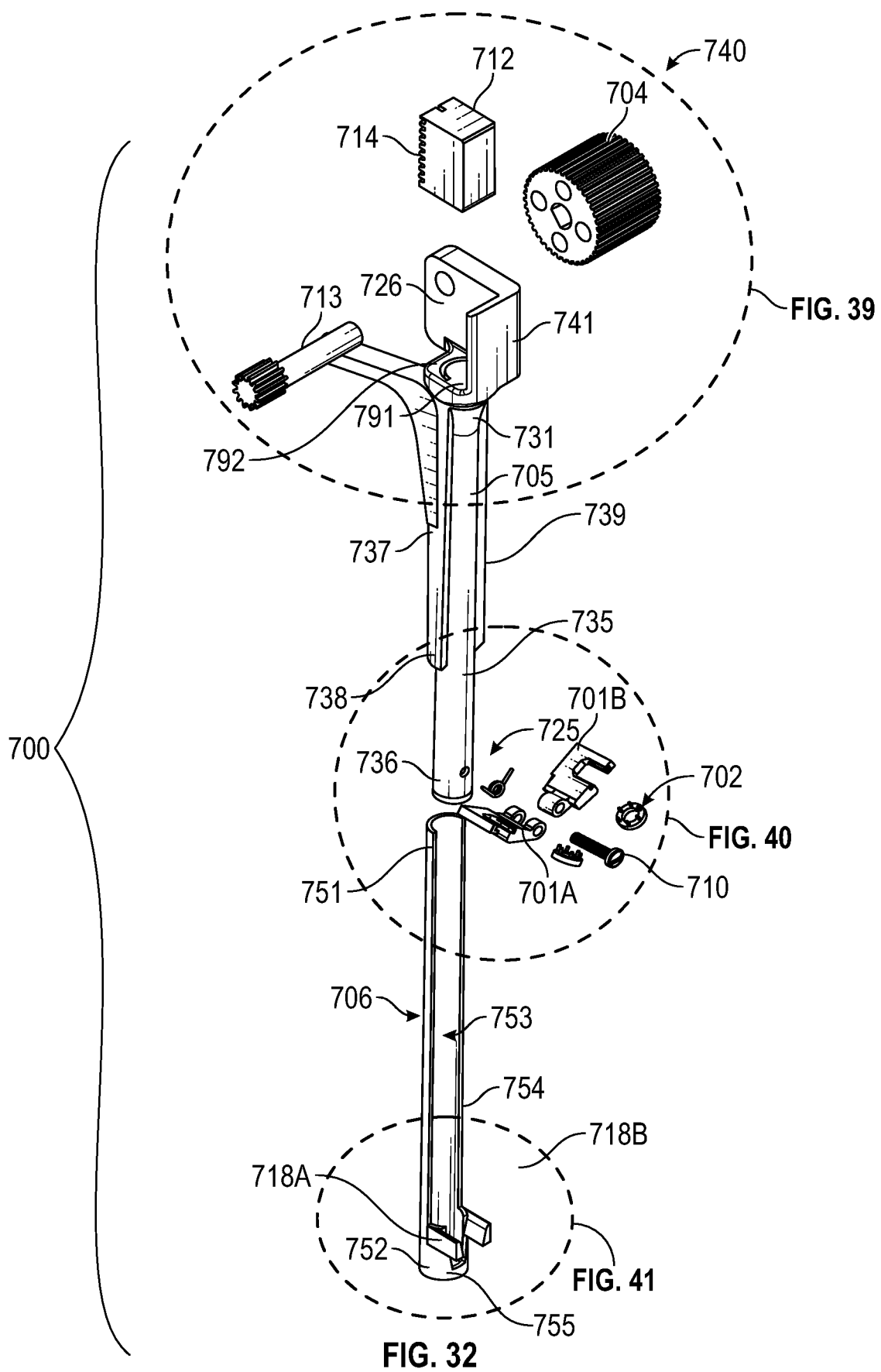
FIG. 32 is an exploded perspective view of the device of FIG. 30.
Figure 33:
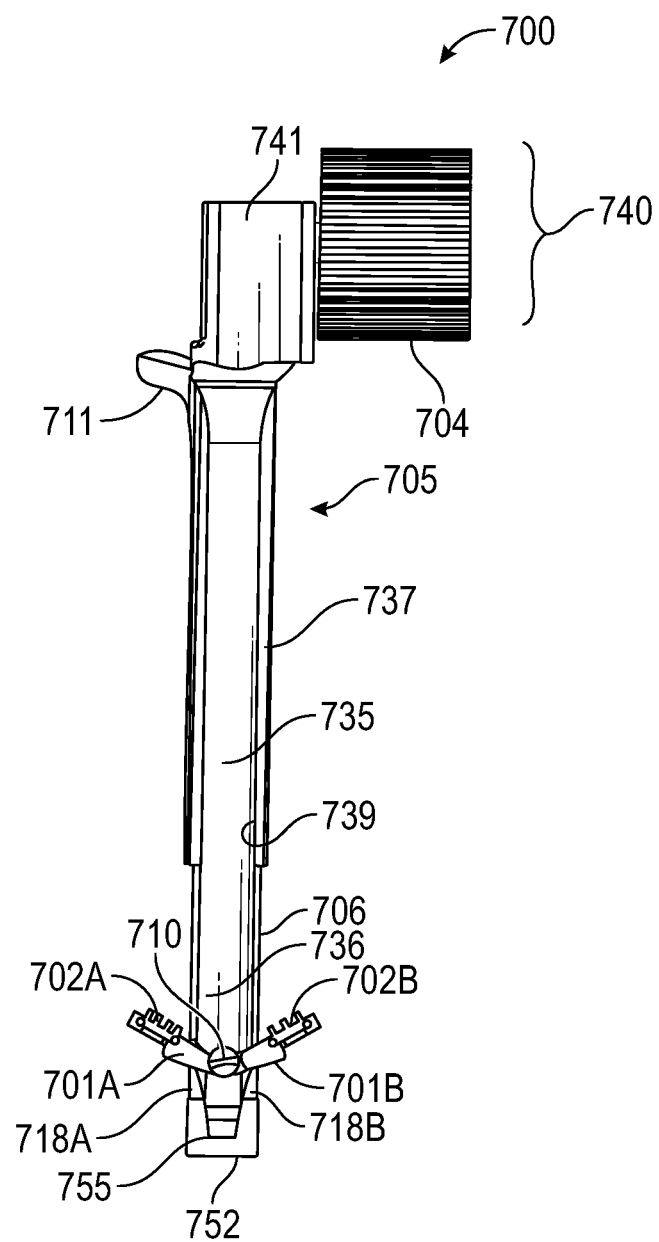
FIG. 33 is a front view of the device of FIG. 30 in the open configuration.
Figure 34:
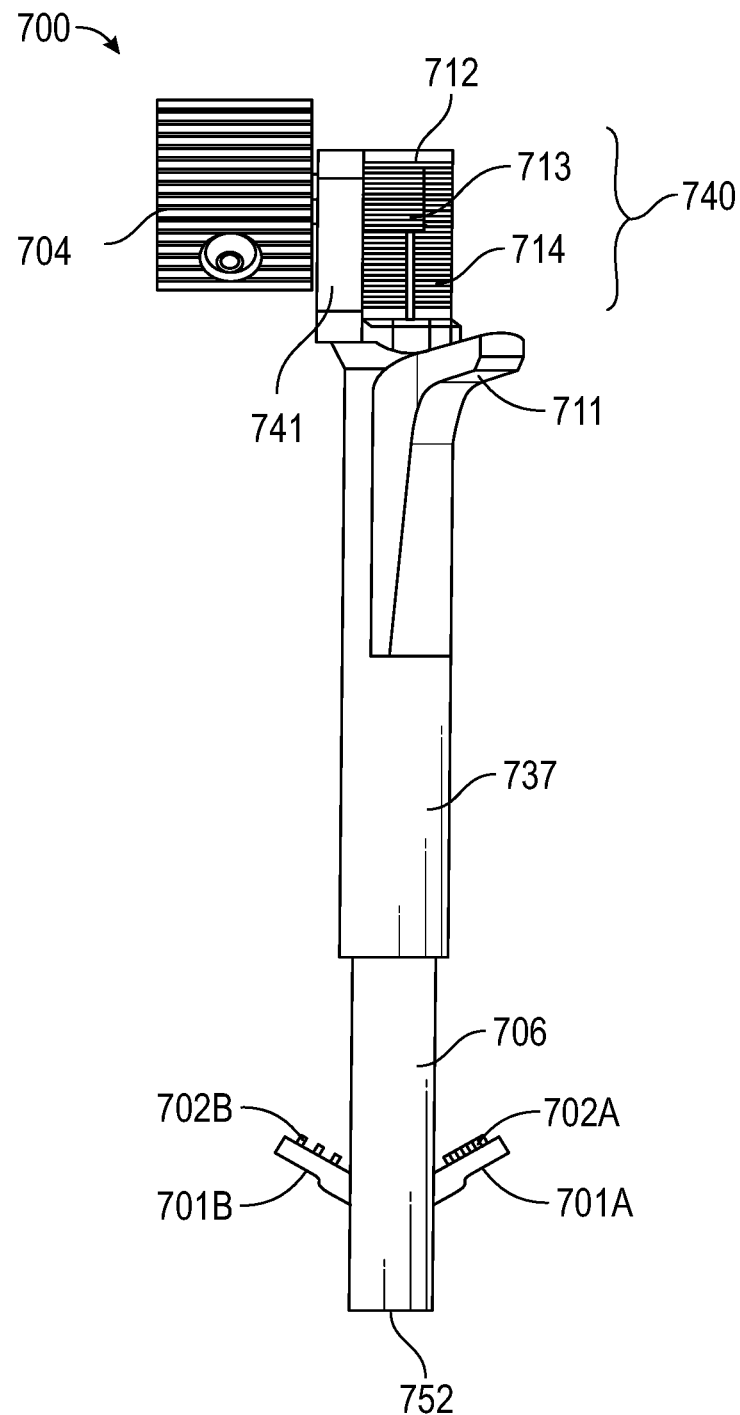
FIG. 34 is a rear view of the device of FIG. 30.
Figure 35:
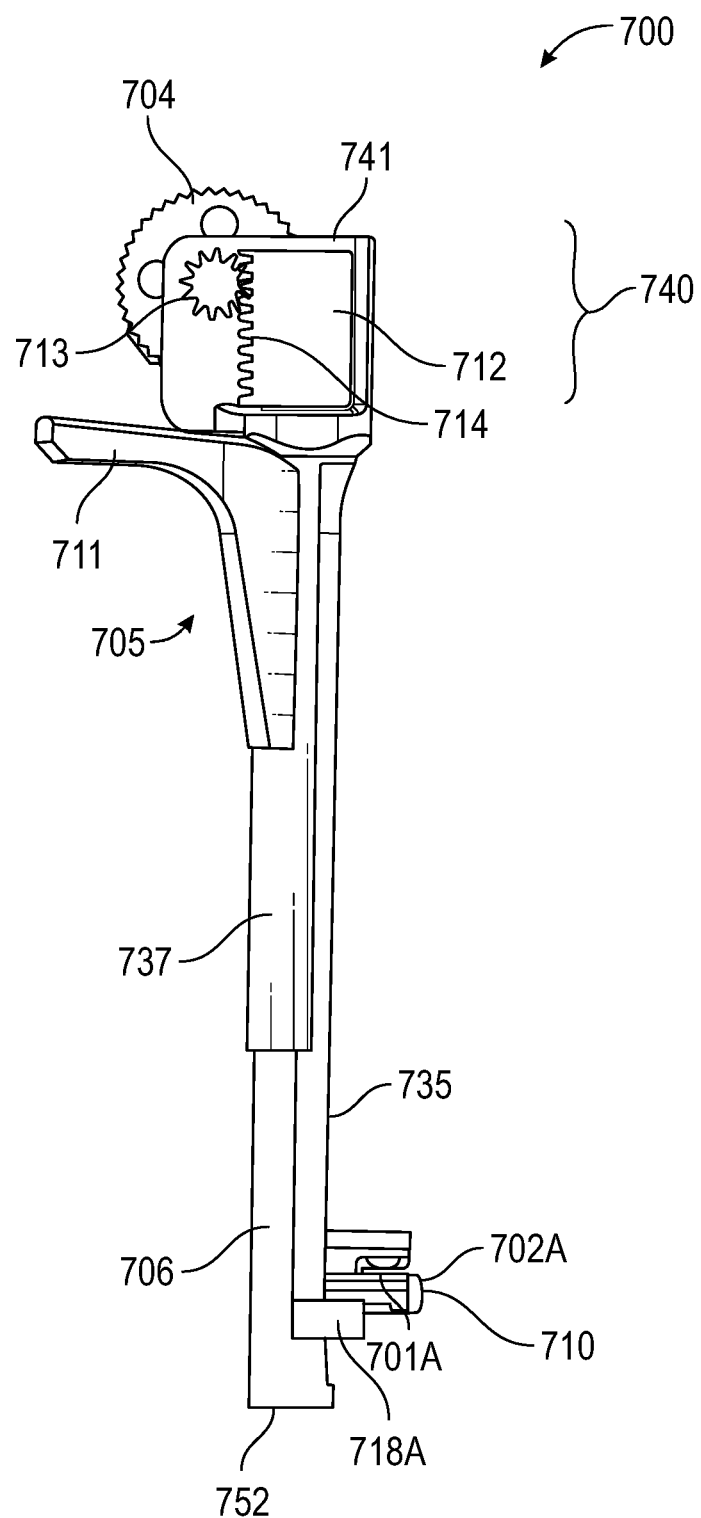
FIG. 35 is a left side view of the device of FIG. 30.
Figure 36:
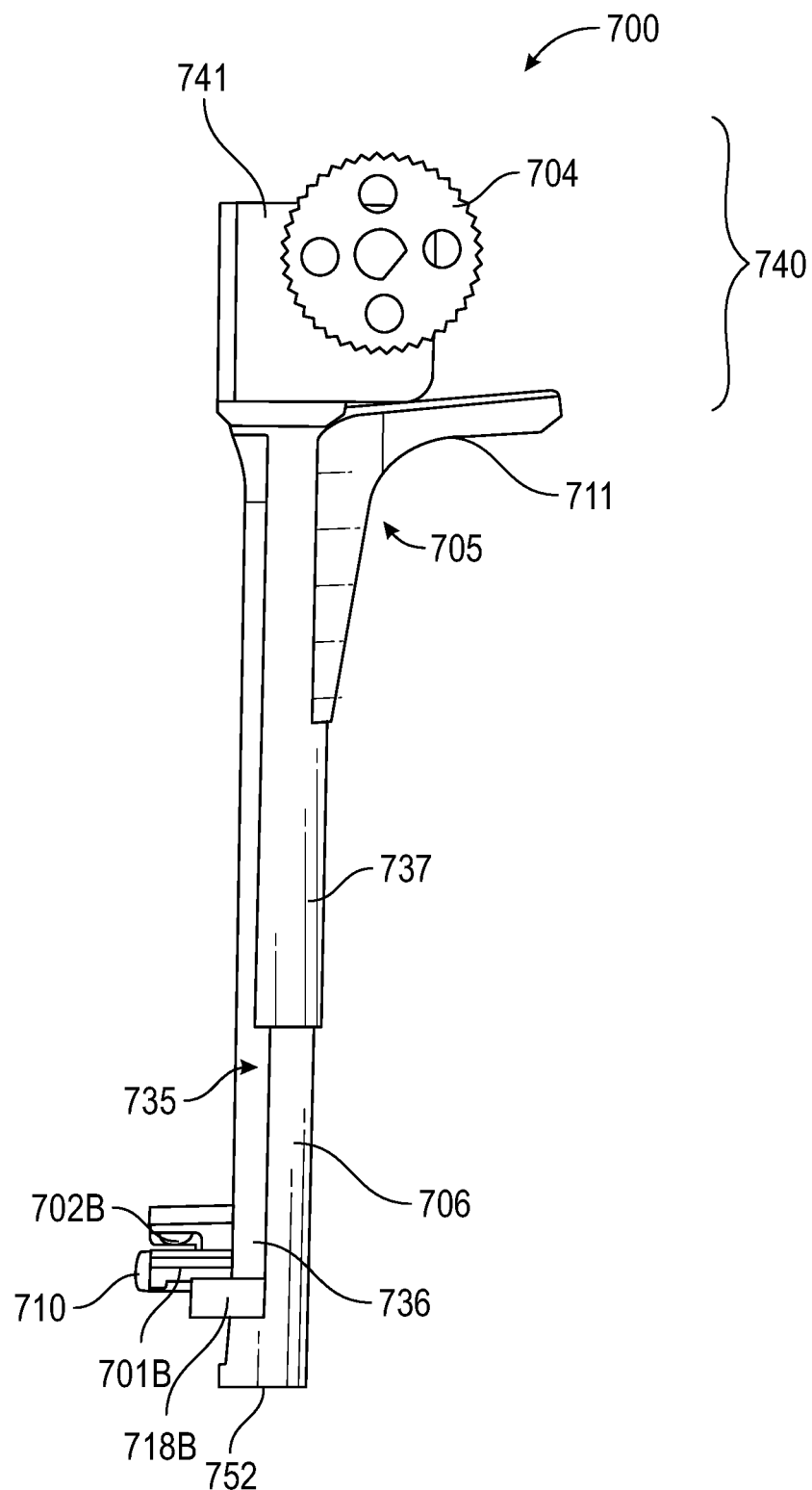
FIG. 36 is a right side view of the device of FIG. 30.
Figure 37:
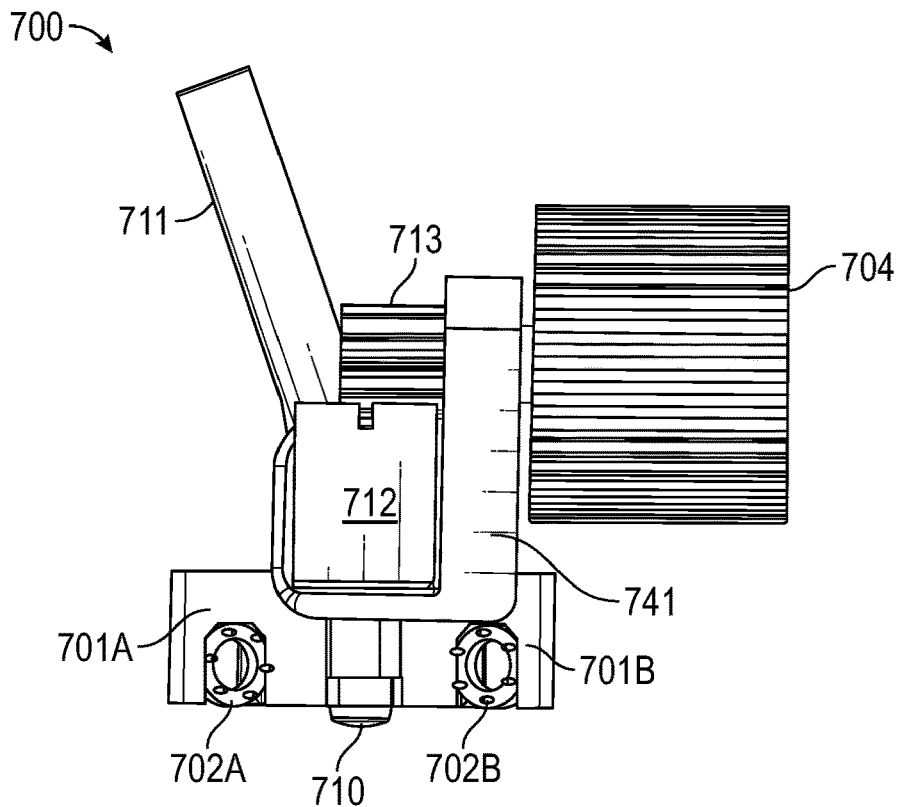
FIG. 37 is a top view of the device of FIG. 30.
Figure 38:
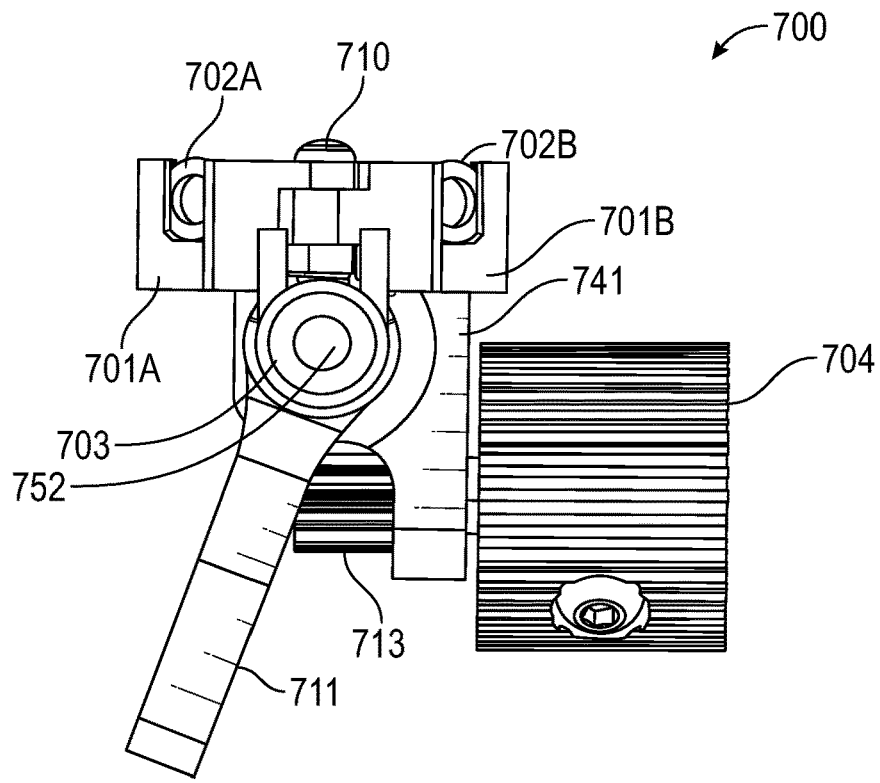
Figure 39:
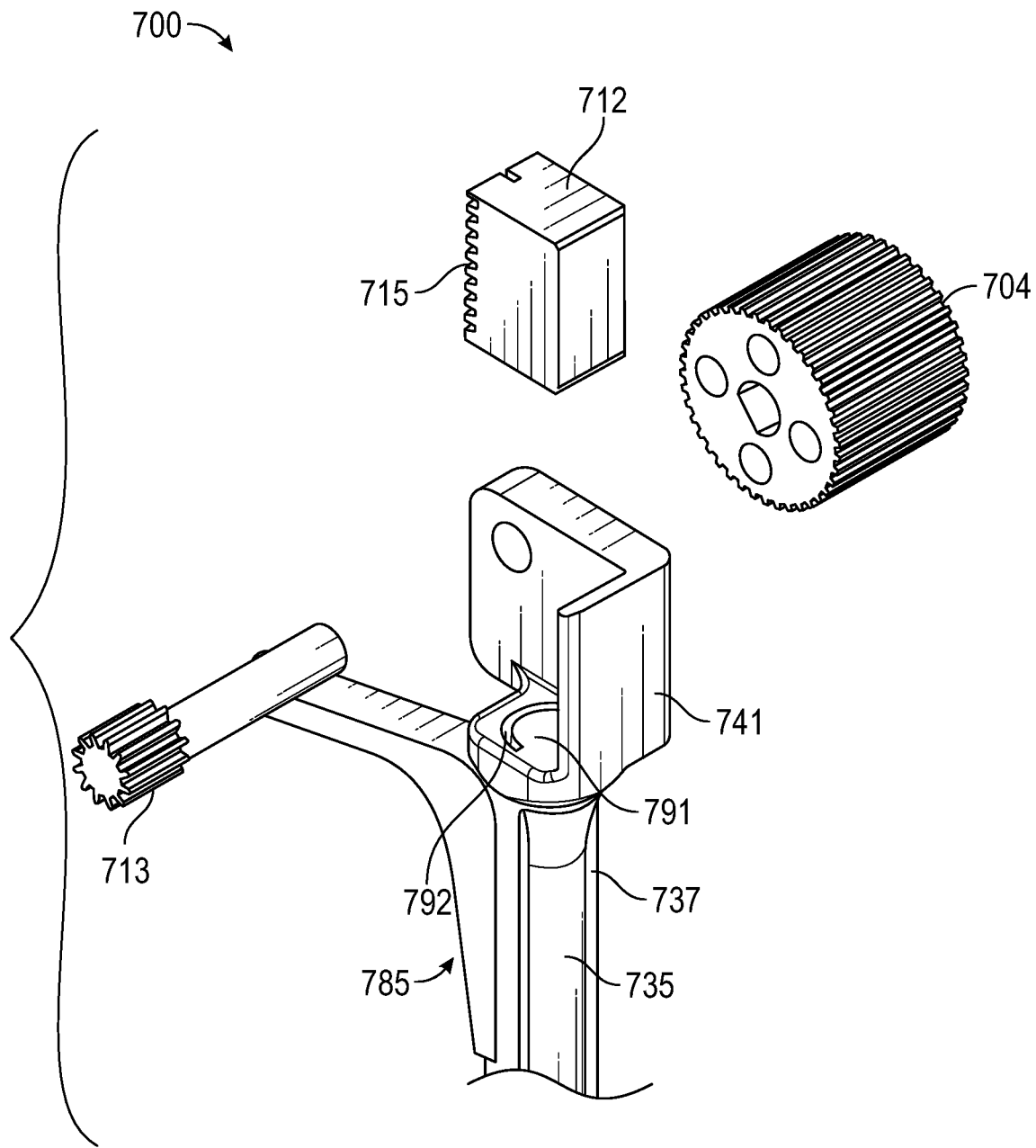
FIG. 39 is an enlarged exploded view of the device of FIG. 30 taken along circle 39 of FIG. 32.

FIGS. 30-41 illustrate an embodiment of a coupler device, designated 700, having a first coupler arm 701A and a second coupler arm 701B in association with an elongated body 705. The first coupler arm 701A and the second coupler arm 701B are each configured to receive a respective portion 702A and 702B of a coupler ring 702. The elongated body 705 defines a proximal portion 731, and further defines an inner rod portion 735 in coaxial alignment with an outer sheath portion 737 collectively defining a carriage slot 739 therebetween. The inner rod portion 735 and outer sheath portion 737 each include a respective free end 736 and 738, as specifically shown in FIG. 32. The free end 736 of the inner rod portion 735 is coupled with the first and second coupler arms 701A and 701B by a lower post 710. The carriage slot 739 of the elongated body 705 receives a carriage 706 defining a distal portion 752, a proximal portion 751, and a central channel 753 defining a frontal opening 754. In some embodiments, the frontal opening 754 of the carriage 706 defines a lower notch 755 for receipt of the lower post 710 when in the closed configuration. The proximal portion 751 of the carriage 706 is coupled directly to the actuator 740 through an actuator slot 792 defined at the proximal portion 731 of the elongated body 705. The carriage 706 is operable for actuation in an upward second axial direction B by an actuator 740 in association with the proximal portion 751 of the carriage 706, and at least partially encapsulates the inner rod 735 of the elongated body 705. The distal portion 752 of the carriage 706 includes a first wedge 718A and an opposite second wedge 718B defined on opposing sides of the frontal opening 754 and configured to guide the first and second coupler arms 701A and 701B together as the carriage 706 is actuated in the second axial direction B, as shown in FIGS. 30 and 31. The first and second coupler arms 701A and 701B and consequently the first and second portions 702A and 702B of the coupler ring 702 are drawn together by the first and second wedges 718A and 718B as a result of this motion. This arrangement enables the first and second coupler arms 701A and 701B to assume an open configuration or a closed configuration. The actuator housing 740 is located at the proximal portion 731 of the elongated body 705 and provides support for the actuator 740 and the proximal portion 751 of the carriage 706.

Figure 40:
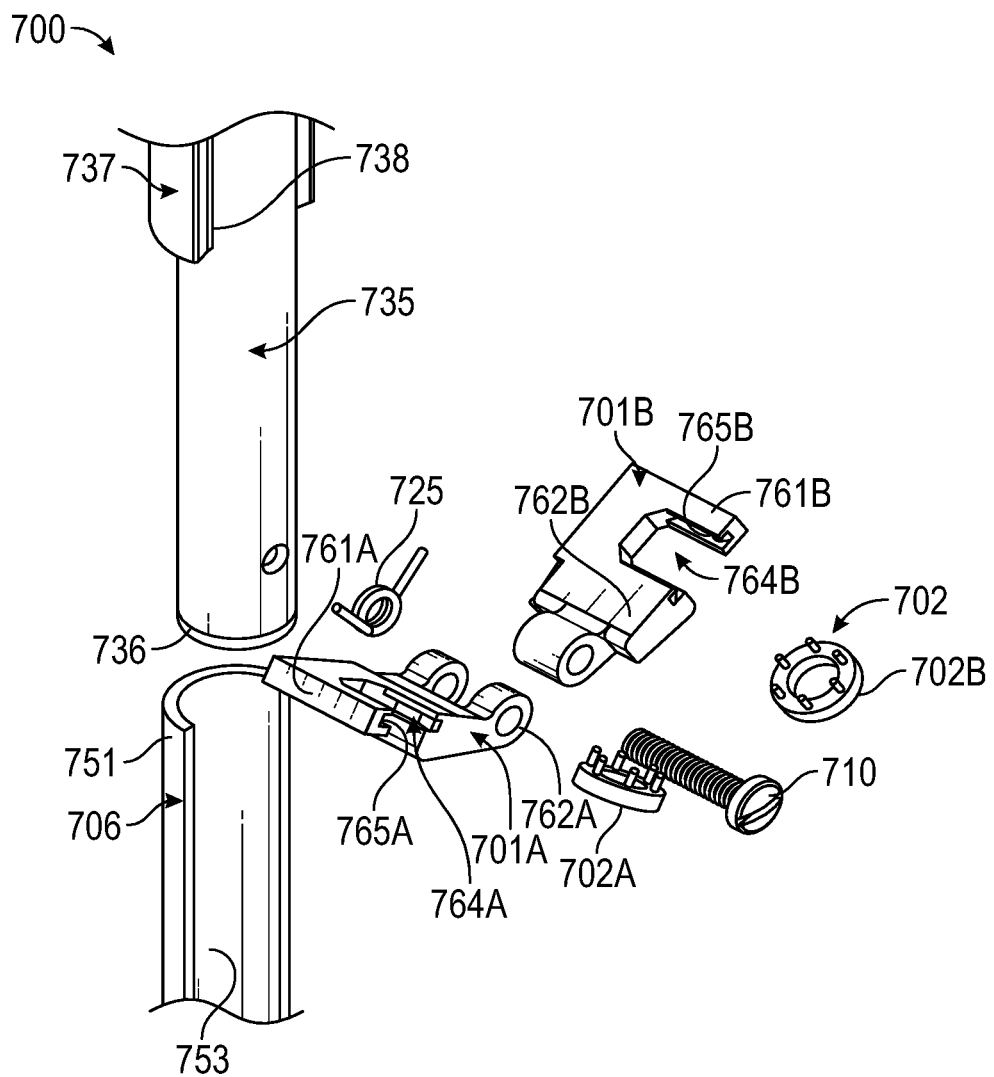
FIG. 40 is an enlarged exploded view of the device of FIG. 30 taken along circle 40 of FIG. 32.
Figure 41:
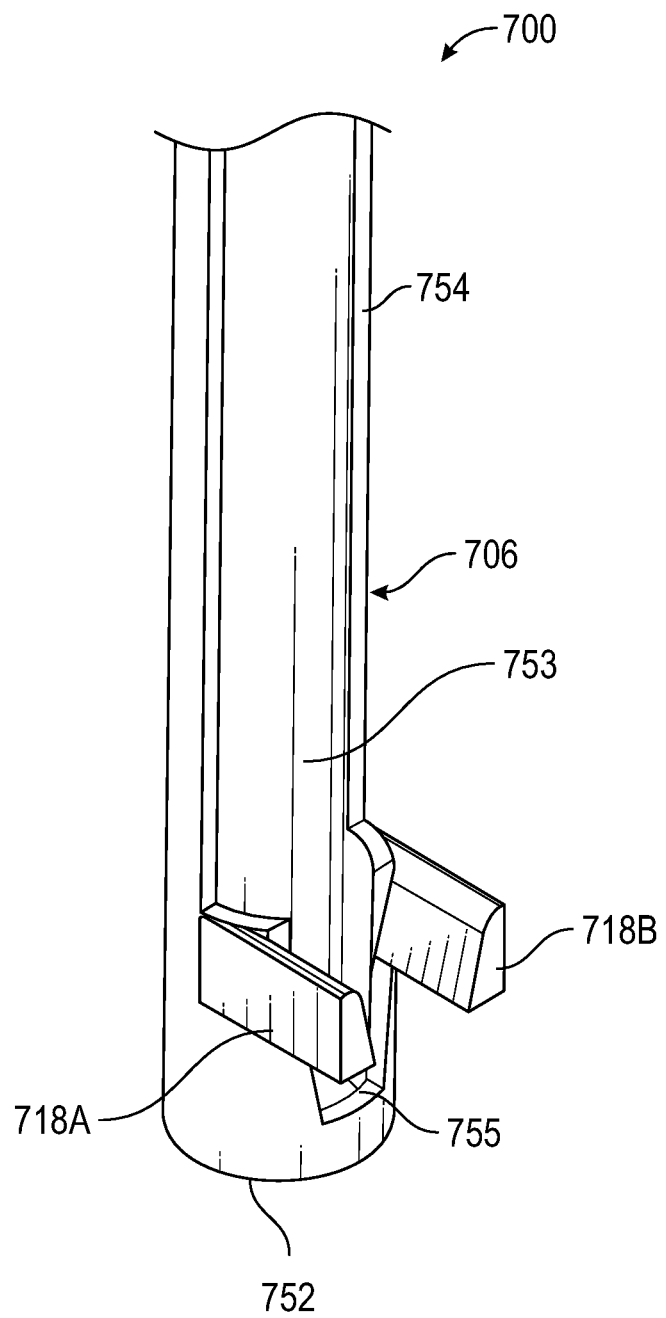
FIG. 41 is an enlarged exploded view of the device of FIG. 30 taken along circle 41 of FIG. 32.

Referring directly to FIGS. 30, 31 and 40, the first coupler arm 701A and the second coupler arm 701B of the pair of coupler arms 701 are joined together at the free end 736 of the inner rod 735 by the lower post 710. In particular, the first coupler arm 701A and the second coupler arm 701B each include a free end 761A and 761B and a pivotable end 762A and 762B. The pivotable ends 762A and 762B of each coupler arm 701A and 701B are joined by and rotatable about the lower post 708. The coupler arms 701A and 701B are operable to assume an open configuration as shown specifically in FIG. 30, and a closed configuration as shown specifically in FIG. 31. As illustrated in the exploded view of FIG. 40, the first and second coupler arms 701A and 701B are biased in the open configuration by a tensioning element 725. As the carriage 706 is forced upward in the second axial direction B, the bias provided by the tensioning element 725 is overridden and the first and second coupler arms 701A and 701B are forced together by the first and second wedges 718A and 718B to the closed configuration as shown specifically in FIG. 31. To return to the open configuration, the carriage 706 is actuated downward in the second axial direction B. This motion causes the tensioning element 725 to force the coupler arms 701A and 701B apart as the first and second wedges 718A and 718B are moved downward in the first axial direction A relative to the lower post 710 associated with the elongated body 705. Each respective coupler arm 706A and 706B includes a receptacle 764A and 764B including an open portion 765A and 765B configured to receive a portion 702A or 702B of a ring-and-pin coupler 702. Each respective portion 702A or 702B of the ring-and-pin coupler 702 can be removed from the respective coupler arm 706A or 706B through the open portion 765A or 765B of the coupler arm 706A or 706B.

During actuation of the carriage 706 in the second axial direction B, the free ends 761A and 761B of each coupler arm 706A and 706B are forced upward by the first and second wedges 718A and 718B and are drawn together into the closed configuration. The lower post 708 and the pivotable ends 762A and 762B of each coupler arm 706A and 706B are seated within the lower notch 755 of the carriage 710 when in the closed configuration.

Referring to FIGS. 30-32 and 39, in some embodiments the actuator 740 includes a rack-and-pinion arrangement to actuate the carriage 710 in the second axial direction B. In particular, the proximal portion 751 of the carriage 710 includes a rack 712 including a plurality of teeth 714 for engagement with a pinion 713 associated with the proximal portion 731 of the elongated body 705. In a primary embodiment, the pinion 713 is rotatable by the dial 704, however in some embodiments the pinion 713 is rotatable by another means such as a crank mechanism. The proximal portion 731 of the elongated body 705 can further define an actuator housing 741 that receives the pinion 713 and dial 704 as shown. In some embodiments, the elongated body 705 further includes one or more grip elements 711 in association with the actuator housing 741 that enables a practitioner to comfortably wield and stabilize the device 700 when coupling vessels together using the device 700. As shown, the proximal portion 731 of the elongated body 705 defines a surface 791 including the actuator slot 792 for passage of the proximal portion 751 of the carriage 710 between the carriage slot 739 and the actuator housing 741. To actuate the carriage 706 in the second axial direction B, the pinion 713 is rotated in a first rotational direction R. Likewise, to actuate the carriage 706 in the first axial direction A, the pinion 713 is rotated in a second rotational direction Q.

FIGS. 42-53 illustrate an embodiment of a coupler device, designated 800, having a first coupler arm 801A and a second coupler arm 801B in association with a rod 803. The first coupler arm 801A and the second coupler arm 801B are each configured to receive a respective portion 802A and 802B of a coupler ring 802. The rod 803 defines a proximal portion 831 and a distal portion 832 associated with the first and second coupler arms 801A and 801B. The rod 803 is operable for actuation in a first axial direction A by an actuator 840 in association with the proximal portion 831 of the rod 803. The elongated body 810 includes a first wedge 818A and an opposite second wedge 818B configured to guide the first and second coupler arms 801A and 801B together as the rod 803 is actuated in the first axial direction A. The first and second coupler arms 801A and 801B and consequently the first and second portions 802A and 802B of the coupler ring 802 are drawn together. This arrangement enables the first and second coupler arms 801A and 801B to assume an open configuration or a closed configuration. The elongated body 810 includes a proximal portion 851, a distal portion 852, and a channel 815 defined axially through the elongated body 810 for receipt of the rod 803. The proximal portion 851 of the elongated body 810 is configured to house or otherwise provide support for the actuator 840 and the proximal portion 831 of the rod 803. As shown, in some embodiments, the distal portion 832 of the rod 803 engages the coupler arms 801 at a lower block 821. The lower block 821 can in some embodiments be removeable from the distal portion 832 of the rod 803 and can in some embodiments be disposable along with the first and second coupler arms 801A and 801B. In some embodiments, a material of the lower block 821 and first and second coupler arms 801A and 801B can include rigid medical grade plastic from a grouping including but not limited to: ABS, Acetal, Polycarbonate, PETG, HDPE.

Figures 42, 43:
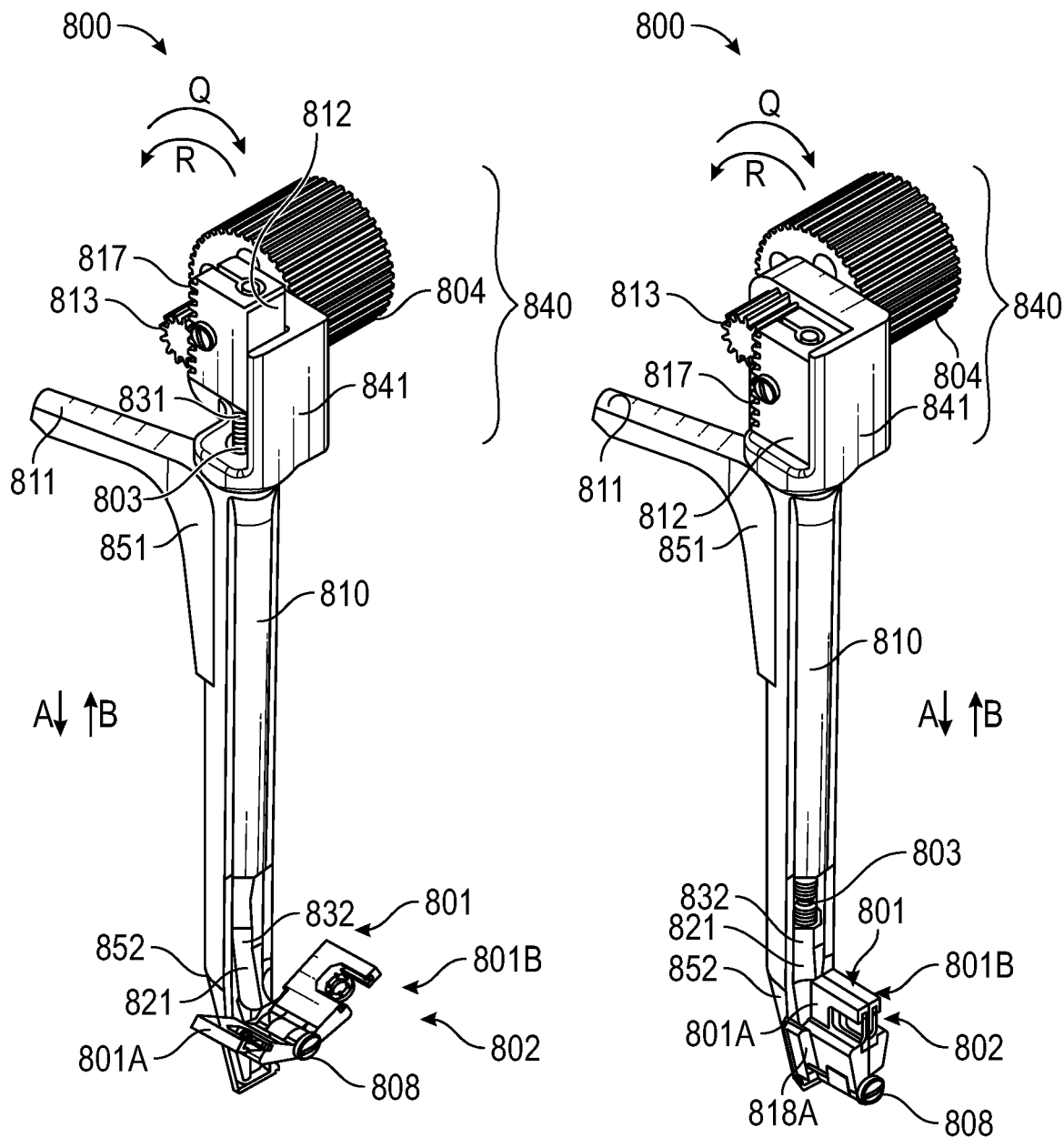
FIG. 42 is a perspective view of an eighth embodiment of a device for a microvascular anastomosis related to FIG. 1 in an open configuration.
FIG. 43 is a perspective view of the device of FIG. 42 in a closed configuration.
Figure 53:
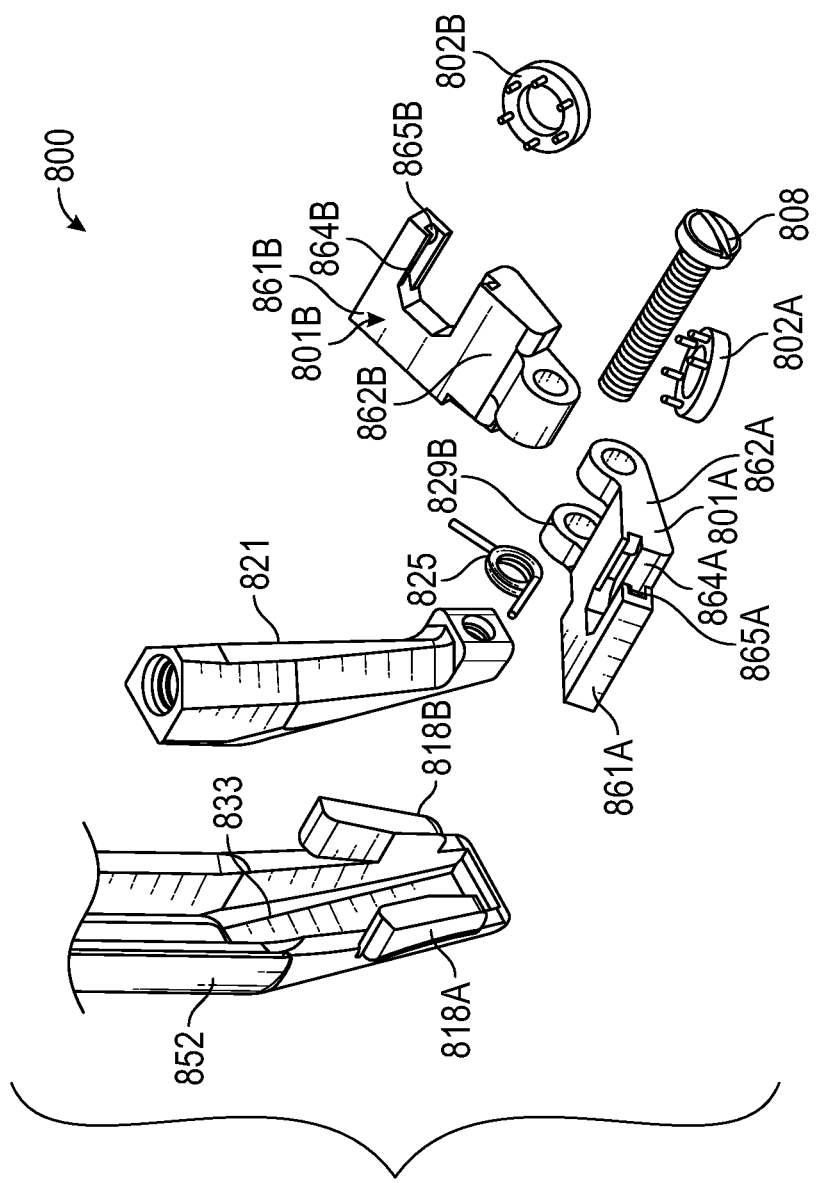
FIG. 53 is an enlarged exploded view of the device of FIG. 42 taken along circle 53 of FIG. 44.

Referring directly to FIGS. 42, 43 and 53, the first coupler arm 801A and the second coupler arm 801B of the pair of coupler arms 801 are joined together at the lower block 821 by the lower post 808. In particular, the first coupler arm 801A and the second coupler arm 801B each include a free end 861A and 861B and a pivotable end 862A and 862B; the pivotable ends 862A and 862B of each coupler arm 801A and 801B are joined by and rotatable about the lower post 808. The coupler arms 801A and 801B are operable to assume an open configuration as shown specifically in FIG. 42, and a closed configuration as shown specifically in FIG. 43. As illustrated in the exploded view of FIG. 40, the first and second coupler arms 801A and 801B are biased in the open configuration by a tensioning element 825. As the rod 805 is forced downward in the first axial direction A, the bias provided by the tensioning element 825 is overridden and the first and second coupler arms 801A and 801B are forced together by the first and second wedges 818A and 818B to the closed configuration as shown specifically in FIG. 43. To return to the open configuration, the rod 805 is actuated upward in the second axial direction B. This motion causes the tensioning element 825 to force the coupler arms 801A and 801B apart as the lower post 808 is moved upward relative to the first and second wedges 818A and 818B are moved upward in the second axial direction B. Each respective coupler arm 801A and 801B includes a receptacle 864A and 864B including an open portion 865A and 865B configured to receive a portion 802A or 802B of a ring-and-pin coupler 802. Each respective portion 802A or 802B of the ring-and-pin coupler 802 can be removed from the respective coupler arm 801A and 801B through the open portion 865A and 865B of the coupler arm 801A and 801B.

To close the coupler arms 801, the pinion 811 is rotated in a first rotational direction Q, the associated rack 812 is driven in the first axial direction A along with the remainder of the rod 803 associated with the rack 812. During actuation of the rod 805 in the first axial direction A, the lower post 808 is guided downward through the lower portion 833 of the channel 815 as the rod 805 is forced downward in the first axial direction A. This motion forces the free ends 861A and 861B of each coupler arm 801A and 801B upward. As the pivotable ends 862A and 862B of each coupler arm 801A and 801B are connected by the lower post 808, the free ends 861A and 861B of each coupler arm 801A and 801B are drawn together into the closed configuration as the pivotable ends 862A and 862B are forced downward in the first axial direction A. The free ends 861A and 861B of each coupler arm 801A and 801B are guided together by the first and second wedges 818A and 818B. The lower post 808 and the pivotable ends 862A and 862B of each coupler arm 801A and 801B are seated within the lower portion 833 of the channel 815 when in the closed configuration.

Figure 44:
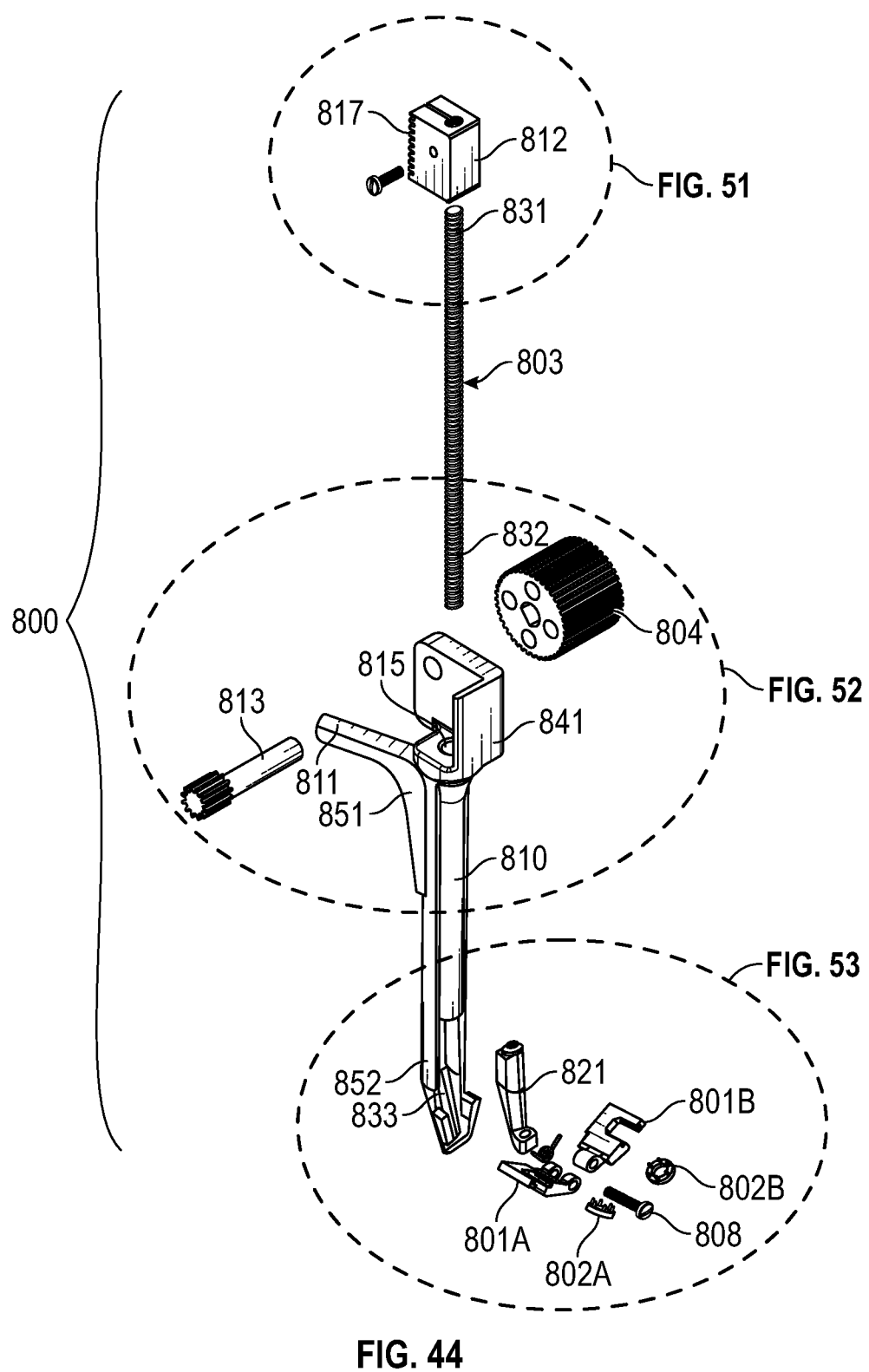
FIG. 44 is an exploded perspective view of the device of FIG. 42.
Figure 45:
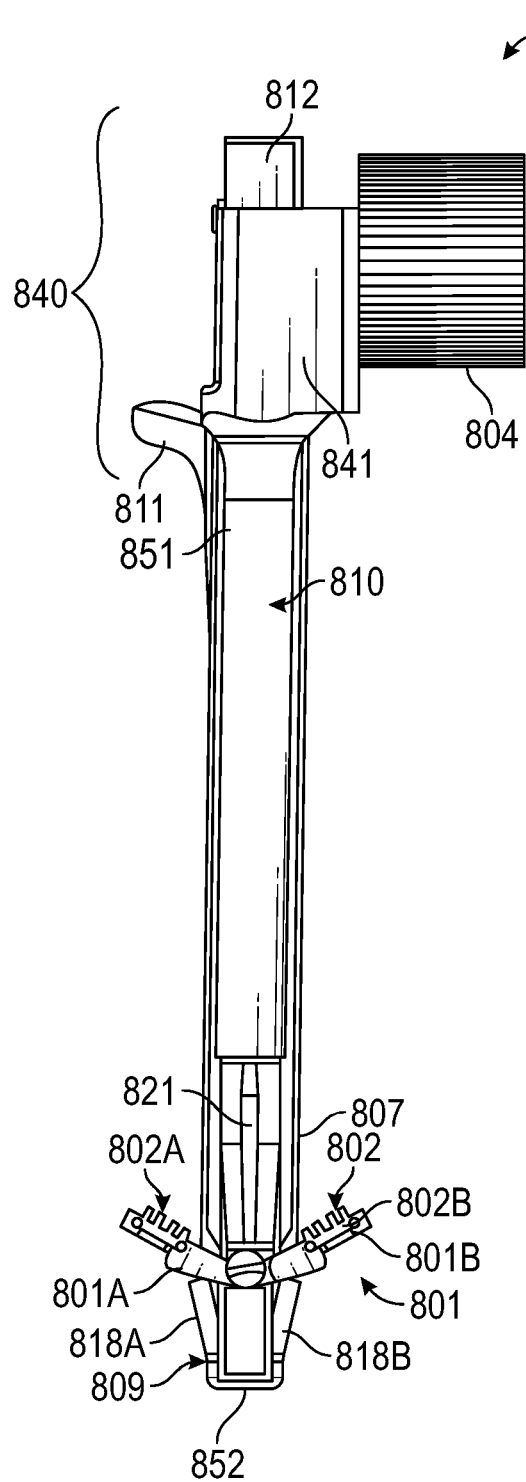
FIG. 45 is a front view of the device of FIG. 42 in the open configuration.
Figure 46:
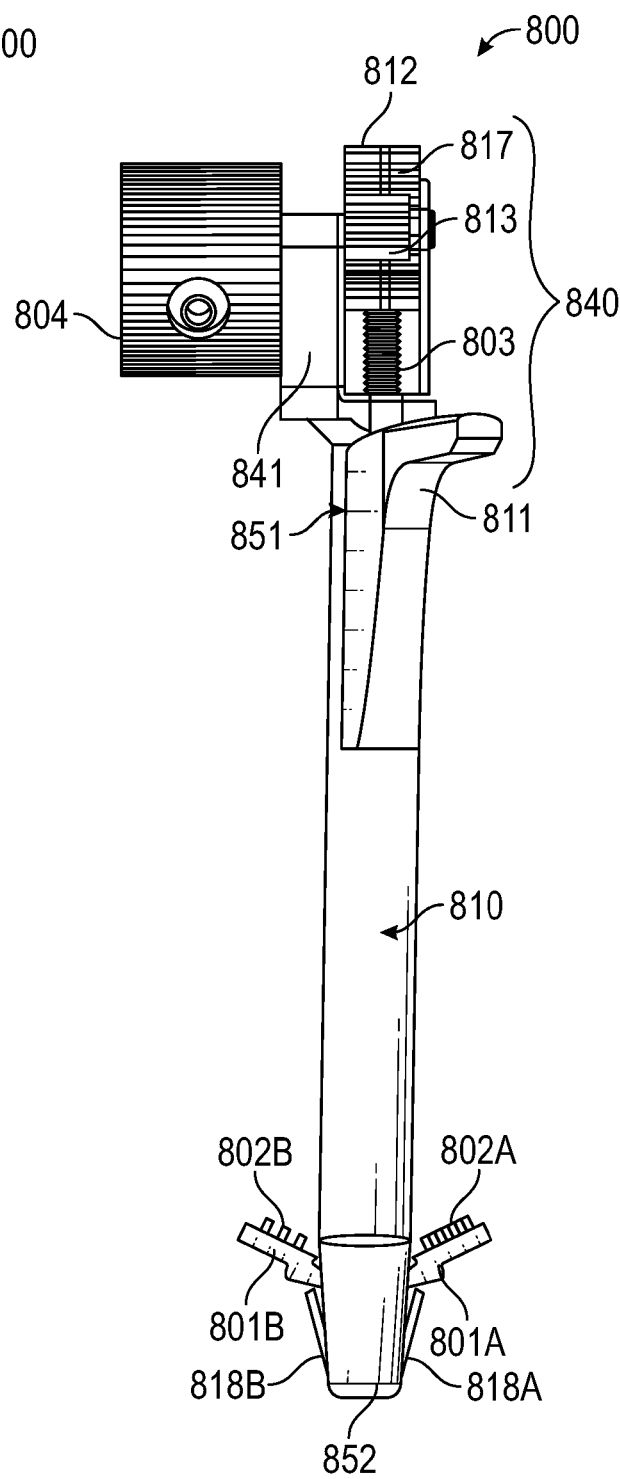
FIG. 46 is a rear view of the device of FIG. 42 in the open configuration.
Figure 47:
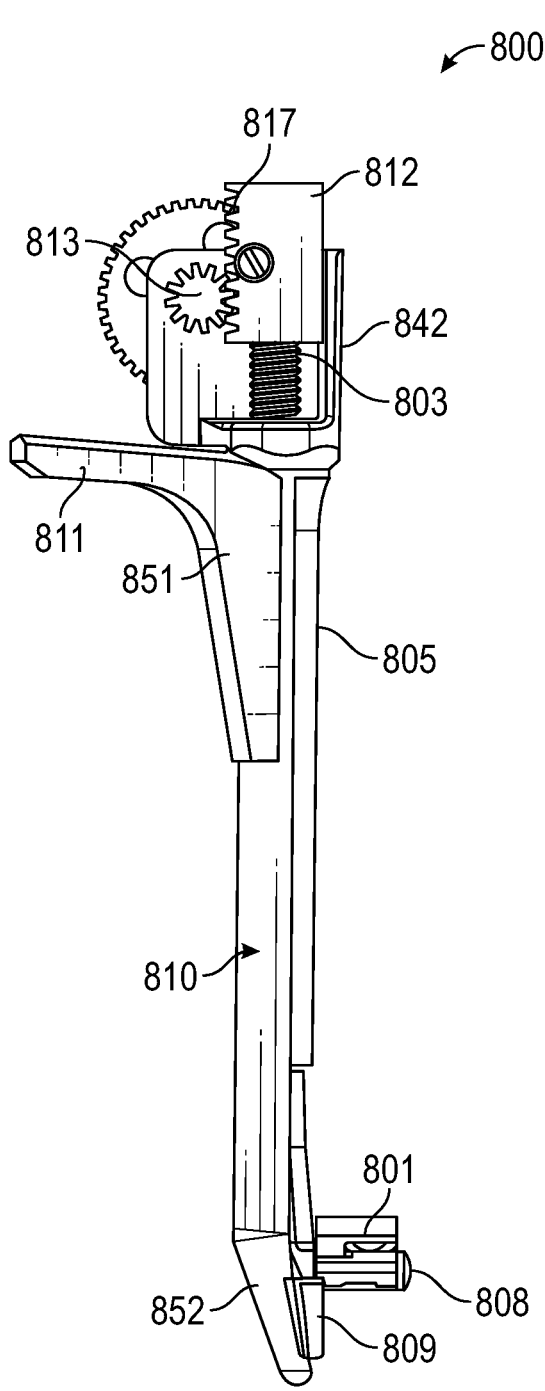
FIG. 47 is a left side view of the device of FIG. 42.
Figure 48:
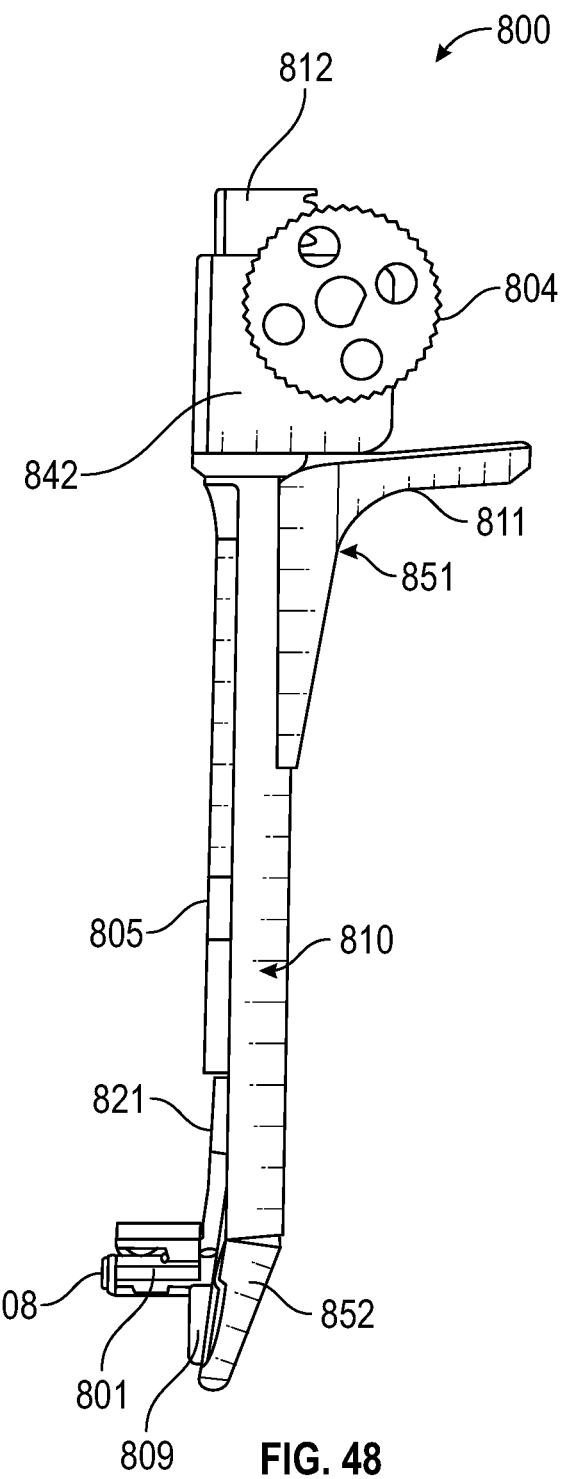
FIG. 48 is a right side view of the device of FIG. 42.
Figure 49:
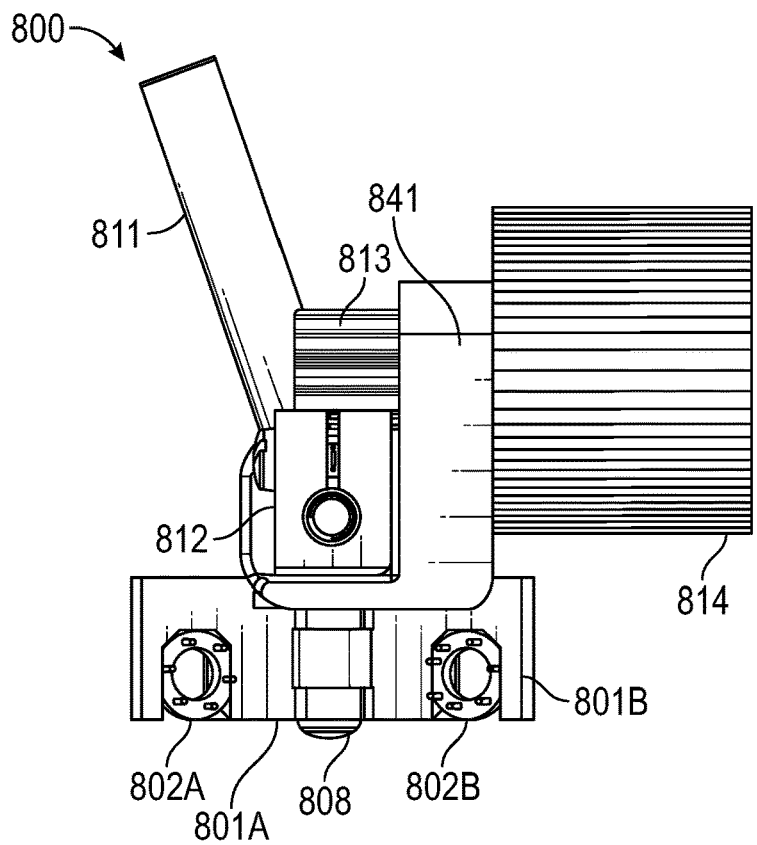
FIG. 49 is a top view of the device of FIG. 42.
Figure 50:
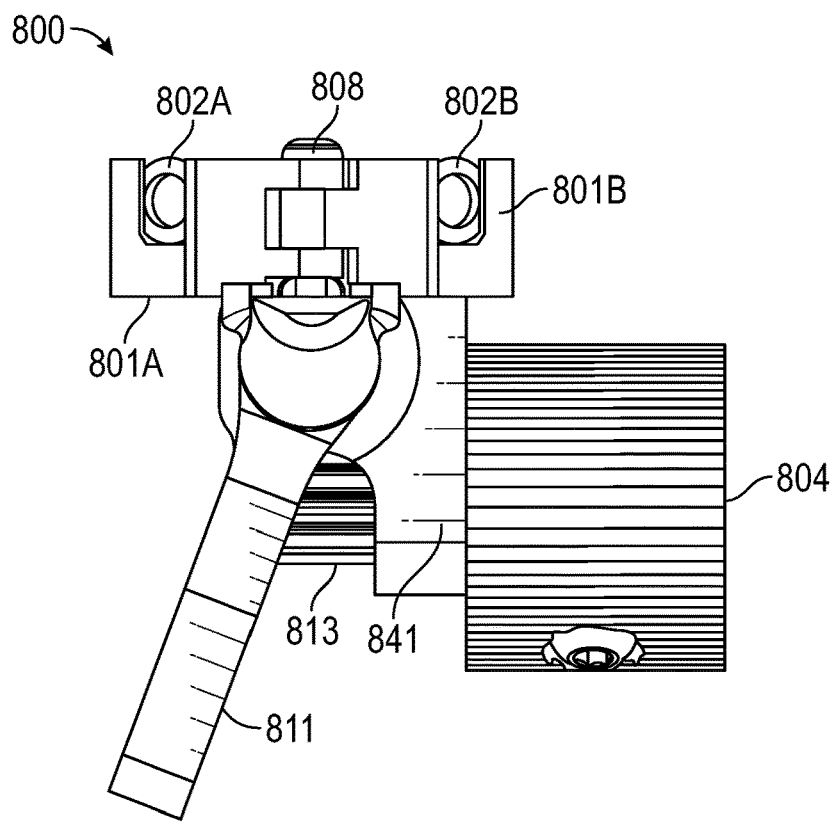
FIG. 50 is a bottom view of the device of FIG. 42.
Figure 51:
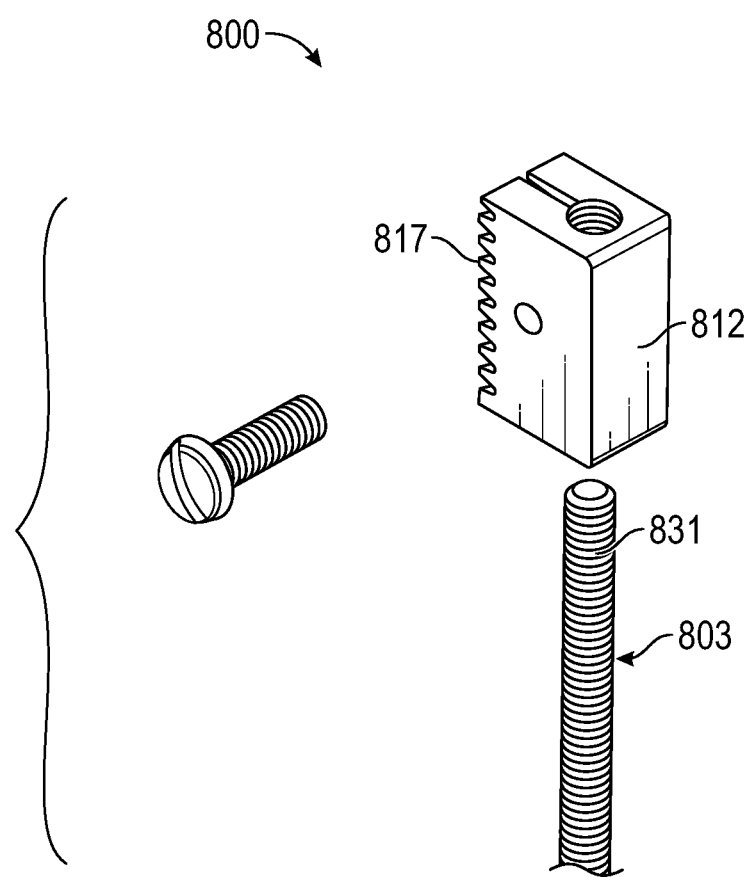
FIG. 51 is an enlarged exploded view of the device of FIG. 42 taken along circle 51 of FIG. 44.
Figure 52:
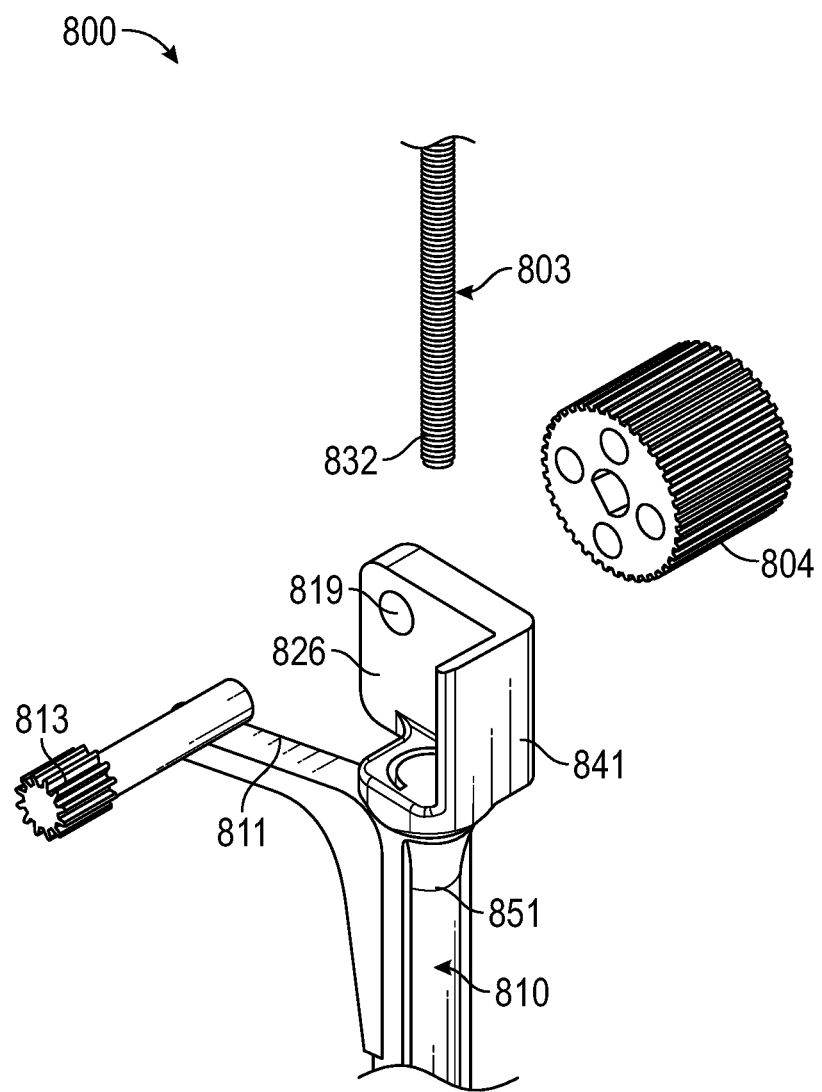
FIG. 52 is an enlarged exploded view of the device of FIG. 42 taken along circle 52 of FIG. 44.

Referring to FIGS. 44, 51 and 52, in some embodiments the actuator 840 includes a rack-and-pinion arrangement to actuate the rod 805 in the first axial direction A. In particular, the proximal portion 831 of the rod 805 includes a rack 812 including a plurality of teeth 817 for engagement with a pinion 813 associated with the proximal portion 851 of the elongated body 810. In a primary embodiment, the pinion 813 is rotatable by the dial 804, however in some embodiments the pinion 813 is rotatable by another means such as a crank mechanism. The proximal portion 831 of the elongated body 810 can further define an actuator housing 841 that receives the pinion 813 and dial 804 as shown. In some embodiments, the elongated body 810 further includes one or more grip elements 811 in association with the actuator housing 841 that enables a practitioner to comfortably wield and stabilize the device 800 when coupling vessels together using the device 800.

FIGS. 54-64 illustrate an embodiment of a coupler device, designated 900, having a first coupler arm 901A and a second coupler arm 901B in association with a rod 903. The first coupler arm 901A and the second coupler arm 901B are each configured to receive a respective portion 902A and 902B of a coupler ring 902. The rod 903 defines a proximal portion 931 and a distal portion 932 associated with the first and second coupler arms 901A and 901B. The rod 903 is operable for actuation in a first axial direction A by an actuator 940 in association with the proximal portion 931 of the rod 903. As the rod 903 is actuated in the first axial direction A, the first and second coupler arms 901A and 901B and consequently the first and second portions 902A and 902B of the coupler ring 902 are drawn together in a closed configuration. This arrangement enables the first and second coupler arms 901A and 901B to assume an open configuration or the closed configuration. The coupler device 900 further defines an elongated body 910 including a proximal portion 951, a distal portion 952, and a channel 915 defined axially through the elongated body 910 for receipt of the rod 903. In the embodiment shown, the elongated body 910 and rod 903 each define a squared profile. The proximal portion 951 of the elongated body 910 is configured to house or otherwise provide support for the actuator 940 and the proximal portion 951 of the rod 903. The first coupler arm 901A includes a first intermediate post 920A fixed to or otherwise associated with the distal portion 952 of the elongated body 910 along a first side 907A of the elongated body 910. Similarly, the second coupler arm 901B includes a second intermediate post 920B fixed to or otherwise associated with the distal portion 952 of the elongated body 910 along a second side 907B of the elongated body 910. The first and second coupler arms 901A and 901B are each rotatable about their respective first and second intermediate posts 920A and 920B to enable the coupler device 900 to open and close while reducing the profile of the coupler device 900.

Figure 54:
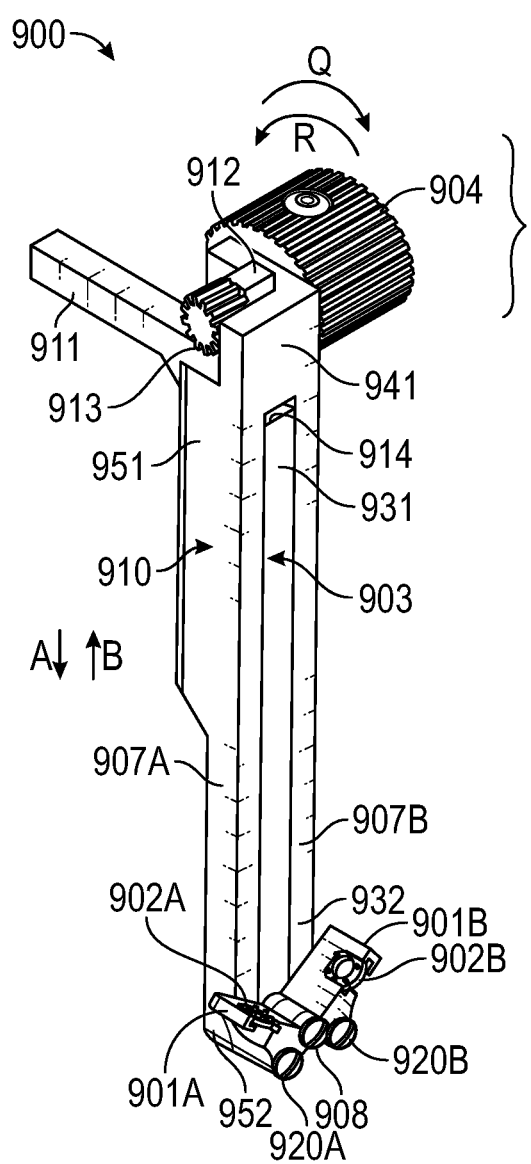
FIG. 54 is a perspective view of a ninth embodiment of a device for a microvascular anastomosis related to FIG. 1 in an open configuration.
Figure 55:
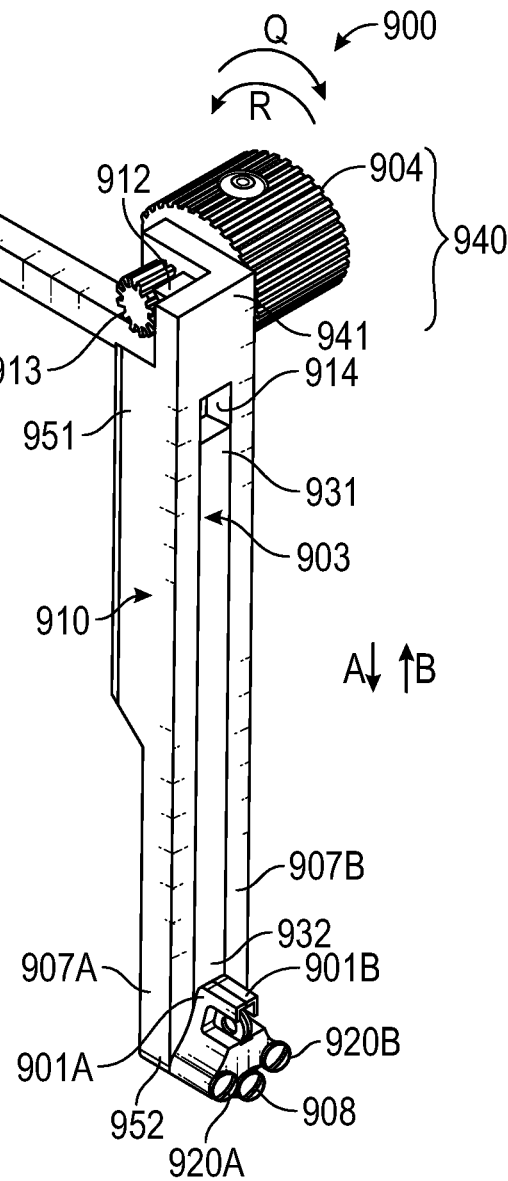
FIG. 55 is a perspective view of the device of FIG. 54 in a closed configuration.
Figure 56:
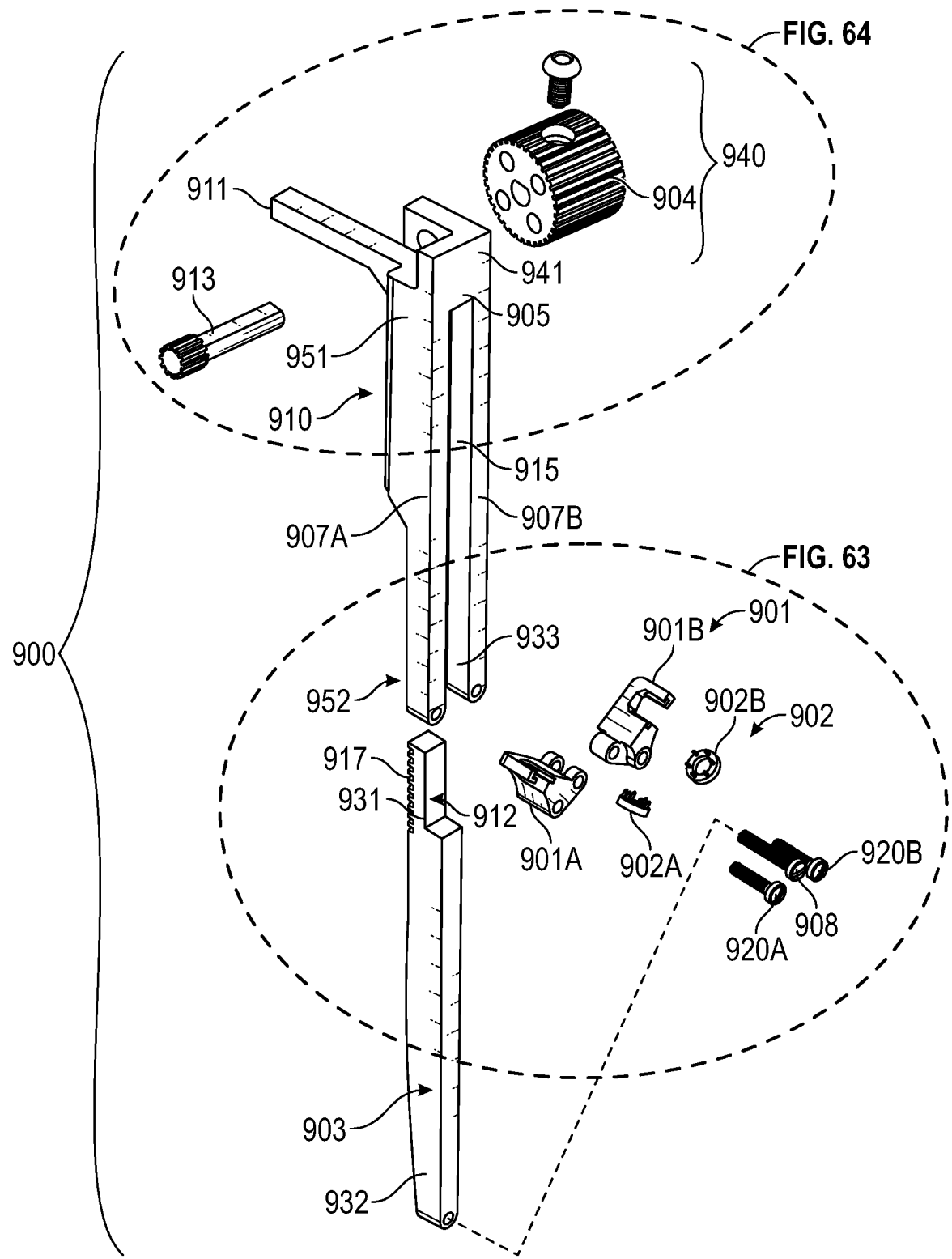
FIG. 56 is an exploded view of the device of FIG. 54.
Figures 57, 58:
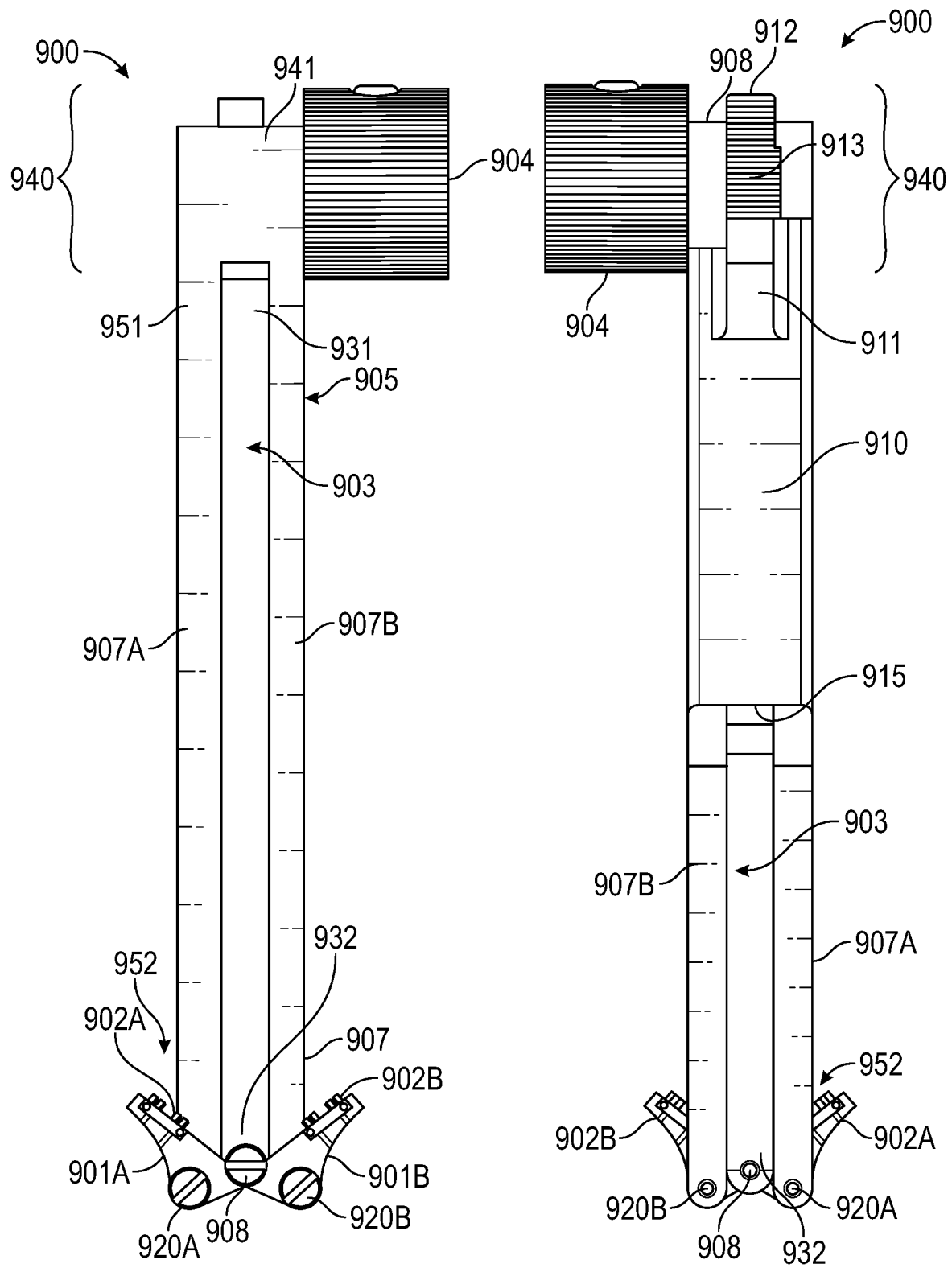
FIG. 57 is a front view of the device of FIG. 54 in the open configuration.
FIG. 58 is a rear view of the device of FIG. 54 in the open configuration.
Figures 59, 60:
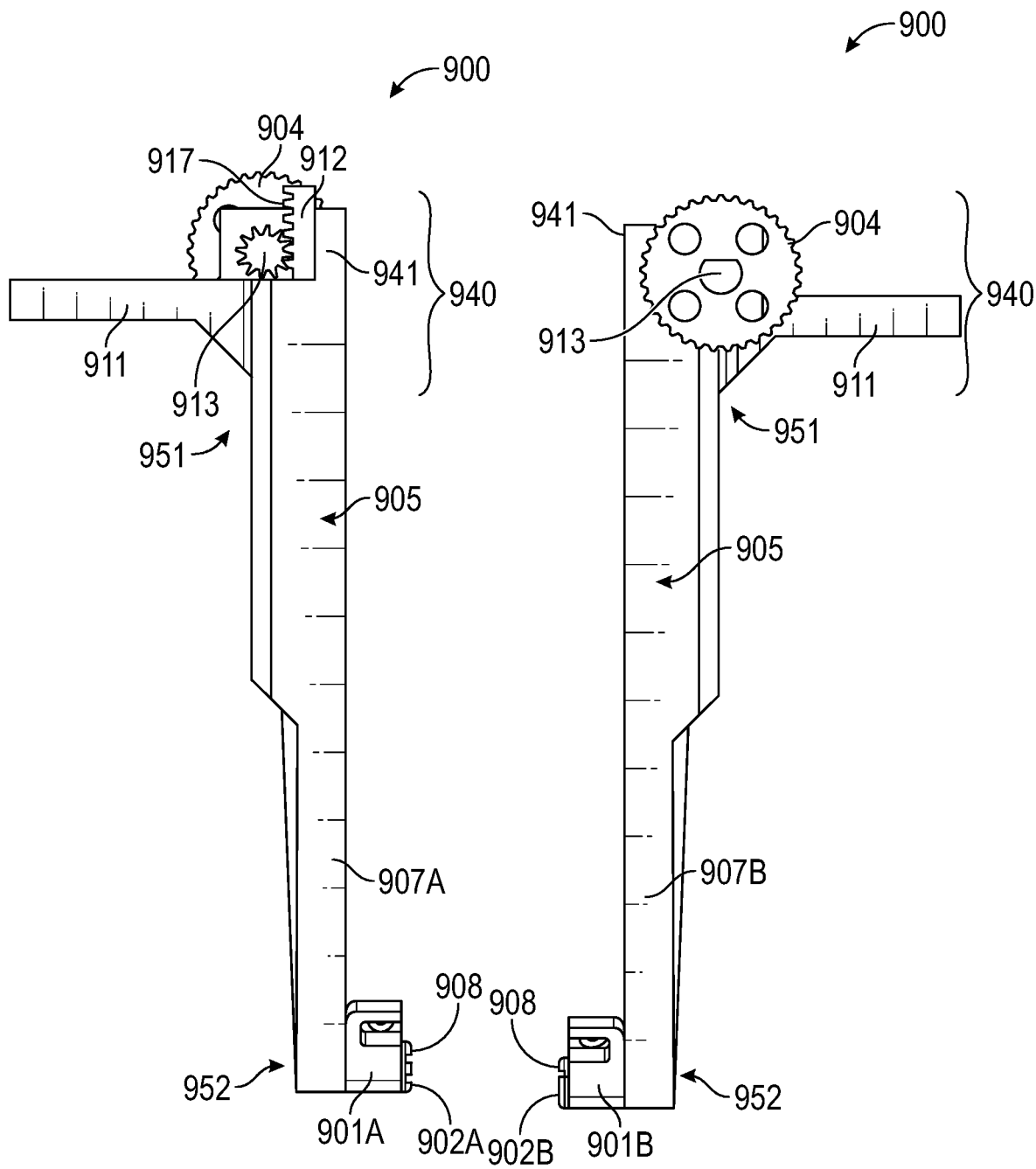
FIG. 59 is a left side view of the device of FIG. 54.
FIG. 60 is a right side view of the device of FIG. 54.
Figure 61:
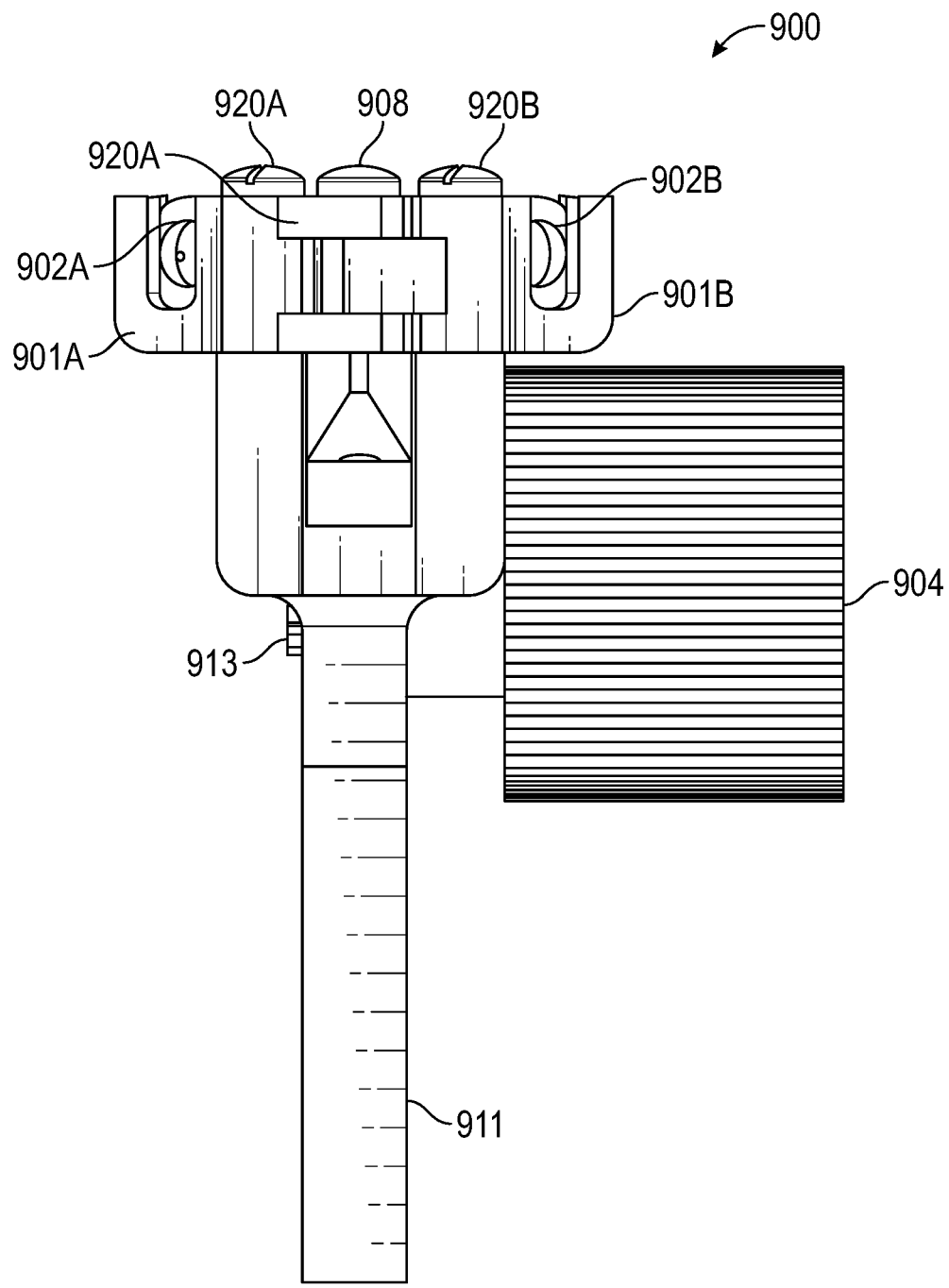
FIG. 61 is a bottom view of the device of FIG. 54.
Figure 62:
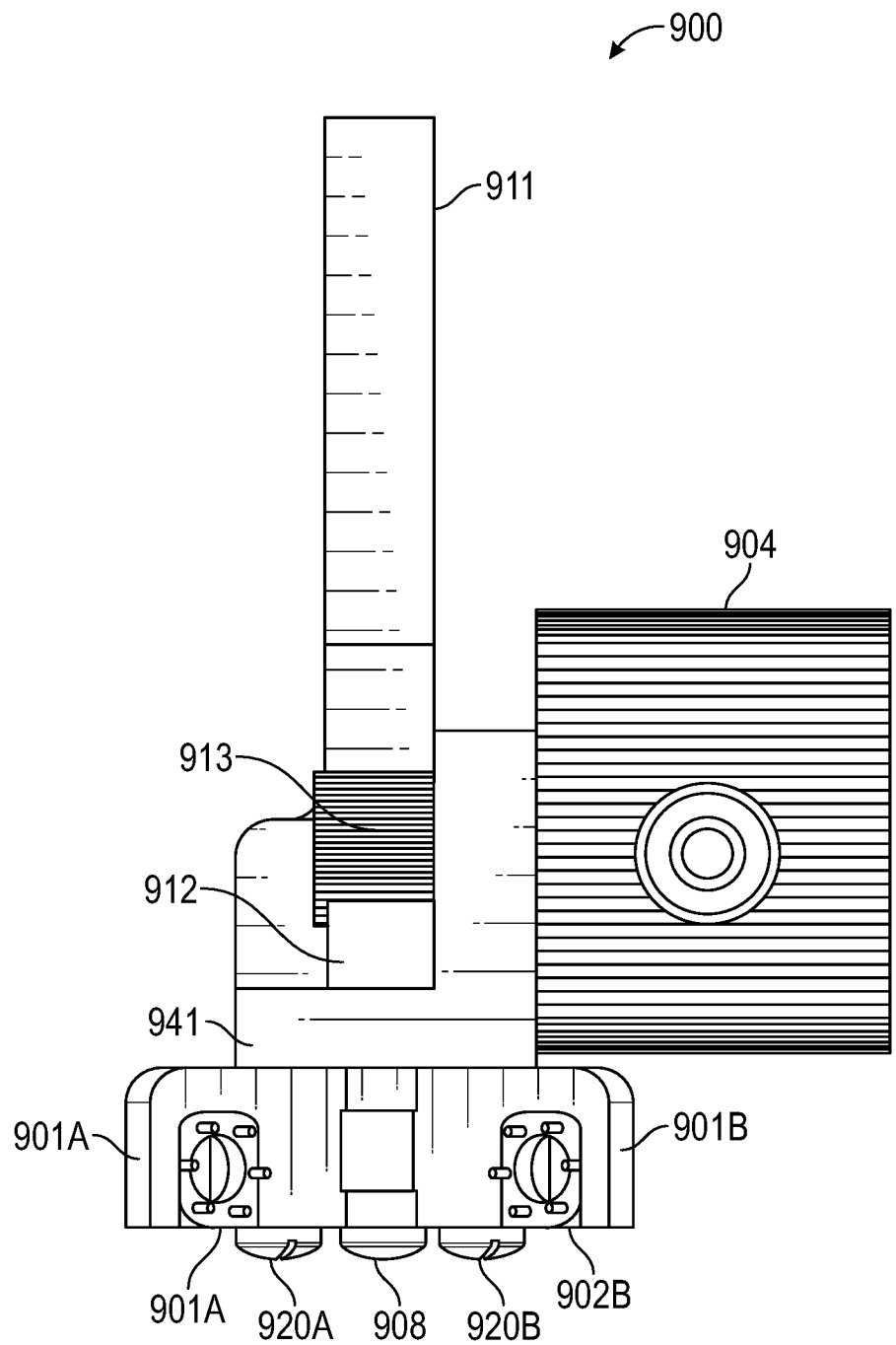
FIG. 62 is a top view of the device of FIG. 54.
Figure 63:
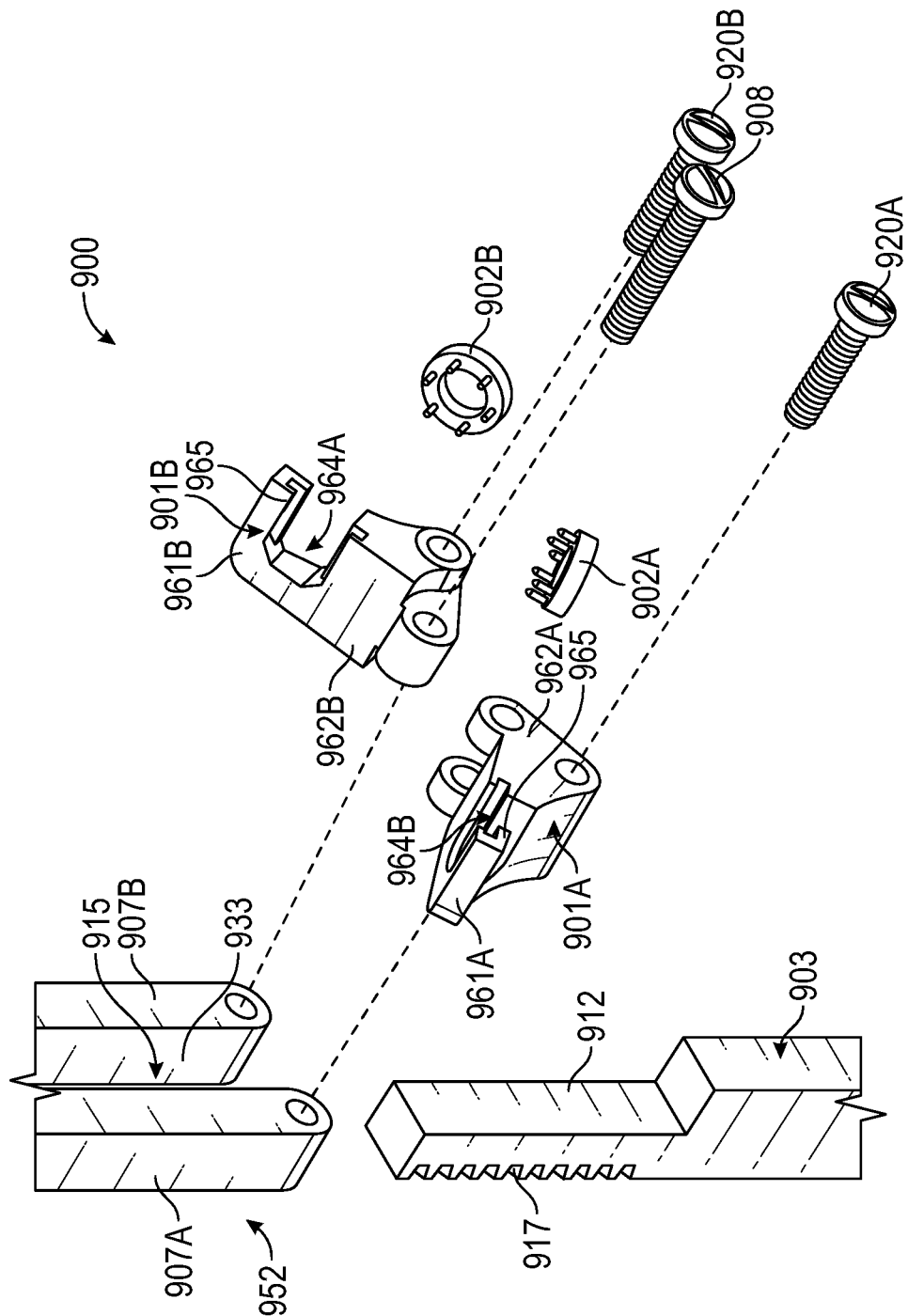
FIG. 63 is an enlarged exploded view of the device of FIG. 54 taken along circle 63 of FIG. 56
Figure 64:
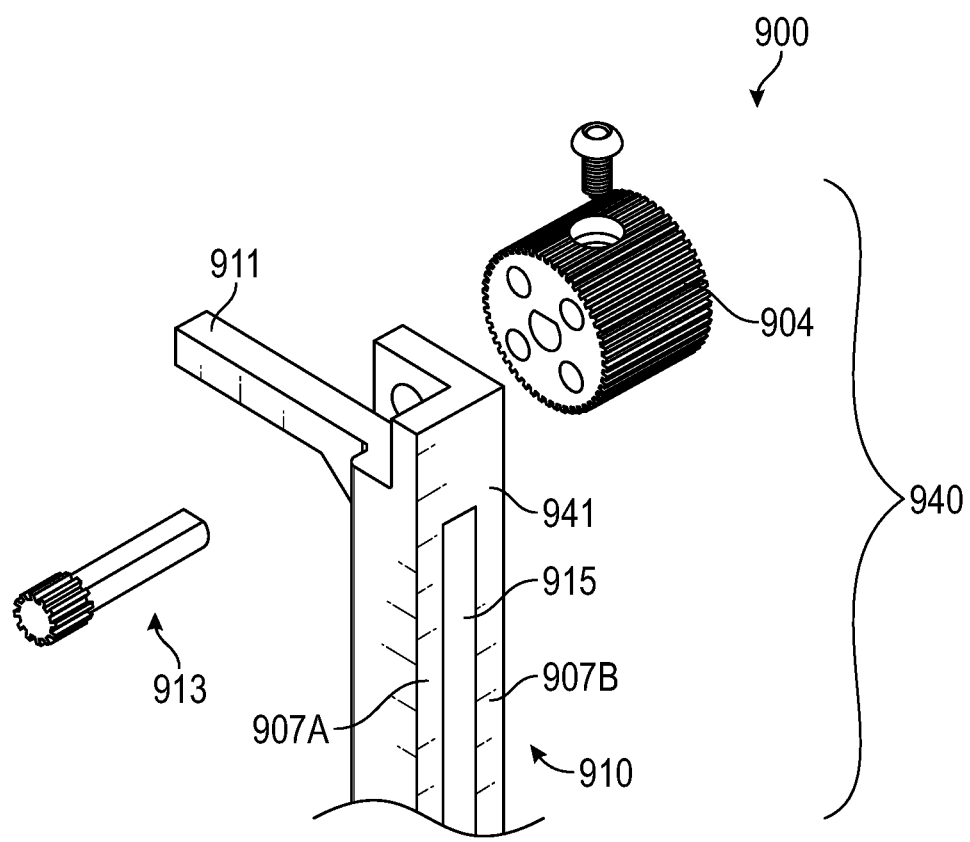
FIG. 64 is an enlarged exploded view of the device of FIG. 54 taken along circle 64 of FIG. 56.
Figure 67:
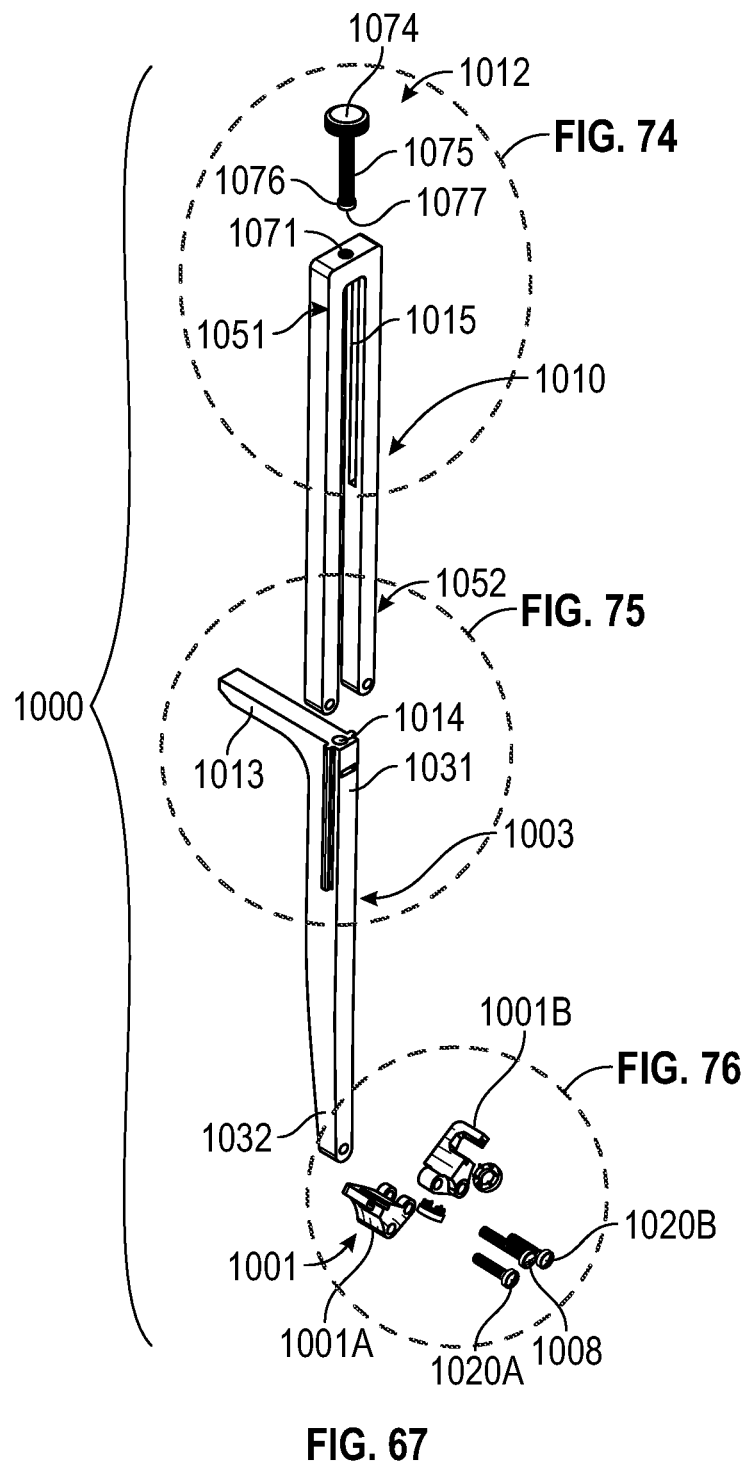
FIG. 67 is an exploded view of the device of FIG. 65.
Figures 70, 71:
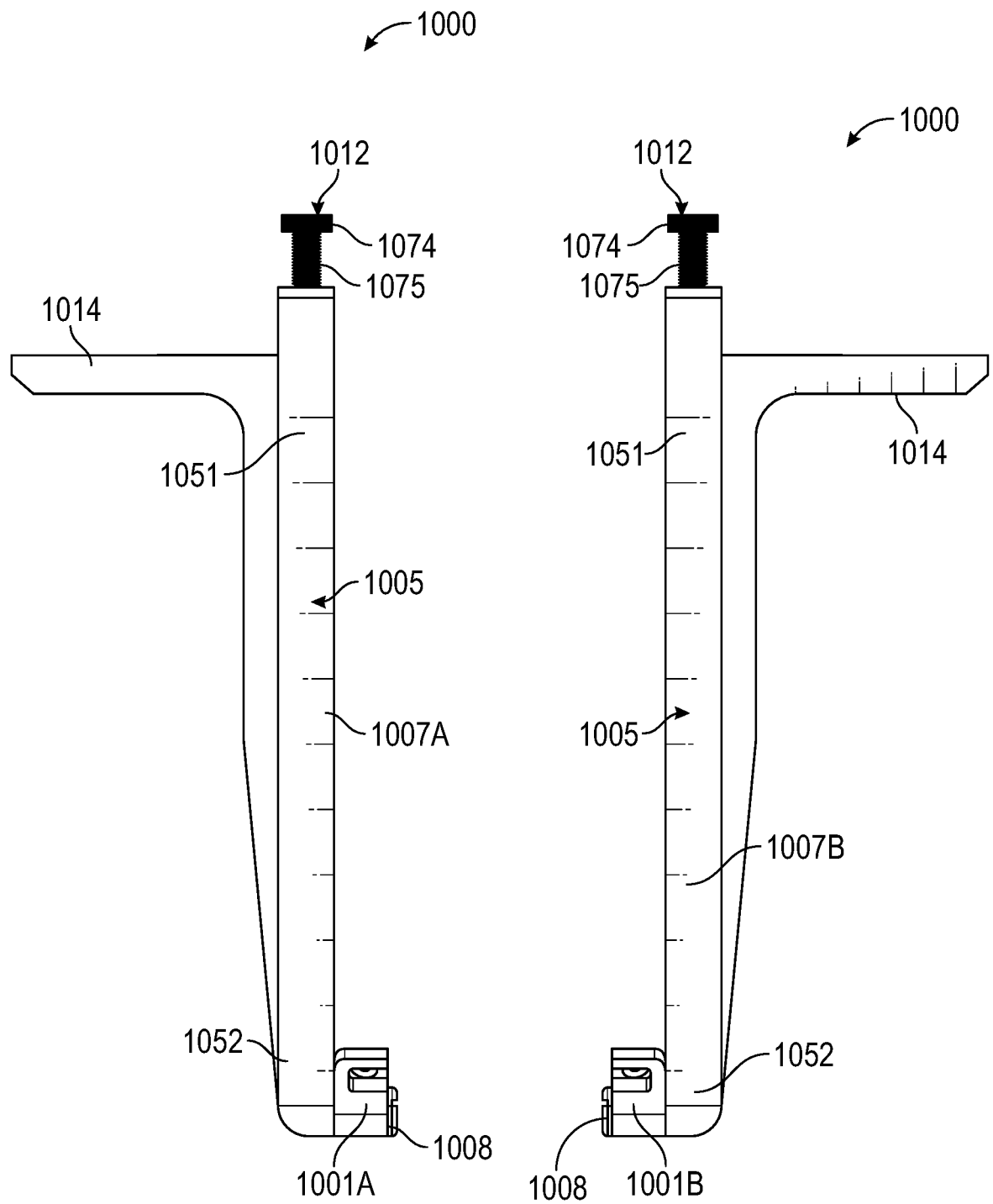
FIG. 70 is a left side view of the device of FIG. 65.
FIG. 71 is a right side view of the device of FIG. 65.
Figure 72:
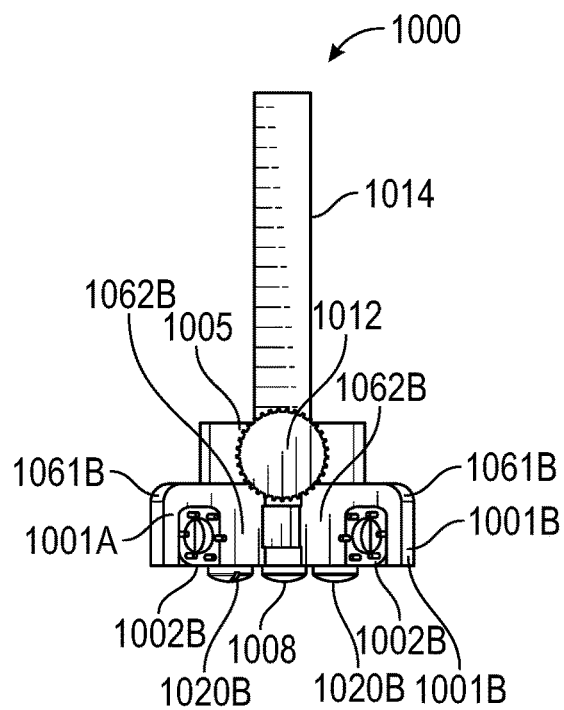
FIG. 72 is a top view of the device of FIG. 65.
Figure 73:
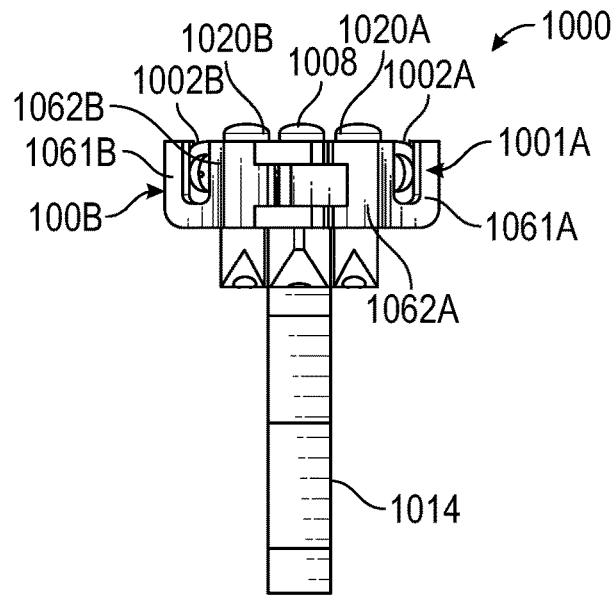
FIG. 73 is a bottom view of the device of FIG. 65.
Figure 74:
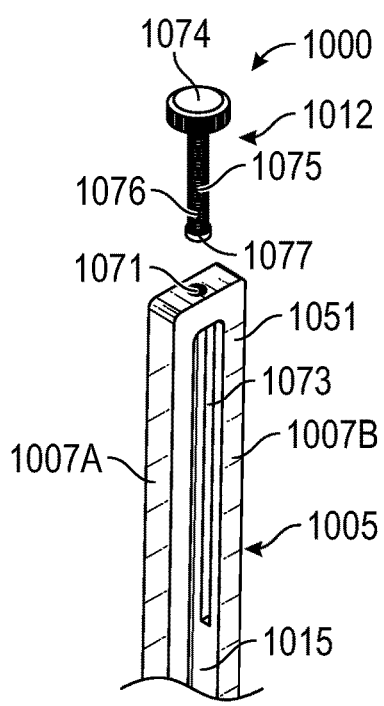
FIG. 74 is an enlarged exploded view of the device of FIG. 65 taken along circle 74 of FIG. 67.
Figure 75:
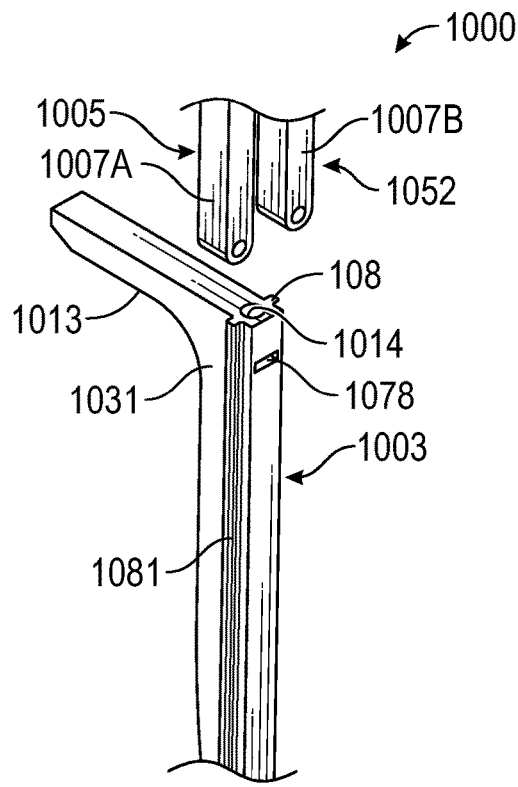
FIG. 75 is an enlarged exploded view of the device of FIG. 65 taken along circle 75 of FIG. 67.
Figure 76:
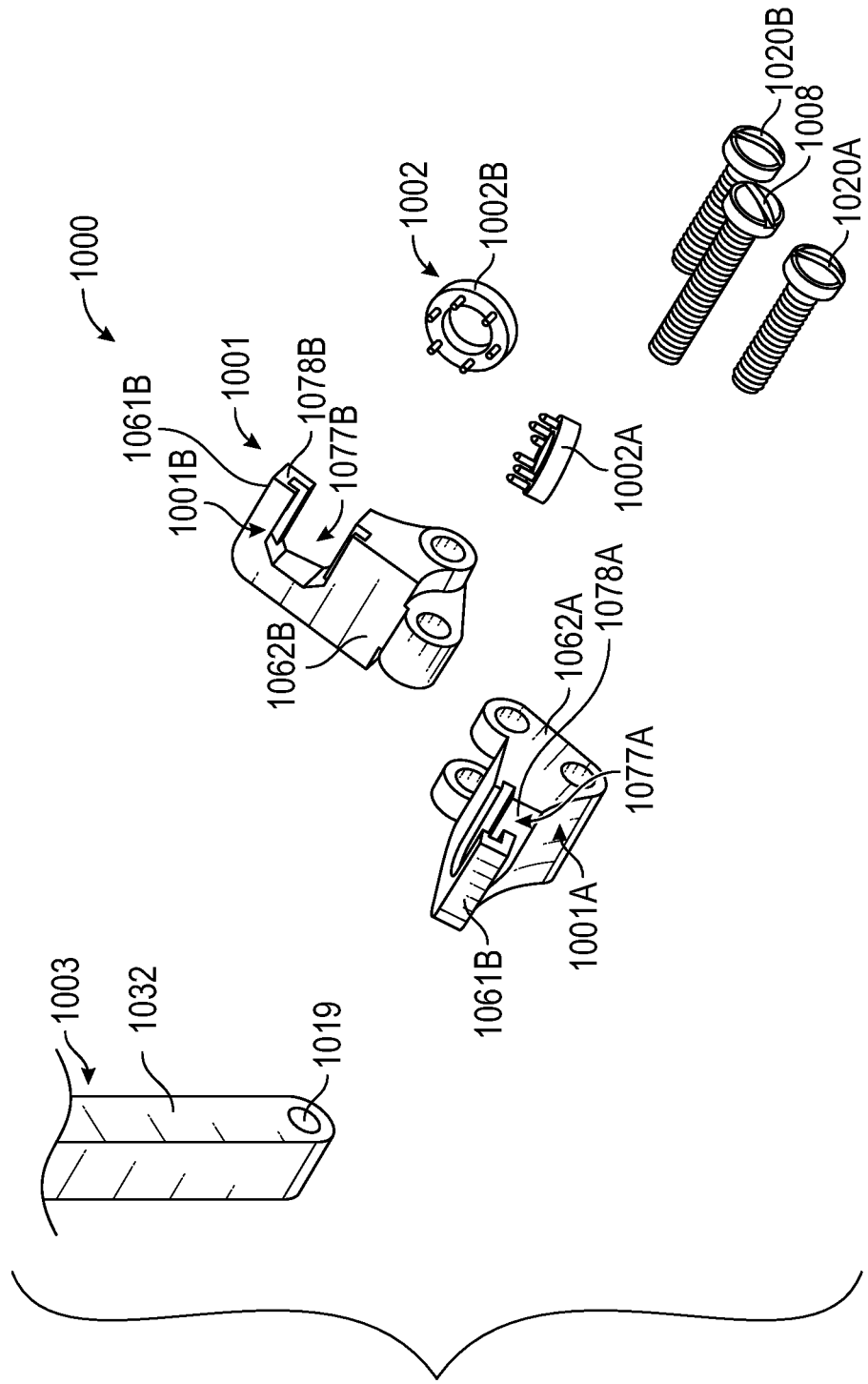
FIG. 76 is an enlarged exploded view of the device of FIG. 65 taken along circle 76 of FIG. 67.

Referring directly to FIGS. 54, 55 and 63, the first coupler arm 901A and the second coupler arm 901B of the pair of coupler arms 901 are joined at the distal portion 931 of the rod 903 by a lower post 908. In particular, the first coupler arm 901A and the second coupler arm 901B each include a respective free end 961A and 961B and a pivotable end 962A and 962B. The pivotable ends 962A and 962B of each coupler arm 901A and 901B are joined by and rotatable about the lower post 908. The coupler arms 901A and 901B are operable to assume an open configuration as shown specifically in FIG. 54, and a closed configuration as shown specifically in FIG. 55. The first coupler arm 901A includes a first intermediate post 920A in association with the distal portion 952 of the elongated body 910 along the first side 907A of the elongated body 910. Similarly, the second coupler arm 901B includes a second intermediate post 920B in association with the distal portion 952 of the elongated body 910 along the second side 907B of the elongated body 910. During actuation of the rod 903 in the first axial direction A, the lower post 908 is guided downward through the channel 915 as the rod 903 is forced downward in the first axial direction A. This motion forces the pivotable ends 962A and 962B of each coupler arm 901A and 901B downward. As the pivotable ends 962A and 962B of each coupler arm 901A and 901B are connected by the lower post 908, the free ends 961A and 961B of each coupler arm 901A and 901B are drawn together into the closed configuration as the pivotable ends 962A and 962B are forced downward in the first axial direction A. This motion is guided by the first and second intermediate posts 920A and 920B which are fixed directly to the first and second sides 907A and 907B of the elongated body 910 together as shown between FIGS. 54 and 55.

Each respective coupler arm 901A and 901B includes a receptacle 964A and 964B having an open portion 965A and 965B configured to receive a portion 902A or 902B of a ring-and-pin coupler 902. Each respective portion 902A or 902B of the ring-and-pin coupler 902 can be removed from the respective coupler arm 901A and 901B through the open portion 965A and 965B of the coupler arm 901A and 901B.

Referring to FIGS. 54-56, 63 and 64, in some embodiments the actuator 940 includes a rack-and-pinion arrangement to actuate the rod 903 in the first axial direction A. In particular, the proximal portion 931 of the rod 903 includes a rack 912 including a plurality of teeth 917 for engagement with a pinion 913 associated with the proximal portion 931 of the elongated body 910. In a primary embodiment, the pinion 913 is rotatable by the dial 904, however in some embodiments the pinion 913 is rotatable by another means such as a crank mechanism. The proximal portion 931 of the elongated body 910 can further define an actuator housing 941 that receives the pinion 913 and dial 904 as shown. In some embodiments, the elongated body 910 further includes a grip element 911 in association with the actuator housing 941 that enables a practitioner to wield and stabilize the device 900 when coupling vessels together using the device 900.

To close the coupler arms 901, the pinion 913 is rotated in a first rotational direction Q, the associated rack 912 is driven in the first axial direction A along with the remainder of the rod 903 associated with the rack 912. During actuation of the rod 903 in the first axial direction A by the pinion 913, the lower post 908 is guided downward through a lower portion 933 of the channel 915 as the rod 903 is forced downward in the first axial direction A. This motion forces each coupler arm 901A and 901B together in the closed configuration. Similarly, to open the coupler arms 901, the pinion 913 is rotated in an opposite second rotational direction R, the associated rack 912 is driven in a second axial direction B along with the remainder of the rod 903 associated with the rack 912. During actuation of the rod 903 in the second axial direction B by the pinion 913, the lower post 908 is guided upward through the lower portion 933 of the channel 915 as the rod 903 is forced upward in the second axial direction B. This motion forces each coupler arm 901A and 901B apart to the open configuration FIGS. 65-76 illustrate an embodiment of a coupler device, designated 1000, having a first coupler arm 1001A and a second coupler arm 1001B in association with a rod 1003. The first coupler arm 1001A and the second coupler arm 1001B are each configured to receive a respective portion 1002A and 1002B of a coupler ring 1002. The rod 1003 defines a proximal portion 1031 and a distal portion 1032 associated with the first and second coupler arms 1001A and 1001B. The rod 1003 is operable for actuation in a first axial direction A by an actuator 1040 in association with the proximal portion 1031 of the rod 1003. As the rod 1003 is actuated in the first axial direction A, the first and second coupler arms 1001A and 1001B and consequently the first and second portions 1002A and 1002B of the coupler ring 1002 are drawn together in a closed configuration. This arrangement enables the first and second coupler arms 1001A and 1001B to assume an open configuration or the closed configuration. The coupler device 1000 further defines an elongated body 1010 including a proximal portion 1051, a distal portion 1052, and a channel 1015 defined axially through the elongated body 1010 for receipt of the rod 1003. In the embodiment shown, the elongated body 1010 and rod 1003 each define a squared profile. The proximal portion 1051 of the elongated body 1010 is configured to house or otherwise provide support for the actuator 1041 and the proximal portion 1031 of the rod 1003. The first coupler arm 1001A includes a first intermediate post 1020A fixed to or otherwise associated with the distal portion 1052 of the elongated body 1010 along a first side 1007A of the elongated body 1010. Similarly, the second coupler arm 1001B includes a second intermediate post 1020B fixed to or otherwise associated with the distal portion 1052 of the elongated body 1010 along a second side 1007B of the elongated body 1010. The first and second coupler arms 1001A and 1001B are each rotatable about their respective first and second intermediate posts 1020A and 1020B to enable the coupler device 1000 to open and close while reducing the profile of the coupler device 1000. The actuator 1040, unlike the previously-described 900 embodiment, can alternatively include a screw 1012 rotatably mounted to contact the first portion of the rod 1003 such that as the screw 1012 is rotated in a clockwise or counterclockwise direction S about a rod axis, the rod 1003 is consequently actuated in the first axial direction A.

Referring directly to FIGS. 65 and 66, the first coupler arm 1001A and the second coupler arm 1001B of the pair of coupler arms 1001 are joined at a distal portion 1032 of the rod 1003 by a lower post 1008. In particular, the first coupler arm 1001A and the second coupler arm 1001B each include a respective free end 1061A and 1061B and a pivotable end 1062A and 1062B. The pivotable ends 1062A and 1062B of each coupler arm 1001A and 1001B are joined by and rotatable about the lower post 1008. The coupler arms 1001A and 1001B are operable to assume an open configuration as shown specifically in FIG. 65, and a closed configuration as shown specifically in FIG. 66. The first coupler arm 1001A includes a first intermediate post 1020A in association with the distal portion 1052 of the elongated body 1010 along the first side 1007A of the elongated body 1010. Similarly, the second coupler arm 1001B includes a second intermediate post 1020B in association with the distal portion 1052 of the elongated body 1010 along the second side 1007B of the elongated body 1010. During actuation of the rod 1003 in the first axial direction A, the lower post 1008 is guided downward through the channel 1015 as the rod 1003 is forced downward in the first axial direction A. This motion forces the pivotable ends 1062A and 1062B of each coupler arm 1001A and 1001B downward. As the pivotable ends 1062A and 1062B of each coupler arm 1001A and 1001B are connected by the lower post 1008, the free ends 1061A and 1061B of each coupler arm 1001A and 1001B are drawn together into the closed configuration as the pivotable ends 1062A and 1062B are forced downward in the first axial direction A. This motion is guided by the first and second intermediate posts 1020A and 1020B which are fixed directly to the first and second sides 1007A and 1007B of the elongated body 1010 together as shown between FIGS. 65 and 66.

Each respective coupler arm 1001A and 1001B includes a receptacle 1064A and 1064B including an open portion 1065A and 1065B configured to receive a portion 1002A or 1002B of a ring-and-pin coupler 1002. Each respective portion 1002A or 1002B of the ring-and-pin coupler 1002 can be removed from the respective coupler arm 1001A and 1001B through the open portion 1065A and 1065B of the coupler arm 1001A and 1001B.

Referring to FIGS. 65-68, 74 and 75, in some embodiments the actuator 1040 includes a screw arrangement to actuate the rod 1003 in the first axial direction A. In particular, the actuator 1040 includes a screw 1012 in association with the proximal portion 1031 of the rod 1003 and the proximal portion 1051 of the elongated body 1010. The elongated body 1010 includes a threaded hole 1071 defined at the proximal portion 1051 of the elongated body 1010 for receipt of the screw 1012, in addition to a first track (not shown) and a second track 1073 defined on either side of the channel 1015 of the elongated body 1010. The rod 1003 includes a first ridge 1081 and an opposite second ridge 1082 for respective engagement with the first track (not shown) and second track 1073. The rod 1003 includes a hole 1014 in coaxial alignment with the threaded hole 1071 of the elongated body 1010.

The screw 1012 includes a head 1074 and a member 1075 defining a distal portion 1076. The distal portion 1076 of the member 1075 of the screw 1012 is inserted through the threaded hole 1014 and contacts the first portion 1031 of the rod 1003 such that as the screw 1012 is driven in a clockwise or counterclockwise direction S about a rod axis, the rod 1010 is consequently actuated in the first axial direction A to the closed configuration. In some embodiments, the rod 1003 further includes a grip element 1013 in association with the proximal portion 1031 of the rod 1003 that enables a practitioner to wield and stabilize the device 1000 when coupling vessels together using the device 1000. As shown, the rod 1003 can further include a first and second ridge 1081 and 1082 for respective engagement with the first track (not shown) and the second track 1073 of the elongated body 1010. The screw 1012 is configured for engagement with a retention component 1077 that engages the distal portion 1076 of the screw 1012 and prevents the screw 1012 from pulling out of the hole 1014 of the rod 1010. As shown, the rod 1003 includes a slot 1078 for insertion of the retention component 1077 to enable assembly of the device 1000. Upon insertion of the retention component 1077 within the slot 1078, the distal portion 1076 engages the retention component 107 and prevents pullout of the screw 1012 from the rod 1003.

To close the coupler arms 1006, the screw 1004 is rotated in a first rotational direction S, the associated rod 1003 is driven in the first axial direction A along with the remainder of the rod 1003 associated with the rack 1012. During actuation of the rod 1003 in the first axial direction A by the screw 1004, the lower post 1008 is guided downward through a lower portion 1033 of the channel 1015 as the rod 1003 is forced downward in the first axial direction A. This motion forces each coupler arm 1001A and 1001B together in the closed configuration. Similarly, to open the coupler arms 1006, the screw 1004 is rotated in an opposite second rotational direction T, the associated rod 1003 is driven in a second axial direction B along with the lower post 1008. During actuation of the rod 1003 in the second axial direction B, the lower post 1008 is guided upward through the lower portion 1033 of the channel 1015 as the rod 1003 is forced upward in the second axial direction B. This motion forces each coupler arm 1001A and 1001B apart to the open configuration.

Some embodiments of the devices 100, 200, 300, 400, 500, 600, 700, 800, 900, 1000 may be reusable or disposable. For a reusable embodiment, the device may comprise a metallic material, such as stainless steel, substantially steel alloys, surgical grade steel, substantially titanium alloys, and substantially aluminum alloys. For a reusable embodiment, the device may need to be sterilized via autoclave.

For a disposable embodiment, the device may comprise a biocompatible polymer, resin, or injection molded thermoplastic. Since the material will be used for the body, a substantially rigid material may be used. Possible biocompatible materials may include polyvinylchloride, polyethersulfone, polytetrafluoroethylene, polyethylene, polyurethane, polyetherimide, polycarbonate, polysulfone, polyetheretherketone, polypropylene, acrylonitrile butadiene styrene, polyamide, polystyrene, and polylactic acid. For a disposable embodiment, the device may need to be sterilized via ethylene oxide, gamma radiation, or a combination of both.

Some embodiments of the devices 100, 200, 300, 400, 500, 600, 700, 800, 900, 1000 may be utilized by a single surgeon. The surgeon may need to utilize both hands when placing the ends of the vessel into their respective ring-and-pin couplers. When closing the ring-and-pin couplers together, the surgeon may only need one hand to reconfigure the device, as the device may be mounted at this time.

Referring to FIG. 77, embodiments of the devices 100, 200, 300, 400, 500, 600, 700, 800, 900, 1000 can be suspended or otherwise supported by a retractor arm 150 that grasps the device 100, 200, 300, 400, 500, 600, 700, 800, 900, 1000 outside an incision, flexible or otherwise. In some embodiments, a suitable retractor arm used in neurosurgery can include a Greenberg retractor arm, but it should be noted that the device 100, 200, 300, 400, 500, 600, 700, 800, 900, 1000 can be used with any retractor that might be used in other surgical subspecialties. In particular, as shown in FIG. 77, the retractor arm 150 grasps the device 100, 200, 300, 400, 500, 600, 700, 800, 900, 1000 at the associated grip element 207, 307, 507, 607, 711, 811, 911, or 1013. In other embodiments, the retractor arm 150 can grasp the device 100, 200, 300, 400, 500, 600, 700, 800, 900, 1000 at a selected point along the elongated body 210, 310, 410, 510, 610, 705, 810, 910, or 1010. In some embodiments, the retractor arm 150 can couple with a surgical bed or other stable structure.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

The invention claimed is:

1. A device, comprising:
an elongated body including a proximal portion, and an inner rod portion in coaxial alignment with an outer sheath portion collectively defining a carriage slot therebetween;
a carriage at least partially encapsulated within the carriage slot of the elongated body and defining a proximal portion and a distal portion, wherein the distal portion of the carriage includes a first wedge and an opposite second wedge;
an actuator in association with the proximal portion of the elongated body and the proximal portion of the carriage, wherein the actuator is operable to actuate the carriage in a second axial direction; and
a pair of coupling arms in association with the distal portion of the elongated body, wherein each coupling arm of the pair of coupling arms includes a free end and a pivotable end, wherein the pivotable end includes a lower post such that the coupling arm is operable to pivot about the lower post, and wherein the lower post is associated with the distal portion of the elongated body;
wherein the actuator is operable to actuate the carriage in the second axial direction such that the free end of a first coupling arm of the pair of coupling arms is drawn towards a free end of a second coupling arm of the pair of coupling arms in a closed configuration as the first wedge and the opposite second wedge of the carriage are actuated in the second axial direction.

2. The device of claim 1, wherein the first wedge and the opposite second wedge of the carriage contact a respective coupling arm of the pair of coupling arms and cause each coupling arm of the pair of coupling arms to pivot about the lower post.

3. The device of claim 2, wherein the carriage includes a lower notch in association with the first wedge and the opposite second wedge such that the lower post is received at the lower notch when the carriage is actuated in the second axial direction.

4. The device of claim 1, further comprising a tensioning element in association with the lower post such that the pair of coupling arms is biased in an open configuration.

5. The device of claim 1, wherein the actuator includes a pinion operable for rotation in a clockwise or counterclockwise direction about a pinion axis such that the carriage is consequently actuated in the second axial direction.

6. The device of claim 1, further comprising a grip element in association with the elongated body, wherein the grip element is configured for engagement with a surgical arm.

* * * * *